US008501716B2

(12) United States Patent
Zhou et al.

(10) Patent No.: US 8,501,716 B2
(45) Date of Patent: Aug. 6, 2013

(54) C7-FLUORO SUBSTITUTED TETRACYCLINE COMPOUNDS

(75) Inventors: Jingye Zhou, Belmont, MA (US); Xiao-Yi Xiao, San Diego, CA (US); Louis Plamondon, Belmont, MA (US); Diana Katharine Hunt, Cambridge, MA (US); Roger B. Clark, Lexington, MA (US); Robert B. Zahler, Pennington, NJ (US)

(73) Assignee: Tetraphase Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 13/570,837

(22) Filed: Aug. 9, 2012

(65) Prior Publication Data

US 2012/0302527 A1 Nov. 29, 2012

Related U.S. Application Data

(63) Continuation of application No. 12/462,795, filed on Aug. 7, 2009.

(60) Provisional application No. 61/188,307, filed on Aug. 8, 2008.

(51) Int. Cl.
*A61K 31/65* (2006.01)
*C07C 237/26* (2006.01)

(52) U.S. Cl.
USPC .......................................... 514/152; 552/205

(58) Field of Classification Search
USPC .......................................... 552/205; 514/152
See application file for complete search history.

(56) References Cited

U.S. PATENT DOCUMENTS

| | | | |
|---|---|---|---|
| 5,284,963 A | 2/1994 | Sum et al. |
| 5,328,902 A | 7/1994 | Sum et al. |
| 5,380,888 A | 1/1995 | Sum et al. |
| 5,401,729 A | 3/1995 | Sum et al. |
| 5,466,684 A | 11/1995 | Sum et al. |
| 5,494,903 A | 2/1996 | Hlavka et al. |
| 5,495,031 A | 2/1996 | Sum et al. |
| 5,529,990 A | 6/1996 | Hlavka et al. |
| 5,530,117 A | 6/1996 | Hlavka et al. |
| 5,574,026 A | 11/1996 | Backer et al. |
| 6,841,546 B2 | 1/2005 | Draper et al. |
| 6,914,057 B1 | 7/2005 | Ryan et al. |
| 7,045,507 B2 | 5/2006 | Draper et al. |
| RE40,086 E | 2/2008 | Hlavka et al. |
| RE40,183 E | 3/2008 | Hlavka et al. |
| 7,763,735 B2 | 7/2010 | Myers et al. |
| 7,807,842 B2 | 10/2010 | Myers et al. |
| 7,820,641 B2 | 10/2010 | Nelson et al. |
| 7,825,105 B2 | 11/2010 | Bandarage et al. |
| 2004/0063674 A1 | 4/2004 | Levy et al. |
| 2004/0092490 A1 | 5/2004 | Draper et al. |
| 2004/0214800 A1 | 10/2004 | Levy et al. |
| 2004/0242548 A1 | 12/2004 | Draper et al. |
| 2006/0166944 A1 | 7/2006 | Berniac et al. |
| 2006/0194773 A1 | 8/2006 | Levy et al. |
| 2006/0281717 A1 | 12/2006 | Berniac et al. |
| 2007/0093455 A1 | 4/2007 | Abato et al. |
| 2008/0015169 A1 | 1/2008 | Nelson et al. |
| 2008/0070873 A1 | 3/2008 | Alekshun et al. |
| 2008/0118979 A1 | 5/2008 | Draper et al. |
| 2009/0118269 A1 | 5/2009 | Berniac et al. |
| 2009/0257985 A1 | 10/2009 | Nelson et al. |
| 2010/0022483 A1 | 1/2010 | Berniac et al. |
| 2010/0105671 A1 | 4/2010 | Zhou et al. |
| 2012/0135968 A1 | 5/2012 | Chen et al. |
| 2012/0208788 A1 | 8/2012 | Deng et al. |

FOREIGN PATENT DOCUMENTS

| | | |
|---|---|---|
| EP | 0 582 789 A1 | 2/1994 |
| EP | 0 582 810 A1 | 2/1994 |
| GB | 935 384 | 8/1963 |
| WO | WO 00/18353 | 4/2000 |
| WO | WO 02/04404 A2 | 1/2002 |
| WO | WO 02/072022 A2 | 9/2002 |
| WO | WO 02/072031 A2 | 9/2002 |
| WO | WO 02/085303 A2 | 10/2002 |
| WO | WO 03/005971 A2 | 1/2003 |
| WO | WO 03/079984 A2 | 10/2003 |

(Continued)

OTHER PUBLICATIONS

Sato, F., et al. "Structure-Activity Relationship Investigation of Some New Tetracyclines by Electronic Index Methodology", *Los Alamos National Laboratory*, Quantitative Biology, 1-18 (Aug. 21, 2007).
Written Opinion of the International Searching Authority for International Application No. PCT/US2009/053142; Date Mailed: Oct. 13, 2009.
International Search Report for International Application No. PCT/US2009/053142; Date Mailed: Oct. 13, 2009.
Notification Concerning Transmittal of International Preliminary Report on Patentability for International Application No. PCT/US2009/053142 dated Feb. 17, 2011.
Notification of Transmittal of the International Search Report and the Written Opinion of the International Searching Authority, or the Declaration, in International Application No. PCT/US2010/001350; Date mailed: Nov. 23, 2010.

(Continued)

*Primary Examiner* — Barbara P Badio
(74) *Attorney, Agent, or Firm* — Hamilton, Brook, Smith & Reynolds, P.C.

(57) ABSTRACT

The present invention is directed to a compound represented by Structural Formula (A):

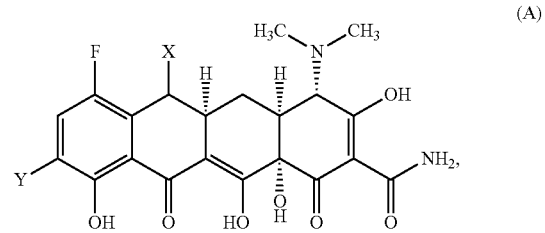

(A)

or a pharmaceutically acceptable salt thereof. The variables for Structural Formula (A) are defined herein. Also described is a pharmaceutical composition comprising the compound of Structural Formula (A) and its therapeutic use.

2 Claims, No Drawings

FOREIGN PATENT DOCUMENTS

| | | |
|---|---|---|
| WO | WO 2004/006850 A2 | 1/2004 |
| WO | WO 2004/038000 A2 | 5/2004 |
| WO | WO 2004/038001 A2 | 5/2004 |
| WO | WO 2005/112945 A2 | 12/2005 |
| WO | WO 2006/047671 A2 | 5/2006 |
| WO | WO 2006/084265 A1 | 8/2006 |
| WO | WO 2007/087416 A2 | 8/2007 |
| WO | WO 2007/117639 A2 | 10/2007 |
| WO | WO 2007/133798 A2 | 11/2007 |
| WO | WO 2008/045507 A2 | 4/2008 |
| WO | WO 2008/127361 A2 | 10/2008 |
| WO | WO 2008/127722 A1 | 10/2008 |
| WO | WO 2009/128913 A1 | 10/2009 |
| WO | WO 2010/017470 | 2/2010 |
| WO | WO 2010/126607 A2 | 11/2010 |
| WO | WO 2010/129057 A2 | 11/2010 |
| WO | WO 2011/025982 A2 | 3/2011 |
| WO | WO 2012/021712 | 2/2012 |
| WO | WO 2012/047907 A1 | 4/2012 |

OTHER PUBLICATIONS

International Preliminary Report on Patentability for International Application No. PCT/US2009/001350; Date Mailed: Nov. 9, 2011.

International Preliminary Report on Patentability for International Application No. PCT/US2010/047035; Date Mailed: Feb. 28, 2012.

Notification of Transmittal of International Search Report and the Written Opinion of the International Search Authority, or the Declaration, in International Application No. PCT/US2010/047035; Date mailed: Jul. 22, 2011.

Sun, C., et al., "A Robust Platform for the Synthesis of New Tetracycline Antibiotics,", *J. Am. Chem.Soc.*, 130:17913-17927 (2008).

Abbanat, D., et al., "New agents in development for the treatment of bacterial infections", *Current Opinion in Pharmacology*, 8(5): 582-592 (available online Sep. 18, 2008).

Podlogar, B., L., et al., "Patents on tetracycline and tetracyline derivatives as antimicrobials", *Expert Opin. Ther. Patents*, 13(4): 467-478 (2003).

Verma, A.K., et al., "Antibiotic and non-antibiotic tetracycline patents", Expert Opin. Ther. Patents, vol. 18, pp. 69-82 (2008).

Notification of Transmittal of the International Search Report and the Written Opinion of the International Searching Authority, or the Declaration, in International Application No. PCT/US2011/047428, 4 pages, date of mailing Jan. 6, 2012.

Hlavka, J.J., et al., "The 6-Deoxytetracyclines. IV. A Photochemical Displacement of a Diazonium Group," *Organic Chemical Research Section*, vol. 27, pp. 3674-3675 (1962).

Charest, M.G., et al., "A Convergent Enantioselective Route to Structurally Diverse 6-Deoxytetracycline Antibiotics," Science, 308: 395-398 (2005).

Office Action, U.S. Appl. No. 12/462,795, Dated: Dec. 7, 2011.

Office Action, U.S. Appl. No. 12/462,795, Dated: Jan. 24, 2012.

Office Action, U.S. Appl.n No. 12/462,795, Dated: Jul. 24, 2012.

Office Action, U.S. Appl. No. 13/718,909, Dated: Feb. 4, 2013.

Pre Appeal Brief Conference Decision, U.S. Appl. No. 12/462,795, Dated: Feb. 19, 2013.

Notification Concerning Transmittal of International Preliminary Report on Patentability for International Application No. PCT/US2011/047428; Date Mailed: Feb. 21, 2013.

C7-FLUORO SUBSTITUTED TETRACYCLINE COMPOUNDS

RELATED APPLICATION

This application is a continuation of U.S. application Ser. No. 12/462,795, filed Aug. 7, 2009, which claims the benefit of U.S. Provisional Application No. 61/188,307, filed on Aug. 8, 2008. The entire teachings of the above application are incorporated herein by reference.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Therefore, there is need for new tetracycline analogs with improved antibacterial activities and efficacies against other tetracycline responsive diseases or disorders.

SUMMARY OF THE INVENTION

The present invention is directed to a compound represented by Structural Formula (A):

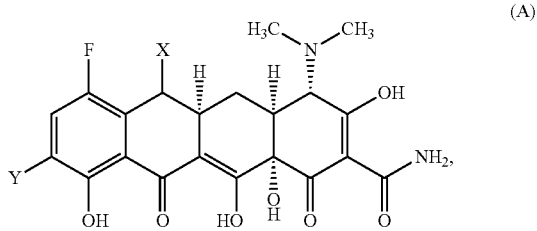

(A)

or a pharmaceutically acceptable salt thereof, wherein:

X is selected from hydrogen, —($C_1$-$C_7$)alkyl, carbocyclyl, aryl and heteroaryl;

Y is selected from hydrogen, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl;

at least one of X and Y is not hydrogen;

each $R^A$ and $R^B$ are independently selected from hydrogen, ($C_1$-$C_7$)alkyl, —O—($C_1$-$C_7$)alkyl, —($C_0$-$C_6$)alkylene-carbocyclyl, —($C_0$-$C_6$)alkylene-aryl, —($C_0$-$C_6$)alkylene-heterocyclyl, —($C_0$-$C_6$)alkylene-heteroaryl, —($C_1$-$C_6$)alkylene-O-carbocyclyl, —($C_1$-$C_6$)alkylene-O-aryl, —($C_1$-$C_6$)alkylene-O-heterocyclyl, —($C_1$-$C_6$)alkylene-O-heteroaryl, —S(O)$_m$—($C_1$-$C_6$)alkyl, —($C_0$-$C_4$)alkylene-S(O)$_m$-carbocyclyl, —($C_0$-$C_4$)alkylene-S(O)$_m$-aryl, —($C_0$-$C_4$)alkylene-S(O)$_m$-heterocyclyl and —($C_0$-$C_4$)alkylene-S(O)$_m$-heteroaryl; or $R^A$ and $R^B$ taken together with the nitrogen atom to which they are bound form a heterocyclyl or heteroaryl, wherein the heterocycle or heteroaryl optionally comprises 1 to 4 additional heteroatoms independently selected from N, S and O;

each $R^D$ and each $R^E$ is independently selected from hydrogen, ($C_1$-$C_6$)alkyl, carbocyclyl, aryl, heterocyclyl, heteroaryl, or a naturally occurring amino acid side chain moiety, or $R^D$ and $R^E$ taken together with the carbon atom to which they are bound form a 3-7 membered carbocyclyl, or a 4-7 membered heterocyclyl, wherein the heterocyclyl formed by $R^D$ and $R^E$ optionally comprises one to two additional heteroatoms independently selected from N, S and O;

$R^F$ is selected from hydrogen, ($C_1$-$C_7$)alkyl, carbocyclyl, aryl and heteroaryl; and m is 1 or 2, wherein:

each carbocyclyl, aryl, heterocyclyl or heteroaryl is optionally and independently substituted with one or more substituents independently selected from halo, —($C_1$-$C_4$)alkyl, —OH, =O, —O—($C_1$-$C_4$)alkyl, —($C_1$-$C_4$)alkyl-O—($C_1$-$C_4$)alkyl, halo-substituted —($C_1$-$C_4$)alkyl, halo-substituted —O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N($R^G$)($R^G$), and CN;

each alkyl in the group represented by $R^A$, $R^B$, $R^D$ and $R^E$ is optionally and independently substituted with one or more substituents independently selected from halo, —($C_1$-$C_4$)alkyl, —OH, —O—($C_1$-$C_7$)alkyl, —($C_1$-$C_4$)alkyl-O—($C_1$-$C_4$)alkyl, fluoro-substituted-($C_1$-$C_4$)alkyl, —S(O)$_m$—($C_1$-$C_4$)alkyl, and —N($R^G$)($R^G$), wherein each $R^G$ is hydrogen or ($C_1$-$C_4$)alkyl, wherein each alkyl in the group represented by $R^G$ is optionally and independently substituted with one or more substituents independently selected from —($C_1$-$C_4$)alkyl, ($C_3$-$C_6$)cycloalkyl, halo, —OH, —O—($C_1$-$C_4$)alkyl, and ($C_1$-$C_4$)alkyl-O—($C_1$-$C_4$)alkyl.

Another embodiment of the present invention is directed to a compound represented by Structural Formula (II)

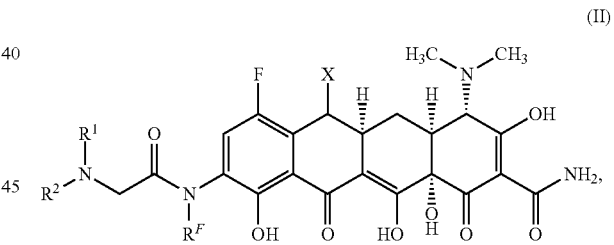

(II)

or a pharmaceutically acceptable salt thereof, wherein:

$R^1$ and $R^2$ are each independently selected from hydrogen, ($C_1$-$C_7$)alkyl, ($C_3$-$C_6$)cycloalkyl($C_1$-$C_4$)alkyl, ($C_1$-$C_7$)alkoxy($C_1$-$C_4$)alkyl, ($C_3$-$C_6$)cycloalkoxy($C_1$-$C_4$)alkyl, ($C_3$-$C_6$)cycloalkyl, aryl, aryl($C_1$-$C_4$)alkyl, aryloxy($C_1$-$C_4$)alkyl, arylthio($C_1$-$C_4$)alkyl, arylsufinyl($C_1$-$C_4$)alkyl, arylsulfonyl ($C_1$-$C_4$)alkyl, and —O—($C_1$-$C_7$)alkyl, or $R^1$ and $R^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one or two additional heteroatoms independently selected from N, O and S; and wherein each alkyl, cycloalkyl, alkoxy and cycloalkoxy moiety in the groups represented by $R^1$ and $R^2$ and each heterocycle represented by NR$^1$R$^2$ taken together is optionally substituted with one or more substituents independently selected from the group consisting of ($C_1$-$C_4$)alkyl, halo, —OH, $(C_1\text{-}C_4)$alkoxy, $(C_1\text{-}C_4)$alkylthio, $(C_1\text{-}C_4)$alkylsulfinyl, $(C_1\text{-}C_4)$alkylsulfonyl, $(C_1\text{-}C_4)$alkoxy$(C_1\text{-}C_4)$alkyl, and —N(R$^3$)(R$^4$); and each aryl, aryloxy, arylthio, arylsufinyl and arylsulfonyl moiety in the groups represented by R$^1$ and R$^2$ and each heteroaryl represented by NR$^1$R$^2$ taken together is optionally substituted with one or more substituents independently selected from the group consisting of $(C_1\text{-}C_4)$alkyl, halo, —OH, $(C_1\text{-}C_4)$alkoxy, —S—$(C_1\text{-}C_4)$alkyl, —S(O)$(C_1\text{-}C_4)$alkyl, —S(O)$_2$$(C_1\text{-}C_4)$alkyl, $(C_1\text{-}C_4)$alkoxy$(C_1\text{-}C_4)$alkyl, —N(R$^3$)(R$^4$); —CN, halo$(C_1\text{-}C_4)$alkyl, and halo$(C_1\text{-}C_4)$alkoxy, and R$^3$ and R$^4$ are each independently selected from the group consisting of —H and $(C_1\text{-}C_4)$alkyl, wherein the $(C_1\text{-}C_4)$alkyl represented by R$^3$ and R$^4$ is optionally substituted with one or more substituents independently selected from the group consisting of $(C_1\text{-}C_4)$alkyl, halo, —OH, $(C_1\text{-}C_4)$alkoxy, and $(C_1\text{-}C_4)$alkoxy$(C_1\text{-}C_4)$alkyl. Values for X and R$^F$ are as described above for Structural Formula (A).

Another embodiment of the present invention is directed to a compound represented by Structural Formula (I):

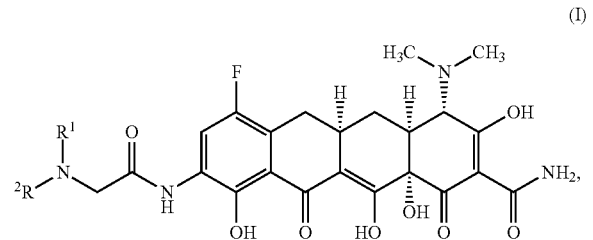

(I)

or a pharmaceutically acceptable salt thereof, wherein:

R$^1$ and R$^2$ are each independently selected from hydrogen, $(C_1\text{-}C_7)$alkyl, $(C_3\text{-}C_6)$cycloalkyl$(C_1\text{-}C_4)$alkyl, $(C_1\text{-}C_7)$alkoxy$(C_1\text{-}C_4)$alkyl, $(C_3\text{-}C_6)$cycloalkoxy$(C_1\text{-}C_4)$alkyl, $(C_3\text{-}C_6)$cycloalkyl, aryl, aryl$(C_1\text{-}C_4)$alkyl, aryloxy$(C_1\text{-}C_4)$alkyl, arylthio$(C_1\text{-}C_4)$alkyl, arylsulfinyl$(C_1\text{-}C_4)$alkyl, and arylsulfonyl$(C_1\text{-}C_4)$alkyl, or R$^1$ and R$^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one additional heteroatom independently selected from N, O and S; and the remainder of the variables are as described above for Structural Formula (II).

Another embodiment of the present invention is directed to a pharmaceutical composition comprising a pharmaceutically acceptable carrier or diluent and a compound represented by Structural Formula (A), (II) or (I) or a pharmaceutically acceptable salt thereof. The pharmaceutical composition is used in therapy, such as treating an infection in a subject.

Another embodiment of the present invention is a method of treating an infection in a subject comprising administering to the subject an effective amount of a compound represented by Structural Formula (A), (II) or (I) or a pharmaceutically acceptable salt thereof.

Another embodiment of the present invention is a method of preventing an infection in a subject comprising administering to the subject an effective amount of a compound represented by Structural Formula (A), (II) or (I) or a pharmaceutically acceptable salt thereof.

Another embodiment of the present invention is the use of a compound represented by Structural Formula (A), (II) or (I) or a pharmaceutically acceptable salt thereof for the manufacture of a medicament for treating an infection in a subject.

Another embodiment of the present invention is the use of a compound represented by Structural Formula (A), (II) or (I) or a pharmaceutically acceptable salt thereof for the manufacture of a medicament for preventing an infection in a subject.

Another embodiment of the present invention is the use of a compound represented by Structural Formula (A), (II) or (I) or a pharmaceutically acceptable salt thereof for therapy, such as treating or preventing an infection in a subject.

DETAILED DESCRIPTION OF THE INVENTION

The present invention is directed to a compound represented by Structural Formula (A) or a pharmaceutically acceptable salt thereof. Values and alternative values for the variables in Structural Formula (A) are defined as the following:

X is selected from hydrogen, —$(C_1\text{-}C_7)$alkyl, carbocyclyl, aryl and heteroaryl. In one embodiment, X is hydrogen. In an alternative embodiment, X is —$(C_1\text{-}C_7)$alkyl. Alternatively, X is —$(C_1\text{-}C_4)$alkyl. In another embodiment, X is carbocyclyl. In another alternative embodiment, X is aryl or heteroaryl. In another alternative embodiment, X is phenyl.

Y is selected from hydrogen, —$(C_1\text{-}C_7)$alkyl, carbocyclyl, —$(C_1\text{-}C_4)$alkylene-N(R$^A$)(R$^B$), —$(C_1\text{-}C_4)$alkylene-N(R$^F$)—C(O)—[C(R$^D$)(R$^E$)]$_{0\text{-}4}$—N(R$^A$)(R$^B$), —CH=N—OR$^A$, —N(R$^A$)(R$^B$), —N(R$^F$)—C(O)—[C(R$^D$)(R$^E$)]$_{1\text{-}4}$—N(R$^A$)(R$^B$), —N(R$^F$)—C(O)—N(R$^A$)(R$^B$), —N(R$^F$)—C(O)—$(C_1\text{-}C_6)$alkyl, —N(R$^F$)—C(O)-heterocyclyl, —N(R$^F$)—C(O)-heteroaryl, —N(R$^F$)—C(O)-carbocyclyl, —N(R$^F$)—C(O)-aryl, —N(R$^F$)—S(O)$_m$—$(C_1\text{-}C_4)$alkylene-N(R$^A$)(R$^B$), —N(R$^F$)—S(O)$_6$, —$(C_1\text{-}C_4)$alkylene-carbocyclyl, and —N(R$^F$)—S(O)$_m$—$(C_1\text{-}C_4)$alkylene-aryl, provided at least one of X and Y is not hydrogen. In one embodiment, Y is selected from hydrogen, —$(C_1\text{-}C_7)$alkyl, —$(C_1\text{-}C_4)$alkylene-N(R$^A$)(R$^B$), —$(C_1\text{-}C_4)$alkylene-N(R$^F$)—C(O)—[C(R$^D$)(R$^E$)]$_{0\text{-}4}$—N(R$^A$)(R$^B$), —CH=N—OR$^A$, —N(R$^A$)(R$^B$), —N(R$^F$)—C(O)—[C(R$^D$)(R$^E$)]$_{1\text{-}4}$—N(R$^A$)(R$^B$), —N(R$^F$)—C(O)—N(R$^A$)(R$^B$), —N(R$^F$)—C(O)—$(C_1\text{-}C_6)$alkyl, —N(R$^F$)—C(O)-heterocyclyl, —N(R$^F$)—C(O)-heteroaryl, —N(R$^F$)—C(O)-carbocyclyl, —N(R$^F$)—C(O)-aryl, —N(R$^F$)—S(O)$_m$—$(C_1\text{-}C_4)$alkylene-N(R$^A$)(R$^B$), —N(R$^F$)—S(O), —$(C_1\text{-}C_4)$alkylene-carbocyclyl, and —N(R$^F$)—S(O)$_m$—$(C_1\text{-}C_4)$alkylene-aryl, provided at least one of X and Y is not hydrogen. In one embodiment, Y is selected from hydrogen, —$(C_1\text{-}C_7)$alkyl, —$(C_1\text{-}C_4)$alkylene-N(R$^A$)(R$^B$), —$(C_1\text{-}C_4)$alkylene-N(R$^F$)—C(O)—[C(R$^D$)(R$^E$)]$_{0\text{-}4}$—N(R$^A$)(R$^B$), —CH=N—OR$^A$, —N(R$^A$)(R$^B$), —N(R$^F$)—C(O)—[C(R$^D$)(R$^E$)]$_{1\text{-}4}$—N(R$^A$)(R$^B$), —NH—C(O)—C(R$^{D'}$)(R$^E$)—N(R$^A$)(R$^B$), —N(R$^F$)—C(O)—N(R$^A$)(R$^B$), —N(R$^F$)—C(O)—$(C_1\text{-}C_6)$alkyl, —N(R$^F$)—C(O)-heterocyclyl, —N(R$^F$)—C(O)-heteroaryl, —N(R$^F$)—C(O)-carbocyclyl, —N(R$^F$)—C(O)-aryl —N(R$^F$)—S(O)$_m$—$(C_1\text{-}C_4)$alkylene-N(R$^A$)(R$^B$), —N(R$^F$)—S(O)$_m$—$(C_1\text{-}C_4)$alkylene-carbocyclyl, and —N(R$^F$)—S(O)$_m$—$(C_1\text{-}C_4)$alkylene-aryl. In another embodiment, Y is selected from hydrogen, —$(C_1\text{-}C_7)$alkyl, —$(C_1\text{-}C_4)$alkylene-N(R$^A$)(R$^B$), —$(C_1\text{-}C_4)$alkylene-NH—C(O)—(CH$_2$)$_{0\text{-}1}$—N(R$^A$)(R$^B$), —N(R$^A$)(R$^B$), —NH—C(O)-carbocyclyl, —NH—C(O)-aryl, —NH—C(O)-heterocyclyl, —NH—C(O)-heteroaryl, —NH—C(O)—N(R$^A$)(R$^A$), —N(R$^{F'}$)—C(O)—CH$_2$—N(R$^A$)(R$^B$), —NH—C(O)—C(R$^{D'}$)(R$^E$)—N(R$^A$)(R$^B$) and —NH—S(O)$_m$—$(C_1\text{-}C_4)$alkylene-N(R$^A$)(R$^B$). Alternatively, the —$(C_1\text{-}C_7)$alkyl represented by Y described above is a —$(C_1\text{-}C_4)$alkyl. In yet another embodiment, Y is selected from —N(R$^A$)(R$^B$), —N(H)—C(O)-carbocyclyl, —N(H)—C(O)-aryl, —N(H)—C(O)-heterocycle, and —N(H)—C(O)-heteroaryl. Alternatively, Y is —NH—C(O)—CH$_2$—N(R$^A$)(R$^B$). More specifically, R$^A$ and R$^B$ in —NH—C(O)—CH$_2$—N(R$^A$)(R$^B$) are R$^1$ and R$^2$, respectively.

Each R$^A$ and R$^B$ are independently selected from hydrogen, (C$_1$-C$_7$)alkyl, —O—(C$_1$-C$_7$)alkyl, —(C$_0$-C$_6$)alkylene-carbocyclyl, —(C$_0$-C$_6$)alkylene-aryl, —(C$_0$-C$_6$)alkylene-heterocyclyl, —(C$_0$-C$_6$)alkylene-heteroaryl, —(C$_1$-C$_6$)alkylene-O-carbocyclyl, —(C$_1$-C$_6$)alkylene-O-aryl, —(C$_1$-C$_6$)alkylene-O-heterocyclyl, —(C$_1$-C$_6$)alkylene-O-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocyclyl and —(C$_0$-C$_4$)alkylene-S(O)$_m$-heteroaryl; or R$^A$ and R$^B$ taken together with the nitrogen atom to which they are bound form a heterocyclyl or heteroaryl, wherein the heterocycle or heteroaryl optionally comprises 1 to 4 additional heteroatoms independently selected from N, S and O. In one embodiment, each R$^A$ is independently selected from hydrogen and methyl; R$^B$ is selected from hydrogen, (C$_1$-C$_7$)alkyl, —(C$_0$-C$_6$)alkylene-carbocyclyl, —(C$_0$-C$_6$)alkylene-aryl, —(C$_0$-C$_6$)alkylene-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocycle and —(C$_0$-C$_4$)alkylene-S(O)$_m$-heteroaryl; or R$^A$ and R$^B$ taken together with the nitrogen atom to form a heterocycle, wherein the heterocycle is optionally substituted with =O and —N(R$^G$)(R$^G$). In another embodiment, R$^A$ is hydrogen; and R$^B$ is selected from (C$_1$-C$_4$)alkyl, and —S(O)$_2$—CH$_3$; or R$^A$ and R$^B$ taken together to form 4-7 membered heterocyclic ring.

Each R$^D$ and each R$^E$ is independently selected from hydrogen, (C$_1$-C$_6$)alkyl, carbocyclyl, aryl, heterocyclyl, heteroaryl, or a naturally occurring amino acid side chain moiety, or R$^D$ and R$^E$ taken together with the carbon atom to which they are bound form a 3-7 membered carbocyclyl, or a 4-7 membered heterocyclyl, wherein the heterocyclyl formed by R$^D$ and R$^E$ optionally comprises one to two additional heteroatoms independently selected from N, S and O. In one embodiment, R$^D$ and R$^E$ are both —H.

R$^F$ is selected from hydrogen, (C$_1$-C$_7$)alkyl, carbocyclyl, aryl and heteroaryl. In one embodiment, R$^F$ is hydrogen. In another embodiment, R$^F$ is selected from hydrogen, (C$_1$-C$_7$)alkyl, aryl and heteroaryl. In another embodiment, R$^F$ is selected from hydrogen, (C$_1$-C$_7$)alkyl and phenyl. In another embodiment, R$^F$ is selected from hydrogen, (C$_1$-C$_4$)alkyl and phenyl R$^{D'}$ is selected from (C$_1$-C$_6$)alkyl, carbocyclyl, aryl, heteroaryl, heterocyclyl, and a naturally occurring amino acid side chain moiety, or R$^{D'}$ and R$^E$ taken together with the carbon atom to which they are bound form a 3-7 membered carbocyclyl, or a 4-7 membered heterocyclyl, wherein the heterocyclyl formed by R$^{D'}$ and R$^E$ optionally comprises one to two additional heteroatoms independently selected from N, S and O. In one embodiment, R$^{D'}$ and R$^E$ taken together with the carbon atom to which they are bound form a (C$_3$-C$_7$) cycloalkyl.

m is 1 or 2. In one embodiment, m is 2.

Each carbocyclyl, aryl, heterocyclyl or heteroaryl described above (e.g., in the groups represented by Y, R$^A$, R$^B$, R$^D$, R$^{D'}$ and R$^E$)) is optionally and independently substituted with one or more substituents independently selected from halo, —(C$_1$-C$_4$)alkyl, —OH, =O, —O—(C$_1$-C$_4$)alkyl, —(C$_1$-C$_4$)alkyl-O—(C$_1$-C$_4$)alkyl, halo-substituted —(C$_1$-C$_4$)alkyl, halo-substituted —O—(C$_1$-C$_4$)alkyl, —C(O)—(C$_1$-C$_4$)alkyl, —C(O)-(fluoro-substituted-(C$_1$-C$_4$)alkyl), —S(O)$_m$—C$_1$-C$_4$)alkyl, —N(R$^G$)(R$^G$), and CN. In one embodiment, each carbocyclyl, heterocyclyl or heteroaryl is optionally and independently substituted with one or more substituents independently selected from halo, —(C$_1$-C$_4$)alkyl, halo-substituted —(C$_1$-C$_4$)alkyl, —O—(C$_1$-C$_4$)alkyl, and —N(R$^G$)(R$^G$). In another embodiment, each carbocyclyl, aryl, heteroaryl, or heterocycle is optionally and independently substituted with one or more substituents independently selected from —CH$_3$, fluoro, and —N(CH$_3$)$_2$.

Each alkyl described above (e.g., in the groups represented by Y, R$^A$, R$^B$, R$^D$, R$^{D'}$, R$^E$, R$^F$ and R$^{F'}$) is optionally and independently substituted with one or more substituents independently selected from halo, —(C$_1$-C$_4$)alkyl, —OH, —O—(C$_1$-C$_7$)alkyl, —(C$_1$-C$_4$)alkyl-O—(C$_1$-C$_4$)alkyl, fluoro-substituted-(C$_1$-C$_4$)alkyl, —S(O)$_m$—(C$_1$-C$_4$)alkyl, and —N(R$^G$)(R$^G$). In one embodiment, each alkyl group (e.g., in the group represented by Y or R$^B$) is optionally and independently substituted with one or more substituents independently selected from halo, —OH, and —N(R$^G$)(R$^G$).

Each R$^G$ is hydrogen or (C$_1$-C$_4$)alkyl, wherein each alkyl in the group represented by R$^G$ is optionally and independently substituted with one or more substituents independently selected from —(C$_1$-C$_4$)alkyl, (C$_3$-C$_6$)cycloalkyl, halo, —OH, —O—(C$_1$-C$_4$)alkyl, and (C$_1$-C$_4$)alkyl-O—(C$_1$-C$_4$)alkyl. In one embodiment, each alkyl in the group represented by R$^G$ is optionally and independently substitued with (C$_3$-C$_6$)cycloalkyl.

As used herein, when R$^A$ and R$^B$ taken together with the nitrogen atom to which they are bound form a a heterocyclyl or heteroaryl, the heterocyclyl or heteroaryl represented by —NR$^A$R$^B$ can include a ring system that has a heteroatom adjacent to the nitrogen atom to which R$^A$ and R$^B$ are bound. For example, —NR$^A$R$^B$ can be, but is not limited to, the following ring systems:

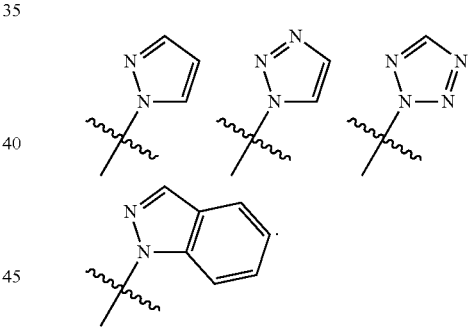

Similarly, when R$^D$ and R$^E$ or R$^{D'}$ and R$^E$ taken together with the carbon atom to which they are bound form a heterocyclyl, the heterocyclyl can include a ring system that has a heteroatom adjacent to the carbon atom to which R$^D$ and R$^E$ or R$^{D'}$ and R$^E$ are bound.

The present invention is directed to a compound represented by Structural Formula (I) or (II) or a pharmaceutically acceptable salt thereof. Values and alternative values for the variables in Structural Formula (I) or (II) are defined as the following:

R$^1$ is selected from hydrogen, (C$_1$-C$_7$)alkyl, (C$_3$-C$_6$)cycloalkyl(C$_1$-C$_4$)alkyl, (C$_1$-C$_7$)alkoxy(C$_1$-C$_4$)alkyl, (C$_3$-C$_6$)cycloalkoxy(C$_1$-C$_4$)alkyl, (C$_3$-C$_6$)cycloalkyl, aryl, aryl(C$_1$-C$_4$)alkyl, aryloxy(C$_1$-C$_4$)alkyl, arylthio(C$_1$-C$_4$)alkyl, arylsulfinyl(C$_1$-C$_4$)alkyl, arylsulfonyl(C$_1$-C$_4$)alkyl and —O—(C$_1$-C$_7$)alkyl. Each alkyl, cycloalkyl, alkoxy, cycloalkoxy, aryl, aryloxy, arylthio, arylsulfinyl and arylsulfonyl moiety in the groups represented by R$^1$ can be optionally substituted with one or more independently selected substituents defined above for Structural Formula (I). Alternatively, $R^1$ is selected from hydrogen, $(C_1-C_7)$alkyl, $(C_3-C_6)$cycloalkyl$(C_1-C_4)$alkyl, $(C_1-C_7)$alkoxy$(C_1-C_4)$alkyl, $(C_3-C_6)$cycloalkoxy$(C_1-C_4)$alkyl, $(C_3-C_6)$cycloalkyl, aryl, aryl$(C_1-C_4)$alkyl, aryloxy$(C_1-C_4)$alkyl, arylthio$(C_1-C_4)$alkyl, arylsulfinyl$(C_1-C_4)$alkyl and arylsulfonyl$(C_1-C_4)$alkyl. In another alternative, $R^1$ is —H, $(C_1-C_7)$alkyl, or —O—$(C_1-C_4)$alkyl. In another alternative, $R^1$ is —H or $(C_1-C_7)$alkyl. In another alternative, $R^1$ is —H, methyl or ethyl. In yet another alternative, $R^1$ is —OCH$_3$ or —OC(CH$_3$)$_3$.

$R^2$ is selected from hydrogen, $(C_1-C_7)$alkyl, $(C_3-C_6)$cycloalkyl$(C_1-C_4)$alkyl, $(C_1-C_7)$alkoxy$(C_1-C_4)$alkyl, $(C_3-C_6)$cycloalkoxy$(C_1-C_4)$alkyl, $(C_3-C_6)$cycloalkyl, aryl, aryl$(C_1-C_4)$alkyl, aryloxy$(C_1-C_4)$alkyl, arylthio$(C_1-C_4)$alkyl, arylsulfinyl$(C_1-C_4)$alkyl, arylsulfonyl$(C_1-C_4)$alkyl and —O—$(C_1-C_7)$alkyl. Each alkyl, cycloalkyl, alkoxy, cycloalkoxy, aryl, and aryloxy moiety in the groups represented by $R^2$ can be optionally substituted with one or more independently selected substituents defined above for Structural Formula (I). Alternatively, $R^2$ is selected from hydrogen, $(C_1-C_7)$alkyl, $(C_3-C_6)$cycloalkyl$(C_1-C_4)$alkyl, $(C_1-C_7)$alkoxy$(C_1-C_4)$alkyl, $(C_3-C_6)$cycloalkoxy$(C_1-C_4)$alkyl, $(C_3-C_6)$cycloalkyl, aryl, aryl$(C_1-C_4)$alkyl, aryloxy$(C_1-C_4)$alkyl, arylthio$(C_1-C_4)$alkyl, arylsulfinyl$(C_1-C_4)$alkyl and arylsulfonyl$(C_1-C_4)$alkyl. Alternatively, $R^2$ is selected from $(C_1-C_7)$alkyl, $(C_3-C_6)$cycloalkyl$(C_1-C_4)$alkyl, $(C_1-C_7)$alkoxy$(C_1-C_4)$alkyl, phenyl, phenyl$(C_1-C_4)$alkyl, $(C_3-C_6)$cycloalkyl and halo$(C_1-C_4)$alkyl, wherein each alkyl, alkoxy and cycloalkyl moiety in the groups represented by $R^2$ is optionally substituted with one or more substituents independently selected from the group consisting of $(C_1-C_4)$alkyl and halo; and each phenyl moiety in the groups represented by $R^2$ is optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy. In another alternative, $R^2$ is selected from the group consisting of cyclopropyl, cyclobutyl, cyclopentyl, cyclopropylmethyl, cyclobutylmethyl, phenyl, benzyl, —(CH$_2$)$_2$—O—CH$_3$, —(CH$_2$)$_3$—OCH$_3$, —C(CH$_3$)$_3$, —CH(CH$_3$)$_2$, —CH$_2$C(CH$_3$)$_3$, —CH$_2$CH(CH$_3$)$_2$, —CH$_2$—CF$_3$, —(CH$_2$)$_2$—CH$_2$F, and —(CH$_2$)$_n$CH$_3$, wherein n is 0, 1, 2, 3, 4, 5 or 6; and wherein the phenyl or benzyl group represented by $R^2$ is optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy. In another alternative, $R^2$ is a phenyl or benzyl group optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy. In another alternative, $R^2$ is unsubstituted phenyl or benzyl. In another alternative, $R^2$ is selected from cyclopropyl, cyclopropylmethyl, cyclobutyl, cyclopentyl, cyclohexyl, —(CH$_2$)$_2$—O—CH$_3$, —C(CH$_3$)$_3$, —CH(CH$_3$)$_2$, —CH$_2$—CF$_3$, —CH$_2$CH(CH$_3$)$_2$, —CH$_3$ and —CH$_2$CH$_3$.

Alternatively, $R^1$ and $R^2$ taken together with the nitrogen atom to which they are bonded can also form a monocyclic or bicyclic heteroaryl, or a monocyclic, fused bicyclic, bridged bicyclic or spiro bicyclic heterocycle, wherein the heteroaryl or heterocycle optionally contains one or two additional heteroatoms independently selected from N, O and S in addition to the N atom to which R$_1$ and R$_2$ are bonded. The heteroaryl or heterocycle can be optionally substituted with one or more independently selected substituents described above for Structural Formula (I). Alternatively, the heteroaryl or heterocycle contains one additional heteroatom selected from N, O and S. Alternatively, $R^1$ and $R^2$ taken together with the nitrogen atom to which they are bonded form a heterocycle selected from the group consisting of azetidine, pyrrolidine, morpholine, piperidine, octahydrocyclopenta[c]pyrrol, isoindoline, and azabicyclo[3.1.0]hexane, wherein the heterocycle is optionally substituted with one or more substituents independently selected from the group consisting of $(C_1-C_4)$alkyl, halogen, —OH, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkoxy$(C_1-C_4)$alkyl, and —N(R$^3$)(R$^4$). In a more specific embodiment, these heterocycles are optionally substituted with one or more substituents independently selected from the group consisting of halogen, $(C_1-C_4)$alkoxy, hydroxy, $(C_1-C_4)$alkoxy$(C_1-C_4)$alkyl and —N(R$^3$)(R$^4$). In another alternative embodiment, these heterocycles are optionally substituted with one or more substituents independently selected from the group consisting of halogen, methoxy, hydroxy, methoxymethyl and dimethylamino. Alternatively, $R^1$ and $R^2$ taken together with the nitrogen atom to which they are bonded form a ring selected from pyrrolidinyl, morpholinyl, azetidinyl, piperidinyl, octahydrocyclopenta[c]pyrrolyl, isoindolinyl, indazolyl, imidazolyl, pyrazolyl, triazolyl, and tetrazolyl, wherein the ring formed by $R^1$ and $R^2$ taken together with the nitrogen atom to which they are bonded is optionally substituted with halogen, $(C_1-C_4)$alkoxy, hydroxy, $(C_1-C_4)$alkoxy$(C_1-C_4)$alkyl and —N(R$^3$)(R$^4$). More specifically, the ring formed by $R^1$ and $R^2$ taken together with the nitrogen atom to which they are bonded is optionally substituted with fluoro, —OH, —OCH$_3$, or N(CH$_3$)$_2$.

$R^3$ and $R^4$ are each independently selected from the group consisting of —H and $(C_1-C_4)$alkyl, wherein the $(C_1-C_4)$alkyl represented by $R^3$ and $R^4$ is optionally substituted with one or more substituents independently selected from the group consisting of $(C_1-C_4)$alkyl, halo, —OH, $(C_1-C_4)$alkoxy, and $(C_1-C_4)$alkoxy$(C_1-C_4)$alkyl. Alternatively, $R^3$ and $R^4$ are both methyl. In another alternative, $R^3$ and $R^4$ are both —H. In yet another alternative, $R^3$ and $R^4$ are each unsubstituted $(C_1-C_4)$alkyl.

In a first alternative embodiment, the compound of the present invention is represented by Structural Formula (I) or (II), or a pharmaceutically acceptable salt thereof, wherein:

$R^1$ is —H or $(C_1-C_7)$alkyl; and $R^2$ is selected from $(C_1-C_7)$alkyl, $(C_3-C_6)$cycloalkyl$(C_1-C_4)$alkyl, $(C_1-C_7)$alkoxy$(C_1-C_4)$alkyl, phenyl, phenyl$(C_1-C_4)$alkyl, $(C_3-C_6)$cycloalkyl and halo$(C_1-C_4)$alkyl, wherein each alkyl, alkoxy or cycloalkyl moiety in the groups represented by $R^2$ is optionally substituted with one or more substituents independently selected from the group consisting of $(C_1-C_4)$alkyl and halo; and each phenyl moiety in the groups represented by $R^2$ is optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy. Alternatively, $R^2$ is selected from the group consisting of cyclopropyl, cyclobutyl, cyclopentyl, cyclopropylmethyl, cyclobutylmethyl, phenyl, benzyl, —(CH$_2$)$_2$—O—CH$_3$, —(CH$_2$)$_3$—OCH$_3$, —C(CH$_3$)$_3$, —CH(CH$_3$)$_2$, —CH$_2$C(CH$_3$)$_3$, —CH$_2$CH(CH$_3$)$_2$, —CH$_2$—CF$_3$, —(CH$_2$)$_2$—CH$_2$F, and —(CH$_2$)$_n$CH$_3$, wherein n is 0, 1, 2, 3, 4, 5 or 6; and wherein the phenyl or benzyl group represented by $R^2$ is optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy. In another alternative, the phenyl or benzyl group represented by $R^2$ is unsubstituted. In yet another alternative, $R^2$ is selected from cyclopropyl, cyclopropylmethyl, cyclobutyl, cyclopentyl, cyclohexyl, —(CH$_2$)$_2$—O—CH$_3$, —C(CH$_3$)$_3$, —CH(CH$_3$)$_2$, —CH$_2$—CF$_3$, —CH$_2$CH(CH$_3$)$_2$, —CH$_3$ and —CH$_2$CH$_3$.

In a second alternative embodiment, for compounds represented by Structural Formula (I) or (II), R$^1$ is hydrogen, methyl or ethyl; and values and alternative values for R$^2$ are as described above for the first alternative embodiment.

In a third alternative embodiment, for compounds represented by Structural Formula (I) or (II), R$^1$ is hydrogen, (C$_1$-C$_4$)alkyl or —O—(C$_1$-C$_4$)alkyl; R$^2$ is selected from (C$_1$-C$_7$) alkyl, (C$_3$-C$_6$)cycloalkyl(C$_1$-C$_4$)alkyl, (C$_1$-C$_7$)alkoxy(C$_1$-C$_4$)alkyl, phenyl, (C$_3$-C$_6$)cycloalkyl, and fluoro(C$_1$-C$_4$)alkyl; or R$^1$ and R$^2$ taken together with the nitrogen atom to which they are bonded form a ring selected from pyrrolidinyl, morpholinyl, azetidinyl, piperidinyl, octahydrocyclopenta[c]pyrrolyl, isoindolinyl, indazolyl, imidazolyl, pyrazolyl, triazolyl, and tetrazolyl, wherein the ring formed by R$^1$ and R$^2$ taken together with the nitrogen atom to which they are bonded is optionally substituted with fluoro, —OH, —OCH$_3$, or N(CH$_3$)$_2$. More specifically, R$^1$ is hydrogen, methyl, ethyl, methoxy or tert-butoxy.

In a fourth alternative embodiment, for compounds represented by Structural Formula (I) or (II), R$^1$ hydrogen, methyl, or ethyl; R$^2$ is selected from methyl, ethyl, n-propyl, isopropyl, n-butyl, 2,2-dimethylpropyl, t-butyl, isobutyl, n-pentyl, (C$_4$-C$_6$)cycloalkyl, (C$_3$-C$_5$)cycloalkylmethyl, methoxyethyl, and 2-fluoroethyl; or R$^1$ and R$^2$ taken together with the nitrogen atom to which they are bonded form a ring selected from azetidinyl, pyrrolidinyl, piperidinyl, tetrazolyl, or octahydrocyclopenta[c]pyrrolyl, and wherein the ring formed by R$^1$ and R$^2$ taken together with the nitrogen atom to which they are bonded is optionally substituted with fluoro.

In a fifth alternative embodiment, for compounds represented by Structural Formula (A), when X is hydrogen, Y is selected from hydrogen, —(C$_1$-C$_4$)alkyl, —(C$_1$-C$_4$)alkylene-N(R$^A$)(R$^B$), —(C$_1$-C$_4$)alkylene-N(R$^F$)—C(O)—[C(R$^D$)(R$^E$)]$_{0-4}$—N(R$^A$)(R$^B$), —CH═N—OR$^A$, —N(R$^A$)(R$^B$), —N(R$^{F'}$)—C(O)—[C(R$^D$)(R$^E$)]$_{1-4}$—N(R$^A$)(R$^B$), —NH—C(O)—C(R$^{D'}$)(R$^E$)—N(R$^A$)(R$^B$), —N(R$^F$)—C(O)—N(R$^A$)(R$^A$), —N(R$^F$)—C(O)—(C$_1$-C$_6$)alkyl, —N(R$^F$)—C(O)-heterocyclyl, —N(R$^F$)—C(O)-heteroaryl, —N(R$^F$)—C(O)-carbocyclyl, —N(R$^F$)—C(O)-aryl —N(R$^F$)—S(O)$_m$—(C$_1$-C$_4$)alkylene-N(R$^A$)(R$^B$), —N(R$^F$)—S(O)$_m$—(C$_1$-C$_4$)alkylene-carbocyclyl, —N(R$^F$)—S(O)$_m$—(C$_1$-C$_4$)alkylene-aryl;

R$^{D'}$ is selected from (C$_1$-C$_6$)alkyl, carbocyclyl, aryl, heteroaryl, heterocyclyl, and a naturally occurring amino acid side chain moiety, or R$^{D'}$ and R$^E$ taken together with the carbon atom to which they are bound form a 3-7 membered carbocyclyl, or a 4-7 membered heterocyclyl, wherein the heterocyclyl formed by R$^{D'}$ and R$^E$ optionally comprises one to two additional heteroatoms independently selected from N, S and O; and R$^{F'}$ is selected from (C$_1$-C$_7$)alkyl, carbocyclyl, aryl and heteroaryl. Values and alternative values for the remainder of the variables are as described above for Structural Formula (A). Alternatively, R$^{F'}$ is selected from (C$_1$-C$_4$)alkyl and phenyl and the remainder of the variables are as described above in the fifth alternative embodiment.

In a sixth alternative embodiment, for compounds represented by Structural Formula (A), X is selected from hydrogen, methyl, ethyl and phenyl; and Y is selected from hydrogen, —(C$_1$-C$_4$ alkyl), —(C$_1$-C$_4$)alkylene-N(R$^A$)(R$^B$), —(C$_1$-C$_4$)alkylene-NH—C(O)—[CH$_2$]$_{0-1}$—N(R$^A$)(R$^B$), —N(R$^A$)(R$^B$), —NH—C(O)-carbocyclyl, —NH—C(O)-aryl, —NH—C(O)-heterocyclyl, —NH—C(O)-heteroaryl, —NH—C(O)—N(R$^A$)(R$^A$), —N(R$^F$)—C(O)—CH$_2$—N(R$^A$)(R$^B$), —NH—C(O)—C(R$^D$)(R$^E$)—N(R$^A$)(R$^B$) and —NH—S(O)$_m$—(C$_1$-C$_4$)alkylene-N(R$^A$)(R$^B$); or X is selected from methyl, ethyl and phenyl; and Y is —NH—C(O)—CH$_2$—N(R$^A$)(R$^B$), wherein:

each R$^A$ is independently selected from hydrogen and methyl;

R$^B$ is selected from hydrogen, (C$_1$-C$_7$)alkyl, —(C$_0$-C$_6$)alkylene-carbocyclyl, —(C$_0$-C$_6$)alkylene-aryl, —(C$_0$-C$_6$)alkylene-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocycle and —(C$_0$-C$_4$)alkylene-S(O)$_m$-heteroaryl; or R$^A$ and R$^B$ when bound to a common nitrogen atom are taken together with the nitrogen atom to form a heterocycle, wherein the heterocycle is optionally substituted with ═O and —N(R$^G$)(R$^G$);

R$^{D'}$ and R$^E$ are taken together with the carbon atom to which they are bound form a (C$_3$-C$_7$)cycloalkyl; and m is 1 or 2;

each carbocyclyl, aryl, heterocyclyl or heteroaryl is optionally and independently substituted with one or more substituents independently selected from halo, —(C$_1$-C$_4$)alkyl, halo-substituted —(C$_1$-C$_4$)alkyl, —O—(C$_1$-C$_4$)alkyl, and —N(R$^G$)(R$^G$);

each alkyl portion in the group represented by Y or R$^B$ is optionally and independently substituted with one or more substituents independently selected from halo, —OH, and —N(R$^G$)(R$^G$), wherein R$^G$ is hydrogen or (C$_1$-C$_4$)alkyl, and wherein each alkyl in the group represented by R$^G$ is optionally and independently substituted with (C$_3$-C$_6$) cycloalkyl. The remainder of the variables are as described above in the fifth alternative embodiment.

In a seventh alternative embodiment, for compounds represented by Structural Formula (A), X is selected from hydrogen and methyl; and Y is selected from —N(R$^A$)(R$^B$), —N(H)—C(O)-carbocyclyl, —N(H)—C(O)-aryl, —N(H)—C(O)-heterocycle, and —N(H)—C(O)-heteroaryl; or X is methyl; and
Y is —NH—C(O)—CH$_2$—N(R$^A$)(R$^B$),
wherein:
R$^A$ is hydrogen; and
R$^B$ is selected from (C$_1$-C$_4$)alkyl, and —S(O)$_2$—CH$_3$; or R$^A$ and R$^B$ taken together to form 4-7 membered heterocyclic ring; wherein each carbocyclyl, aryl, heteroaryl, or heterocycle is optionally and independently substituted with one or more substituents independently selected from —CH$_3$, fluoro, and —N(CH$_3$)$_2$.

In a eighth alternative embodiment, for compounds represented by Structural Formula (A), Y is

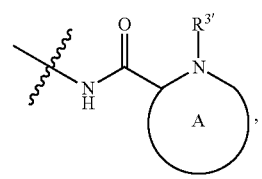

wherein ring A represents a 4-7 membered heterocyclyl; and R$^{3'}$ is hydrogen or (C$_1$-C$_6$)alkyl. Values and alternative values for the remainder of the variables are as described above for Structural Formula (A). More specifically, ring A is selected from the group consisting of azetidinyl, pyrrolidinyl, piperidinyl, or octahydrocyclopenta[c]pyrrolyl, each of which is optionally substituted with one or more substituents independently selected from the group consisting of halo, —($C_1$-$C_4$)alkyl, halo-substituted-($C_1$-$C_4$)alkyl (e.g., —$CF_3$), —OH, —O—($C_1$-$C_4$)alkyl, or —N($R^G$)($R^G$), wherein $R^G$ is hydrogen or ($C_1$-$C_4$)alkyl. Even more specifically, ring A described above is optionally substituted with one or more fluoro.

In a ninth alternative embodiment, for compounds represented by Structural Formula (A), Y is —NH—C(O)-heteroaryl. Values and alternative values for the remainder of the variables are as described above for Structural Formula (A). More specifically, the heteroaryl in —NH—C(O)-heteroaryl is selected from the group consisting of thienyl, pyridinyl, pyrrolyl, oxazolyl, pyrazolyl and thiazolyl, each of which is optionally substituted with one or more substituents independently selected from —($C_1$-$C_4$)alkyl, halo-substituted-($C_1$-$C_4$)alkyl (e.g., —$CF_3$), —OH, —O—($C_1$-$C_4$)alkyl, and —N($R^G$)($R^G$), wherein $R^G$ is hydrogen or ($C_1$-$C_4$)alkyl. More specifically, the pyrrolyl and pyrazolyl are optionally substituted with a methyl group on the N atom in the ring.

In a tenth alternative embodiment, for compounds represented by Structural Formula (A), Y is —NH—C(O)-phenyl. Values and alternative values for the remainder of the variables are as described above for Structural Formula (A). More specifically, the phenyl in —NH—C(O)-phenyl is optionally substituted with one or more substituents independently selected from —($C_1$-$C_4$)alkyl, halo-substituted-($C_1$-$C_4$)alkyl (e.g., —$CF_3$), —OH, —O—($C_1$-$C_4$)alkyl, and —N($R^G$)($R^G$), wherein $R^G$ is hydrogen or ($C_1$-$C_4$)alkyl. More specifically, the phenyl in —NH—C(O)-phenyl is optionally substituted with one or more substituents independently selected from —$CF_3$, —$OCH_3$ and —N($CH_3$)$_2$.

In a eleventh alternative embodiment, for compounds represented by Structural Formula (A), Y is represented by —NH—S(O)$_2$—($C_1$-$C_6$)alkyl, —NH—S(O)$_2$-phenyl, —NH—S(O)$_2$-heteroaryl. Values and alternative values for the remainder of the variables are as described above for Structural Formula (A). More specifically, the phenyl, heteroaryl or alkyl in the group represented by Y is optionally substituted with one or more substituents independently selected from —($C_1$-$C_4$)alkyl, halo-substituted-($C_1$-$C_4$)alkyl (e.g., —$CF_3$), —OH, —O—($C_1$-$C_4$)alkyl, and —N($R^G$)($R^G$), wherein $R^G$ is hydrogen or ($C_1$-$C_4$)alkyl.

In a twelfth alternative embodiment, for compounds represented by Structural Formula (A), Y is represented by —N($R^A$)($R^B$), wherein $R^A$ and $R^B$ are each independently selected from hydrogen, ($C_1$-$C_7$)alkyl, —($C_1$-$C_4$)alkyl-($C_3$-$C_6$)cycloalkyl, wherein the ($C_1$-$C_7$)alkyl is optionally substituted with —N($R^G$)($R^G$), wherein $R^G$ is hydrogen or ($C_1$-$C_4$)alkyl. Values and alternative values for the remainder of the variables are as described above for Structural Formula (A).

In a thirteenth alternative embodiment, for compounds represented by Structural Formula (A), Y is represented by —$CH_2$—N($R^A$)($R^B$), wherein $R^A$ and $R^B$ are each independently selected from hydrogen, ($C_1$-$C_7$)alkyl, —($C_1$-$C_4$)alkyl-($C_3$-$C_6$)cycloalkyl, or $R^A$ and $R^B$ taken together with the nitrogen atom to which they are bound form a heterocyclyl, wherein the ($C_1$-$C_7$)alkyl represented by $R^A$ or $R^B$ is optionally and independently substituted with —N($R^G$)($R^G$), wherein $R^G$ is hydrogen or ($C_1$-$C_4$)alkyl, and the ($C_1$-$C_4$)alkyl represented by $R^G$ is optionally substituted with —F. Values and alternative values for the remainder of the variables are as described above for Structural Formula (A).

In a fourteenth alternative embodiment, for compounds represented by Structural Formula (A), Y is represented by —$CH_2$—NH—C(O)—($CH_2$)$_{0-1}$—N($R^A$)($R^B$), wherein $R^A$ and $R^B$ are each independently selected from hydrogen, ($C_1$-$C_7$)alkyl, —($C_1$-$C_4$)alkyl-($C_3$-$C_6$)cycloalkyl. Values and alternative values for the remainder of the variables are as described above for Structural Formula (A).

The compound of the present invention is exemplified by the compounds shown in the Table below or a pharmaceutically acceptable salt thereof and compounds described in Examples 1-12 below or a pharmaceutically acceptable salt thereof:

| Compound No. | Chemical Structure |
|---|---|
| 11 | 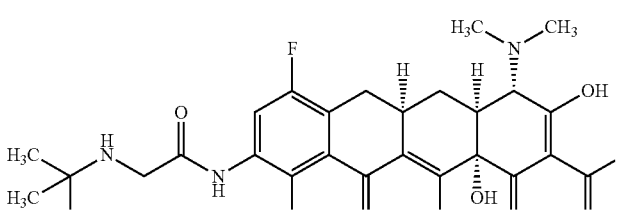 |
| 12 | 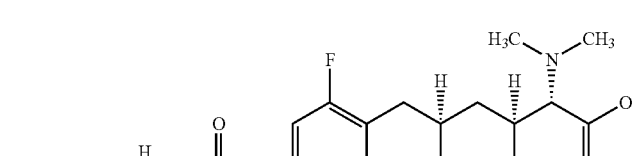 |

-continued
| Compound No. | Chemical Structure |
|---|---|
| 13 | 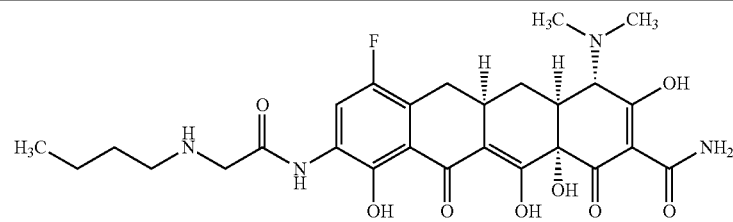 |
| 14 | 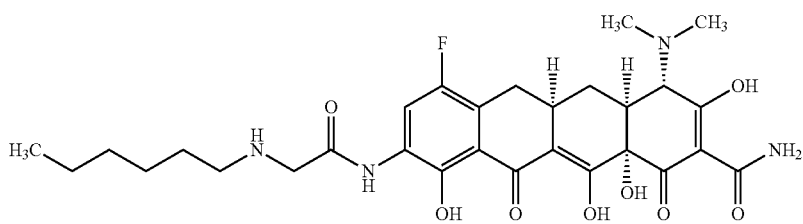 [SMILES: CCCCCCNCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 15 | 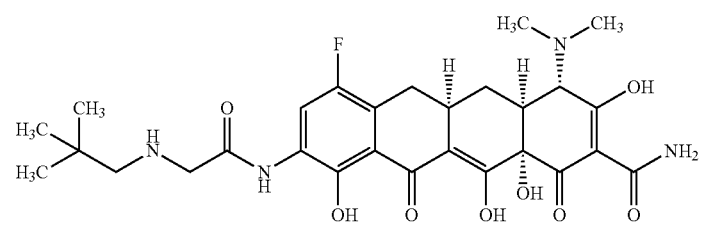 [SMILES: CN(C)[C@@H]1C(O)=C(C(N)=O)C(=O)[C@@]2(O)C(O)=C3C(=O)c4c(O)c(NC(=O)CNCC(C)(C)C)cc(F)c4C[C@H]3C[C@@H]12] |
| 16 | 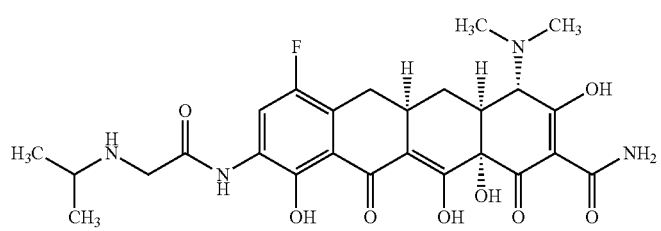 [SMILES: CC(C)NCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 17 | 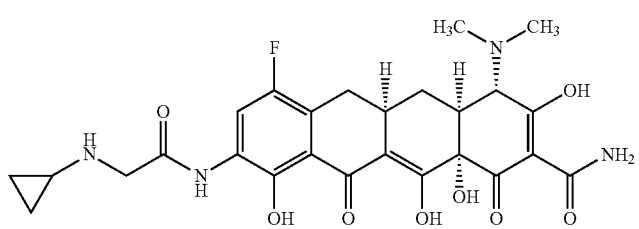 [SMILES: CN(C)[C@@H]1C(O)=C(C(N)=O)C(=O)[C@@]2(O)C(O)=C3C(=O)c4c(O)c(NC(=O)CNC5CC5)cc(F)c4C[C@H]3C[C@@H]12] |
| 18 | 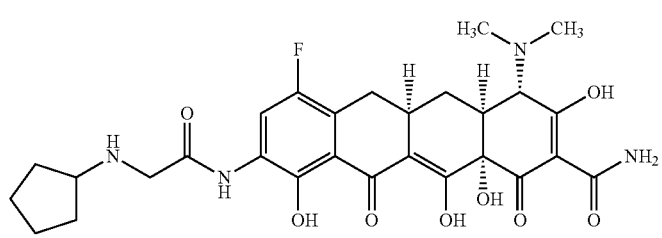 [SMILES: CN(C)[C@@H]1C(O)=C(C(N)=O)C(=O)[C@@]2(O)C(O)=C3C(=O)c4c(O)c(NC(=O)CNC5CCCC5)cc(F)c4C[C@H]3C[C@@H]12] |
| 19 | 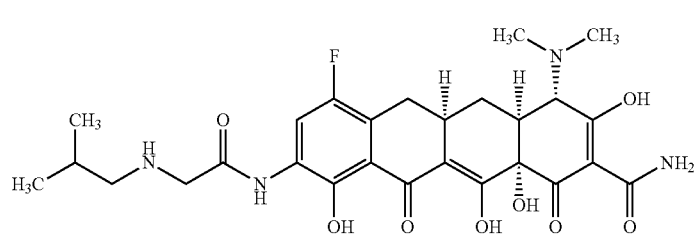 [SMILES: CC(C)CNCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |

-continued
| Compound No. | Chemical Structure |
|---|---|
| 20 | 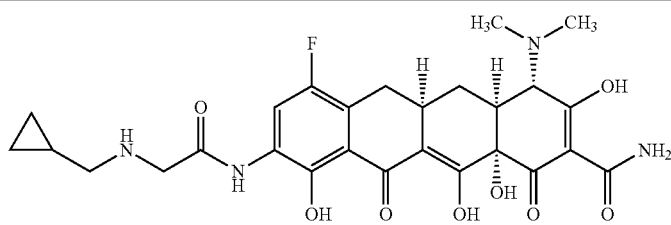 [SMILES: CN(C)[C@@H]1C(O)=C(C(N)=O)C(=O)[C@@]2(O)C(O)=C3C(=O)c4c(O)c(NC(=O)CNCC5CC5)cc(F)c4C[C@H]3C[C@@H]12] |
| 21 | 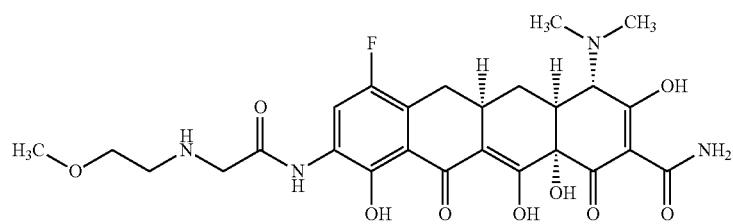 [SMILES: COCCNCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 22 | 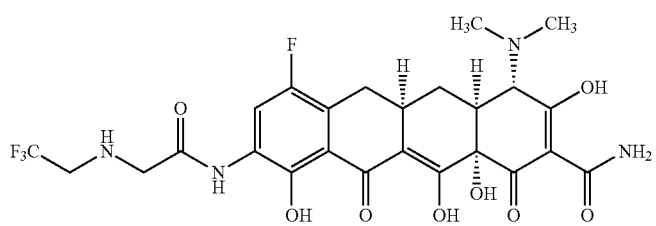 [SMILES: CN(C)[C@@H]1C(O)=C(C(N)=O)C(=O)[C@@]2(O)C(O)=C3C(=O)c4c(O)c(NC(=O)CNCC(F)(F)F)cc(F)c4C[C@H]3C[C@@H]12] |
| 23 | 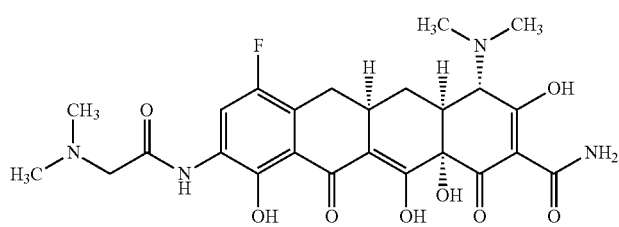 [SMILES: CN(C)CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 24 | 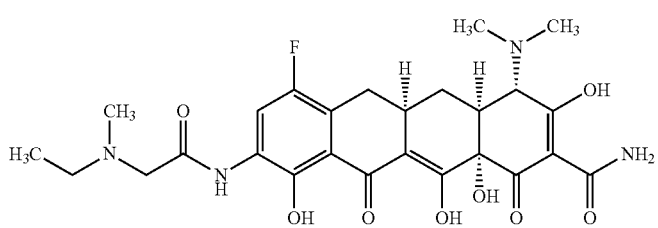 [SMILES: CCN(C)CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 25 | 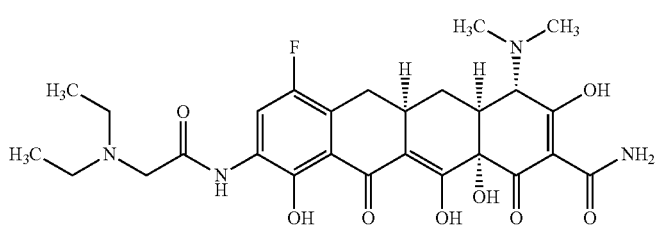 [SMILES: CCN(CC)CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 26 | 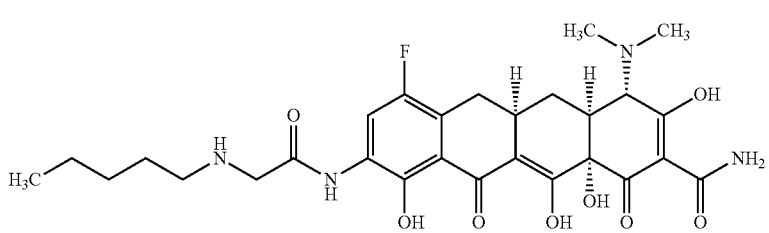 [SMILES: CCCCCNCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |

-continued

| Compound No. | Chemical Structure |
|---|---|
| 27 | 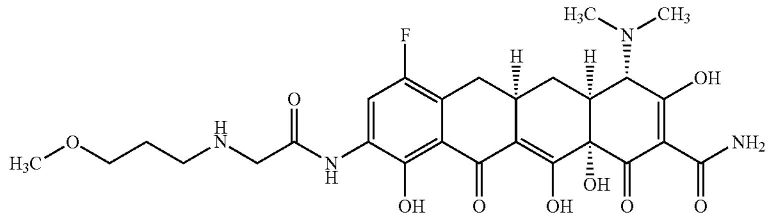 [SMILES: COCCCNCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 28 | 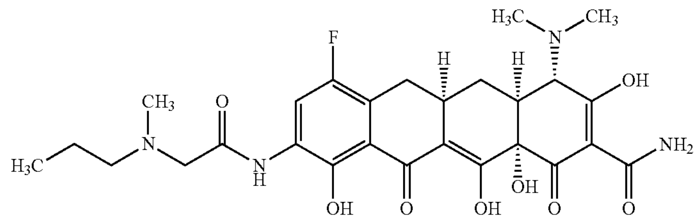 [SMILES: CCCN(C)CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 29 | 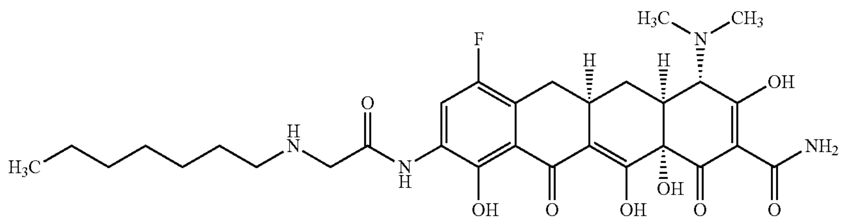 [SMILES: CCCCCCCNCC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 30 | 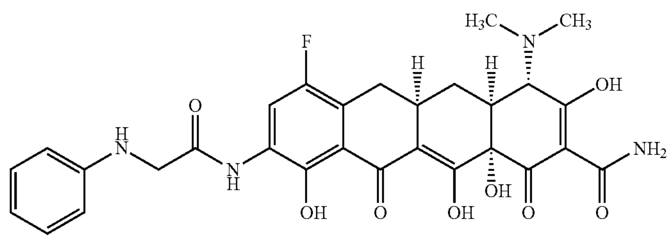 [SMILES: CN(C)[C@@H]1C(O)=C(C(N)=O)C(=O)[C@@]2(O)C(O)=C3C(=O)c4c(O)c(NC(=O)CNc5ccccc5)cc(F)c4C[C@H]3C[C@@H]12] |
| 31 | 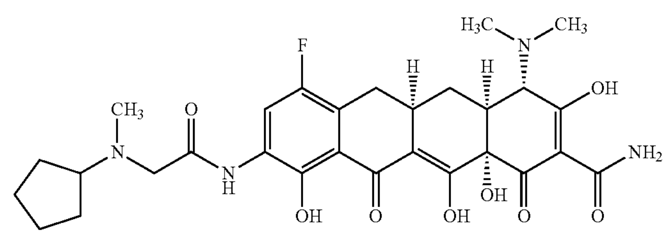 [SMILES: CN(CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2)C1CCCC1] |
| 32 | 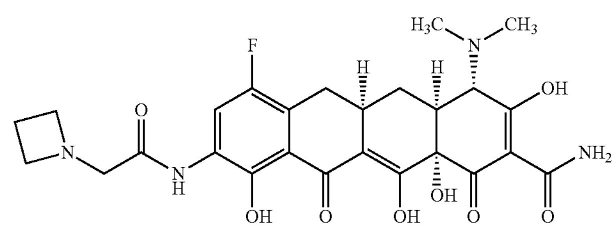 [SMILES: CN(C)[C@@H]1C(O)=C(C(N)=O)C(=O)[C@@]2(O)C(O)=C3C(=O)c4c(O)c(NC(=O)CN5CCC5)cc(F)c4C[C@H]3C[C@@H]12] |
| 33 | 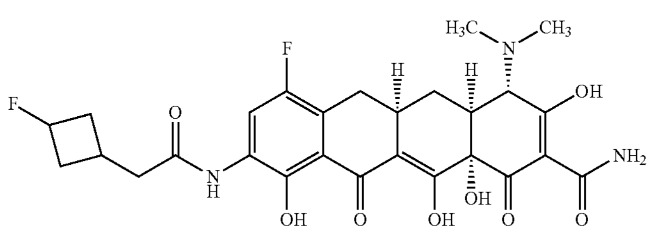 [SMILES: CN(C)[C@@H]1C(O)=C(C(N)=O)C(=O)[C@@]2(O)C(O)=C3C(=O)c4c(O)c(NC(=O)CC5CC(F)C5)cc(F)c4C[C@H]3C[C@@H]12] |

| Compound No. | Chemical Structure |
|---|---|
| 34 | 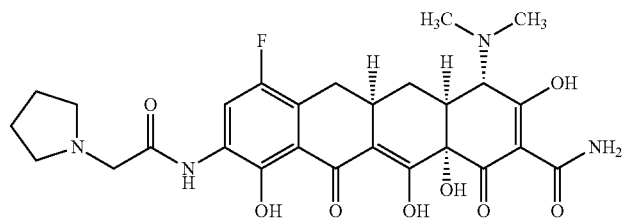 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12] |
| 35 | 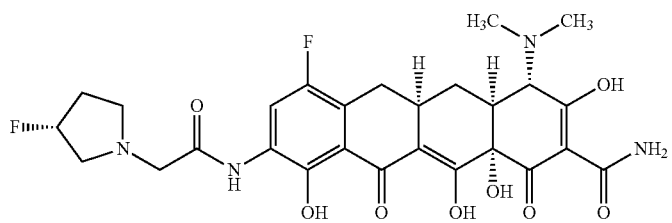 [SMILES: CN(C)[C@@H]1C(O)=C(C(N)=O)C(=O)[C@@]2(O)C(O)=C3C(=O)c4c(O)c(NC(=O)CN5CC[C@@H](F)C5)cc(F)c4C[C@H]3C[C@@H]12] |
| 36 | 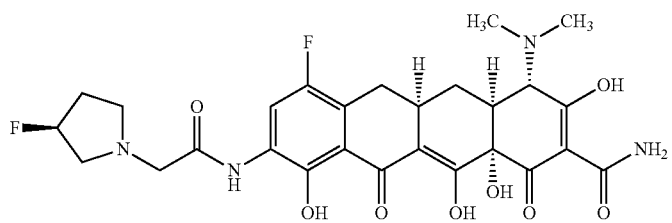 [SMILES: CN(C)[C@@H]1C(O)=C(C(N)=O)C(=O)[C@@]2(O)C(O)=C3C(=O)c4c(O)c(NC(=O)CN5CC[C@H](F)C5)cc(F)c4C[C@H]3C[C@@H]12] |
| 37 | 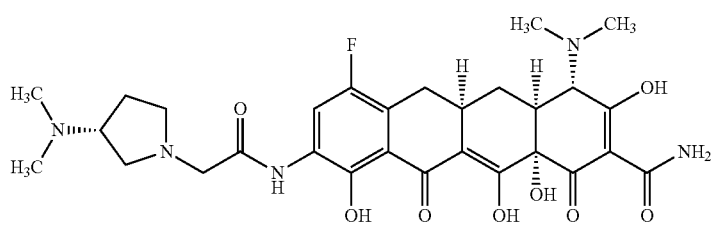 [SMILES: CN(C)[C@@H]1CCN(CC(=O)Nc2cc(F)c3c(c2O)C(=O)C2=C(O)[C@]4(O)C(=O)C(C(N)=O)=C(O)[C@@H](N(C)C)[C@@H]4C[C@@H]2C3)C1] |
| 38 | 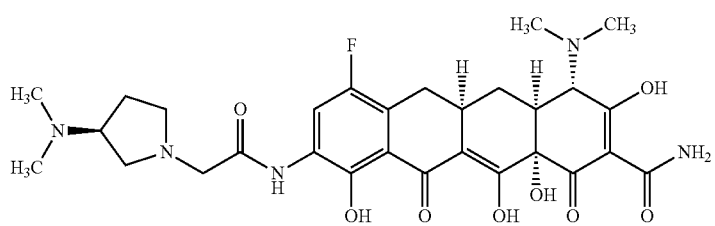 [SMILES: CN(C)[C@H]1CCN(CC(=O)Nc2cc(F)c3c(c2O)C(=O)C2=C(O)[C@]4(O)C(=O)C(C(N)=O)=C(O)[C@@H](N(C)C)[C@@H]4C[C@@H]2C3)C1] |
| 39 | 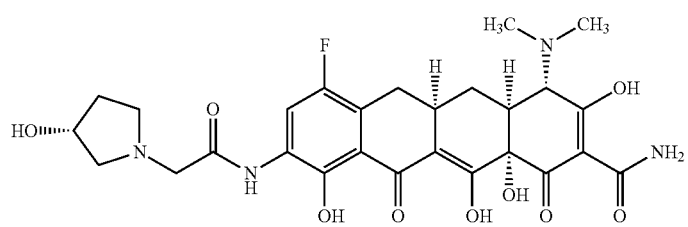 [SMILES: CN(C)[C@@H]1C(O)=C(C(N)=O)C(=O)[C@@]2(O)C(O)=C3C(=O)c4c(O)c(NC(=O)CN5CC[C@@H](O)C5)cc(F)c4C[C@H]3C[C@@H]12] |
| 40 | 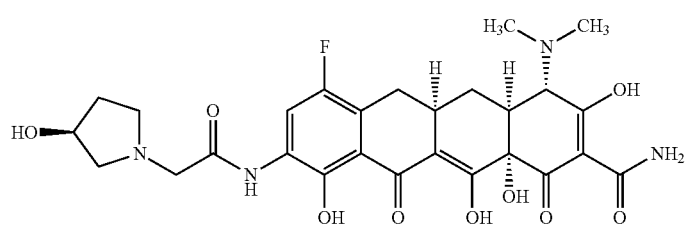 [SMILES: CN(C)[C@@H]1C(O)=C(C(N)=O)C(=O)[C@@]2(O)C(O)=C3C(=O)c4c(O)c(NC(=O)CN5CC[C@H](O)C5)cc(F)c4C[C@H]3C[C@@H]12] |

| Compound No. | Chemical Structure |
|---|---|
| 41 | 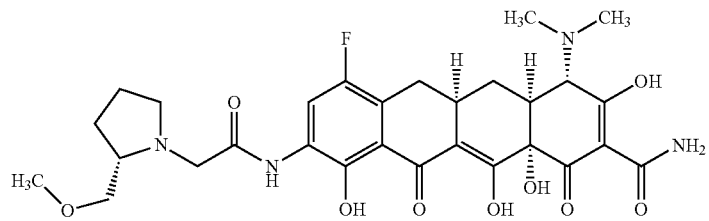 [SMILES: COC[C@@H]1CCCN1CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 42 | 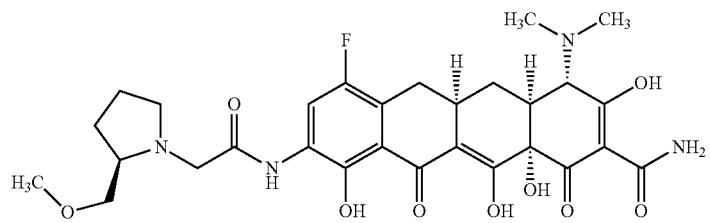 [SMILES: COC[C@H]1CCCN1CC(=O)Nc1cc(F)c2c(c1O)C(=O)C1=C(O)[C@]3(O)C(=O)C(C(N)=O)=C(O)[C@@H](N(C)C)[C@@H]3C[C@@H]1C2] |
| 43 | 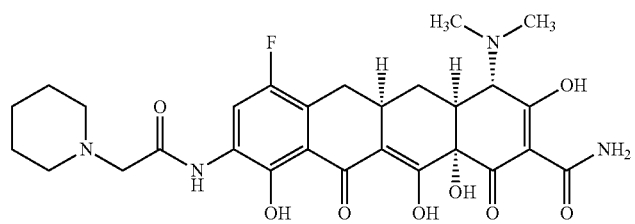 [SMILES: CN(C)[C@@H]1C(O)=C(C(N)=O)C(=O)[C@@]2(O)C(O)=C3C(=O)c4c(O)c(NC(=O)CN5CCCCC5)cc(F)c4C[C@H]3C[C@@H]12] |
| 44 | 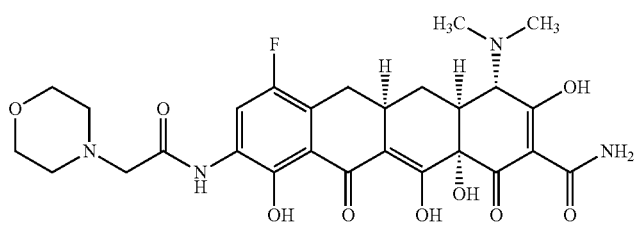 [SMILES: CN(C)[C@@H]1C(O)=C(C(N)=O)C(=O)[C@@]2(O)C(O)=C3C(=O)c4c(O)c(NC(=O)CN5CCOCC5)cc(F)c4C[C@H]3C[C@@H]12] |
| 45 | 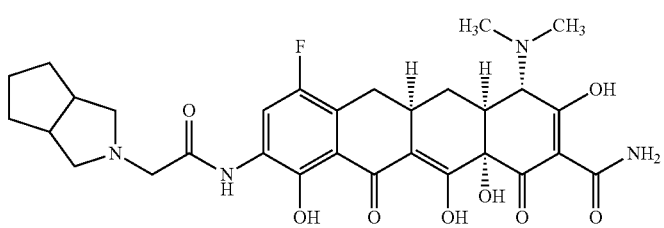 [SMILES: CN(C)[C@@H]1C(O)=C(C(N)=O)C(=O)[C@@]2(O)C(O)=C3C(=O)c4c(O)c(NC(=O)CN5CC6CCCC6C5)cc(F)c4C[C@H]3C[C@@H]12] |
| 46 | 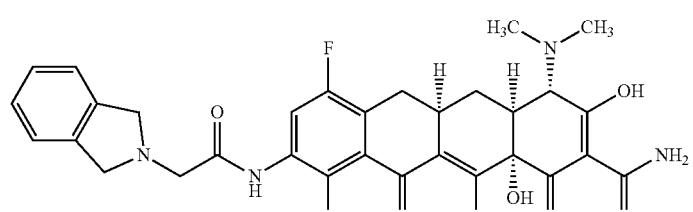 |

"Alkyl" means a saturated aliphatic branched or straight-chain monovalent hydrocarbon radical having the specified number of carbon atoms. Thus, "($C_1$-$C_7$)alkyl" means a radical having from 1-7 carbon atoms in a linear or branched arrangement. "($C_1$-$C_7$)alkyl" includes methyl, ethyl, propyl, butyl, pentyl, hexyl and heptyl. Suitable substitutions for a "substituted alkyl" include, but are not limited to, -halogen, —OH, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkoxy($C_1$-$C_4$)alkyl, and —N($R^3$)($R^4$), wherein $R^3$ and $R^4$ are as described above.

"Cycloalkyl" means a saturated aliphatic cyclic hydrocarbon radical having the specified number of carbon atoms. ($C_3$-$C_6$)cycloalkyl includes cyclopropyl, cyclobutyl, cyclopentyl, and cyclohexyl. Suitable substituents for a "substituted cycloalkyl" include halogen, —OH, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkoxy($C_1$-$C_4$)alkyl, and —N($R^3$)($R^4$), wherein $R^3$ and $R^4$ are as described above.

"Heterocycle" means a 4-12 membered partially unsaturated or saturated heterocyclic ring containing 1, 2, or 3 heteroatoms independently selected from N, O or S. When one heteroatom is S, it can be optionally mono- or di-oxygenated (i.e. —S(O)— or —S(O)$_2$—). The heterocycle can be monocyclic, fused bicyclic, bridged bicyclic, or spiro bicyclic.

Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocycle has two rings which have two adjacent ring atoms in common. The first ring is a monocyclic heterocycle and the second ring is a cycloalkyl, partially unsaturated carbocycle, phenyl, heteroaryl or a monocyclic heterocycle. For example, the second ring is a $(C_3-C_6)$cycloalkyl, such as cyclopropyl, cyclobutyl, cyclopentyl and cyclohexyl. Alternatively, the second ring is phenyl. Example of fused bicyclic heterocycles includes, but not limited to, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A spiro bicyclic heterocycle has two rings which have only one ring atom in common. The first ring is a monocyclic heterocycle and the second ring is a cycloalkyl, partially unsaturated carbocycle or a monocyclic heterocycle. For example, the second ring is a $(C_3-C_6)$cycloalkyl. Example of spiro bicyclic heterocycle includes, but not limited to, azaspiro[4.4]nonane, 7-azaspiro[4.4]nonane, azasprio[4.5]decane, 8-azaspiro[4.5]decane, azaspiro[5.5]undecane, 3-azaspiro[5.5]undecane and 3,9-diazaspiro[5.5]undecane.

A bridged bicyclic heterocycle has two rings which have three or more adjacent ring atoms in common. The first ring is a monocyclic heterocycle and the other ring is a cycloalkyl (such as $(C_3-C_6)$cycloalkyl), partially unsaturated carbocycle or a monocyclic heterocycle. Examples of bridged bicyclic heterocycles include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

When the heterocycle contains a N atom other than the nitrogen atom to which $R^1$ and $R^2$ are bonded, the N atom can be substituted with H, alkyl, cycloalkyl, cycloalkylalkyl, aryl, arylalkyl, heteroaryl, heteroarylalkyl, each of which can be optionally substituted with halogen, hydroxy, alkoxy, haloalkyl, alkyl, etc. The heterocycle can be optionally substituted with an oxo group (C=O) and oxo substituted heterocyclic rings include, but are not limited to, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one. Other optional substituents for a heterocycle include $(C_1-C_4)$alkyl, halo, —OH, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkoxy $(C_1-C_4)$alkyl, —N($R^3$)($R^4$), —CN, halo$(C_1-C_4)$alkyl, and halo$(C_1-C_4)$alkoxy.

"Heteroaryl" means a 5-12 membered monovalent heteroaromatic monocyclic or bicylic ring radical. A herteroaryl contains 1, 2 or 3 heteroatoms independently selected from N, O, and S. Heteroaryls include, but are not limited to pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyrazine, pyrimidine, pyridazine, 1,2,4-triazine, 1,3,5-triazine, and tetrazole. Bicyclic heteroaryl rings include, but are not limited to, bicyclo [4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

"Carbocycle" means 4-12 membered saturated or unsaturated aliphatic cyclic hydrocarbon ring.

"Alkoxy" means an alkyl radical attached through an oxygen linking atom. "Alkoxy" can also be depicted as —O-alkyl. For example, $(C_1-C_4)$-alkoxy can also depicted as —O—$(C_1-C_4)$alkyl. "$(C_1-C_4)$-alkoxy" includes methoxy, ethoxy, propoxy, and butoxy.

"Alkylthio" means an alkyl radical attached through a sulfur linking atom. "Alkylthio" can also be depicted as —S-alkyl. For example, "$(C_1-C_4)$alkylthio" can be depicted as —S—$(C_1-C_4)$alkyl. "$(C_1-C_4)$alkylthio" include methylthio, ethylthio, propylthio and butylthio.

"Alkylsulfinyl" means an alkyl radical attached through a —S(O)— linking group. "Alkylsulfinyl" can be depicted as —S(O)-alkyl. For example, "$(C_1-C_4)$alkylsulfinyl" can be depicted as —S(O)—$(C_1-C_4)$alkyl. "$(C_1-C_4)$alkylsulfinyl" include methylsulfinyl, ethylsulfinyl, propylsulfinyl and butylsulfinyl.

"Alkylsulfonyl" means an alkyl radical attached through a —S(O)$_2$— linking group. "Alkylsulfonyl" can be depicted as —S(O)$_2$-alkyl. For example, "$(C_1-C_4)$alkylsulfinyl" can be depicted as —S(O)$_2$—$(C_1-C_4)$alkyl. "$(C_1-C_4)$alkylsulfonyl" include methylsulfonyl, ethylsulfonyl, propylsulfonyl and butylsulfonyl.

Haloalkyl and halocycloalkyl include mono, poly, and perhaloalkyl groups where each halogen is independently selected from fluorine, chlorine, and bromine Haloalkyl and halocycloalkyl can also be referred as halo-substituted alkyl and halo-substituted cycloalkyl, respectively.

"Cycloalkoxy" means a cycloalkyl radical attached through an oxygen linking atom. "Cycloalkoxy" can also be depicted as —O-cycloalkyl. For example, "$(C_3-C_6)$cycloalkoxy" can be depicted as —O—$(C_3-C_6)$cycloalkyl. "$(C_3-C_6)$cycloalkoxy" includes cyclopropyloxy, cyclobutyloxy, cyclopentyloxy and cyclohexyloxy.

"Aryl" means an aromatic monocyclic or polycyclic (e.g. bicyclic or tricyclic) carbocyclic ring system. In one embodiment, "aryl" is a 6-12 membered monocylic or bicyclic systems. Aryl systems include, but not limited to, phenyl, naphthalenyl, fluorenyl, indenyl, azulenyl, and anthracenyl.

"Aryloxy" means an aryl moiety attached through an oxygen linking atom. "Aryloxy" can be also depicted as —O-aryl. Aryloxy includes, but not limited to, phenoxy.

"Arylthio" means an aryl moiety attached through a sulfur linking atom. "Arylthio" can be also depicted as —S-aryl. Arylthio includes, but not limited to, phenylthio.

"Arylsulfinyl" means an aryl moiety attached through a —S(O)— linking group. "Arylsulfinyl" can be also depicted as —S(O)-aryl. Arylsulfinyl includes, but not limited to, phenylsulfinyl.

"Arylsulfonyl" means an aryl moiety attached through a —S(O)$_2$— linking group. "Arylsulfonyl" can be also depicted as —S(O)$_2$-aryl. Arylsulfonyl includes, but not limited to, phenylsulfonyl.

"Hetero" refers to the replacement of at least one carbon atom member in a ring system with at least one heteroatom selected from N, S, and O. "Hetero" also refers to the replacement of at least one carbon atom member in a acyclic system. A hetero ring system or a hetero acyclic system may have 1, 2, or 3 carbon atom members replaced by a heteroatom.

"Halogen" or "halo" used herein refers to fluorine, chlorine, bromine, or iodine.

As used herein, cycloalkylalkyl can be depicted as -alkylene-cycloalkyl. For example, $(C_3-C_6)$cycloalkyl$(C_1-C_4)$alkyl can be depicted as —$(C_1-C_4)$alkylene-$(C_3-C_6)$cycloalkyl.

As use herein, alkoxyalkyl can be depicted as -alkylene-O-alkyl. For example, $(C_1-C_7)$alkoxy$(C_1-C_4)$alkyl can be depicted as —$(C_1-C_4)$alkylene-O—$(C_1-C_7)$alkyl.

As use herein, cycloalkoxyalkyl can be depicted as -alkylene-O-cycloalkyl. For example, $(C_3-C_6)$cycloalkoxy$(C_1-C_4)$alkyl can be depicted as —$(C_1-C_4)$alkylene-β-$(C_3-C_6)$alkyl.

As use herein, arylalkyl can be depicted as -alkylene-aryl. For example, aryl$(C_1-C_4)$alkyl can be depicted as —$(C_1-C_4)$alkylene-aryl.

As used herein, aryloxyalkyl can be depicted as -alkylene-O-aryl. For example, aryloxy$(C_1-C_4)$alkyl can be depicted as —$(C_1-C_4)$alkylene-O-aryl.

As used herein, arylthioalkyl can be depicted as -alkylene-S-aryl. For example, arylthio$(C_1-C_4)$alkyl can be depicted as —$(C_1-C_4)$alkylene-S-aryl.

As used herein, arylsufinylalkyl can be depicted as -alkylene-S(O)-aryl. For example, arylsufinyl$(C_1-C_4)$alkyl can be depicted as —$(C_1-C_4)$alkylene-S(O)-aryl.

As used herein, arylsulfonylalkyl can be depicted as -alkylene-S(O)$_2$-aryl. For example, arylsulfonyl$(C_1-C_4)$alkyl can be depicted as —$(C_1-C_4)$alkylene-S(O)$_2$-aryl.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

The present invention also provides a method of treating or preventing a subject with a tetracycline-responsive disease or disorder comprising administering to the subject an effective amount of a compound of the present invention or a pharmaceutically acceptable salt thereof.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, prostatitis, tumor growth and invasion, metastasis, diabetes, diabetic proteinuria, panbronchiolitis; aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold; Wegener's granulomatosis; neutrophilic dermatoses and other inflammatory diseases such as dermatitis herpetiformis, leukocytoclastic vasculitis, bullous lupus erythematosus, pustular psoriasis, erythema elevatum diutinum; vitiligo; discoid lupus erythematosus; pyoderma gangrenosum; pustular psoriasis; blepharitis, or meibomianitis; Alzheimer's disease; degenerative maculopathy; acute and chronic gastroenteritis and colitis; acute and chronic cystitis and urethritis; acute and chronic dermatitis; acute and chronic conjunctivitis; acute and chronic serositis; uremic pericarditis; acute and chronic cholecystis; cystic fibrosis, acute and chronic vaginitis; acute and chronic uveitis; drug reactions; insect bites; burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference).

In addition, a method to treat any disease or disease state that could benefit from modulating the expression and/or function of nitric oxide, metalloproteases, proinflammatory mediators and cytokines, reactive oxygen species, components of the immune response, including chemotaxis, lymphocyte transformation, delayed hypersensitivity, antibody production, phagocytosis, and oxidative metabolism of phagocytes. A method to treat any disease or disease state that could benefit from modulating the expression and/or function of C-reactive protein, signaling pathways (e.g., FAK signaling pathway), and/or augment the expression of COX-2 and $PGE_2$ production is covered. A method to treat any disease or disease state that could benefit from inhibition of neovascularization is covered.

Compounds of the invention can be used to prevent or treat important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48: 6686-6690 (1988)).

Infections that can be treated using compounds of the invention or a pharmaceutically acceptable salt thereof include, but are not limited to, skin infections, GI infections, urinary tract infections, genito-urinary infections, respiratory tract infections, sinuses infections, middle ear infections, systemic infections, cholera, influenza, bronchitis, acne, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection can be caused bacteria. In another embodiment, the infection is caused by a Gram-positive bacteria. In a specific aspect of this embodiment, the infection is caused by a Gram-positive bacterium selected from *Staphylococcus* spp., *Streptococcus* spp., *Propionibacterium* spp., *Enterococcus* spp., *Bacillus* spp., *Corynebacterium* spp., *Nocardia* spp., *Clostridium* spp., *Actinobacteria* spp., and *Listeria* spp.

In another embodiment, the infection is caused by a Gram-negative bacterium. In one aspect of this embodiment, the infection is caused by a proteobacteria (e.g., Betaproteobacteria and Gammaproteobacteria), including *Escherichia coli, Salmonella, Shigella*, other Enterobacteriaceae, *Pseudomonas, Moraxella, Helicobacter, Stenotrophomonas, Bdellovibrio*, acetic acid bacteria, *Legionella* or alpha-proteobacteria such as *Wolbachia*. In another aspect, the infection is caused by a Gram-negative bacteria selected from cyanobacteria, spirochaetes, green sulfur or green non-sulfur bacteria. In a specific aspect of this embodiment, the infection is caused by a Gram-negative bacteria selected from Enterobactericeae (e.g., *E. coli, Klebsiella pneumonia* including those containing extended-spectrum β-lactamases and/or carbapenemases), Bacteroidaceae (e.g., *Bacteroides fragilis*), Vibrionaceae (*Vibrio cholerae*), Pasteurellae (e.g., *Haemophilus influenza*), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of Proteeae, *Acinetobacter* spp., *Helicobacter* spp., and *Campylobacter* spp.

In a particular embodiment, the infection is caused by Gram-negative bacterium selected from the group consisting of Enterobactericeae (e.g., *E. coli, Klebsiella pneumoniae*), *Pseudomonas*, and *Acinetobacter* spp.

In another embodiment, the infection is caused by an organism selected from the group consisting of *K. pneumoniae, Salmonella, E. hirae, A. baumanii, M. catarrhalis, H. influenzae, P. aeruginosa, E. faecium, E. coli, S. aureus*, and *E. faecalis*.

In another embodiment, the infection is caused by an organism selected from the group consisting of rickettsiae, chlamydiae, *Legionella* spp. and *Mycoplasma* spp.

In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline.

In another embodiment, the infection is caused by a multidrug-resistant pathogen (having intermediate or full resistance to any two or more antibiotics). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria. In another embodiment, the infection is caused by *Bacillus anthracis* (anthrax), *Yersinia pestis* (plague), or *Francisella tularensis* (tularemia).

In yet another embodiment, the infection can be caused by more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus, Serratia, Staphylococcus* and *Enterococcus* spp., anaerobes (S. E. Dowd, et al., PloS one 2008; 3:e3326) and respiratory disease (especially in patients that have chronic infections like cystic fibrosis—e.g., *S.*

*aureus* plus *P. aeruginosa* or H influenza, atypical pathogens), wounds and abscesses (various gram-negative and gram-positive bacteria, notably MSSA/MRSA, coagulase-negative staphylococci, enterococci, *Acinetobacter, P. aeruginosa, E. coli, B. fragilis*), and bloodstream infections (13% were polymicrobial (H. Wisplinghoff, et al., Clin. Infect. Dis. 2004; 39:311-317)).

In a further embodiment, the tetracycline responsive disease or disorder is not a bacterial infection. In another embodiment, the tetracycline compounds of the invention are essentially non-antibacterial. For example, non-antibacterial compounds of the invention may have MIC values greater than about 4 µg/ml (as measured by assays known in the art and/or the assay given in Example 14. In another embodiment, the tetracycline compounds of the invention have both antibacterial and non-antibacterial effects.

Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendonitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity.

Examples of matrix metalloproteinase associated states ("MMPAS's") can be treated using compounds of the invention or a pharmaceutically acceptable salt thereof, include, but are not limited to, arteriosclerosis, corneal ulceration, emphysema, osteoarthritis, multiple sclerosis (Liedtke et al., Ann. Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compounds of the present invention or a pharmaceutically acceptable salt thereof include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. No. 6,100,248; 5,843,925; 5,837,696; or 5,668,122, incorporated herein by reference in their entirety.

Alternatively, the tetracycline compounds may be useful for preventing or reducing the likelihood of cancer recurrence, for example, to treat residual cancer following surgical resection or radiation therapy. The tetracycline compounds useful according to the invention are especially advantageous as they are substantially non-toxic compared to other cancer treatments.

In a further embodiment, the compounds of the invention are administered in combination with standard cancer therapy, such as, but not limited to, chemotherapy.

Examples of tetracycline responsive states can be treated using the compounds of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compounds of the invention or a pharmaceutically acceptable salt thereof include, but are not limited to, juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited to, asthma, cystic fibrosis, chronic obstructive pulmonary disease (COPD), and emphysema. In a further embodiment, the acute and/or chronic lung disorders that can be treated using the compounds of the invention or a pharmaceutically acceptable salt thereof include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the tetracycline compounds of the invention or a pharmaceutically acceptable salt thereof can be used to treat such disorders as described above and in U.S. Pat. Nos. 6,231,894; 5,773,430; 5,919,775 and 5,789,395, incorporated herein by reference.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a tetracycline compound of the invention or a pharmaceutically acceptable salt thereof to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the tetracycline compound of the invention or a pharmaceutically acceptable salt thereof is used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The tetracycline compound or a pharmaceutically acceptable salt thereof may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

The compounds of the invention or a pharmaceutically acceptable salt thereof can be used alone or in combination with one or more therapeutic agent in the methods of the invention disclosed herein.

The language "in combination with" another therapeutic agent or treatment includes co-administration of the tetracycline compound and with the other therapeutic agent or treatment as either a single combination dosage form or as multiple, separate dosage forms, administration of the tetracycline compound first, followed by the other therapeutic agent or treatment and administration of the other therapeutic agent or treatment first, followed by the tetracycline compound.

The other therapeutic agent may be any agent that is known in the art to treat, prevent, or reduce the symptoms of a tetracycline-responsive disease or disorder. The choice of additional therapeutic agent(s) is based upon the particular tetracycline-responsive disease or disorder being treated. Such choice is within the knowledge of a treating physician. Furthermore, the other therapeutic agent may be any agent of benefit to the patient when administered in combination with the administration of a tetracycline compound.

As used herein, the term "subject" means a mammal in need of treatment or prevention, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or 'treatment" refers to obtaining desired pharmacological and/or physiological effect. The effect can include achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome.

As used herein, "preventing" or "prevention" refers to reducing the likelihood of the onset or development of disease, disorder or syndrome.

"Effective amount" means that amount of active compound agent that elicits the desired biological response in a subject. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In another embodiment, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the composition of this invention includes one or more additional agents. The other therapeutic agent may be ay agent that is capable of treating, preventing or reducing the symptoms of a tetracycline-responsive disease or disorder. Alternatively, the other therapeutic agent may be any agent of benefit to a patient when administered in combination with the tetracycline compound in this invention.

While this invention has been particularly shown and described with references to example embodiments thereof, it will be understood by those skilled in the art that various changes in form and details may be made therein without departing from the scope of the invention encompassed by the appended claims.

EXEMPLIFICATION

The following abbreviations and the terms have the indicated meanings:

| Abbreviation/Term | Meaning |
| --- | --- |
| Ac | acetyl |
| AIBN | 2,2'-azobis(2-methylpropionitrile) |
| aq | aqueous |
| Bn | benzyl |
| brine | saturated aqueous sodium chloride |
| Boc | tert-butoxy carbonyl or t-butoxy carbonyl |
| (Boc)$_2$O | di-tert-butyl dicarbonate |
| BBr$_3$ | boron tribromide |
| Bu | butyl |
| Cbz | benzyloxycarbonyl |
| CH$_2$Cl$_2$ | methylene chloride |
| CH$_3$CN or MeCN | acetonitrile |
| Cy | tricyclohexylphosphine |
| dba | dibenzylideneacetone |
| DIBAL-H | diisobutylaluminum hydride |
| DIEA | N,N-diisopropylethylamine |
| DMAP | 4-(dimethylamino)pyridine |
| DME | 1,2-dimethoxyethane |
| DMF | N,N-dimethylformamide |
| DMPU | 1,3-dimethyl-3,4-5,6-tetrahydro-2(1 H)-pyrimidone |
| DMSO | dimethyl sulfoxide |

| Abbreviation/Term | Meaning |
|---|---|
| EDC | N-(3-dimethylaminopropyl)-N'-ethylcarbodiimide |
| ESI | electrospray ionization |
| equiv. | equivalent |
| Et | ethyl |
| $Et_2O$ | ethyl ether |
| EtOAc | ethyl acetate |
| h, hr | hour |
| HCl | hydrochloric acid |
| $KHPO_4$ | potassium hydrogenphosphate |
| HPLC | high performance liquid chromatography |
| HOBt | 1-hydroxybenzotriazole |
| i | iso |
| IBX | 2-iodoxybenzoic acid |
| LDA | lithium diisopropylamide |
| LHMDS | lithium bis(trimethylsilyl)amide |
| LTMP | lithium 2,2,6,6-tetramethylpiperidide |
| Me | methyl |
| MeOH | methanol |
| MeI | methyl iodide |
| min | minute |
| Ms | methanesulfonyl |
| MS | mass spectrum |
| MTBE | methyl tert-butyl ether |
| MW | molecular weight |
| $NaHCO_3$ | sodium bicarbonate |
| NaOH | sodium hydroxide |
| $Na_2SO_4$ | sodium sulfate |

| Abbreviation/Term | Meaning |
|---|---|
| NBS | N-bromosuccinimide |
| NCS | N-chlorosuccinimide |
| NMR | nuclear magnetic resonance spectrometry |
| Ph | phenyl |
| Pr | propyl |
| s | secondary |
| t | tertiary |
| RP | reverse phase |
| TMEDA | tetramethylethylenediamine |
| TBS | tert-butyldimethylsilyl |
| TEA | triethylamine |
| Tf | trifluoromathanesulfonyl |
| TFA | trifluoroacetic acid |
| TFAA | trifluoroacetic anhydride |
| THF | tetrahydrofuran |
| TLC | thin layer chromatography |
| Ts | para-toluenesulfonyl |
| TsOH | para-toluenesulfonic acid |
| Xantphos | 4,5-bis(diphenylphosphino)-9,9-dimethylxanthene |

Example 1

Synthesis of Compounds of Structural Formula (I)

The compounds of the invention can be prepared according the synthetic scheme shown in Scheme 1.

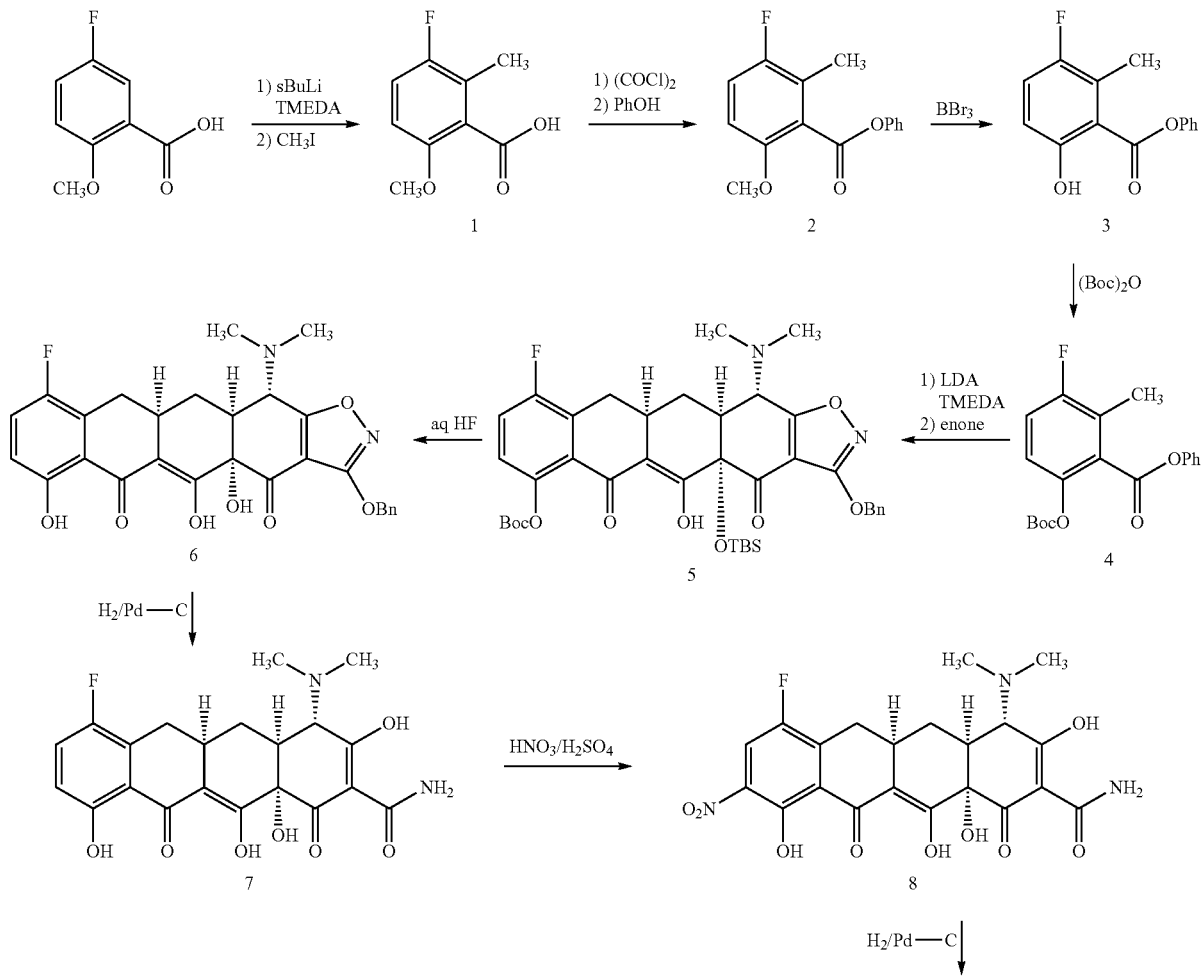

Scheme 1

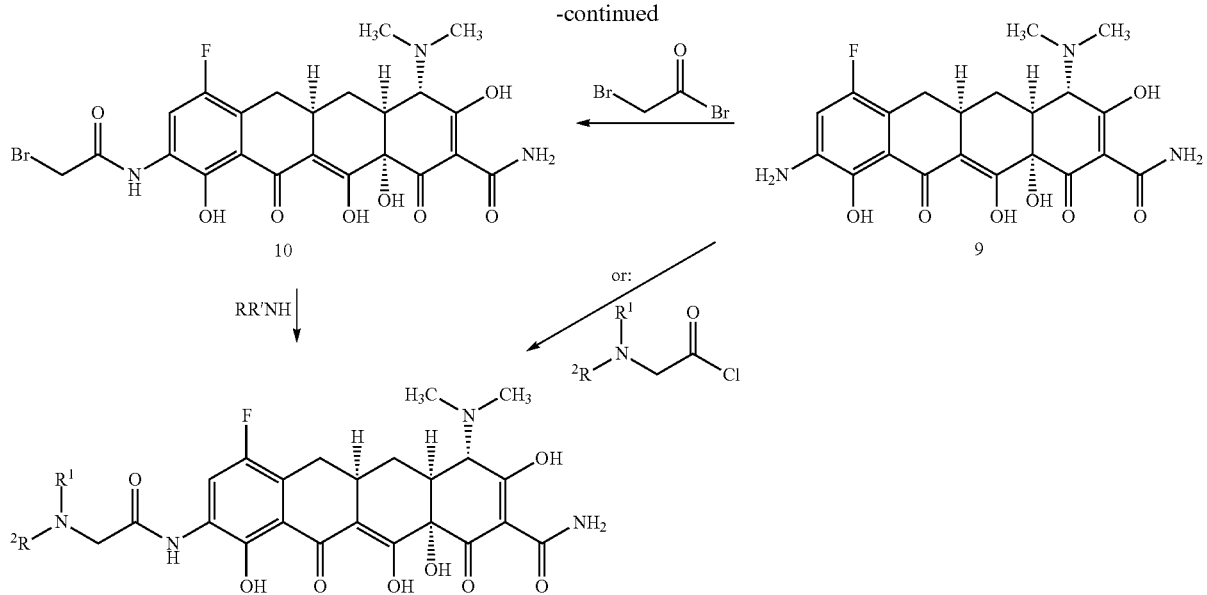

Specific conditions for the reactions depicted in Scheme 1 are provided in the following examples.

Compound 1

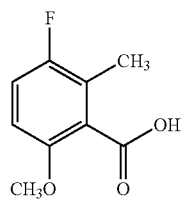

1

To a THF solution of 5-fluoro-2-methoxybenzoic acid (500 mg, 2.94 mmol, Aldrich 523097) cooled at −78° C. was added a THF solution of s-BuLi (4.60 mL, 1.40 M, 6.44 mmol, 2.2 equiv) and TMEDA (0.97 mL, 6.47 mmol, 2.2 equiv). The reaction was stirred at −78° C. for 2 h. MeI (1.10 mL, 17.64 mmol, 6.0 equiv) was added to the reaction mixture dropwise. The reaction was allowed to warm to 25° C. over 1 h and stirred at 25° C. for 1 h. NaOH (6 N, 20 mL) was added. The resulting mixture was extracted with t-butylmethyl ether (20 mL×2). The aqueous layer was acidified with HCl (6 N) to pH 1 and extracted with EtOAc (20 mL×4). The combined EtOAc extracts were dried (Na$_2$SO$_4$) and concentrated to give 510 mg of crude product 1: $^1$H NMR (400 MHz, CDCl$_3$) δ 7.06 (dd, J=9.8, 8.5 Hz, 1H), 6.75 (dd, J=9.8, 3.7 Hz, 1H), 3.86 (s, 3H), 2.34 (d, J=2.4 Hz, 3H); MS (ESI) m/z 185.12 (M+H).

Compound 2

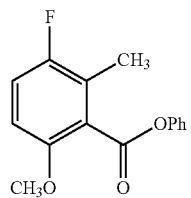

2

Oxalyl chloride (0.95 mL, 11.10 mmol, 5.5 equiv) was added to CH$_2$Cl$_2$ solution (15 mL, anhydrous) of 1 (510 mg, 2.00 mmol). DMF (0.1 mL) was added to the resulting mixture. The reaction was stirred at 25° C. for 1 h and concentrated. The resulting solid was re-dissolved in 15 mL of anhydrous CH$_2$Cl$_2$. Phenol (520 mg, 5.50 mmol, 2.8 equiv), DMAP (670 mg, 5.6 mmol, 2.8 equiv), and triethylamine (1.90 mL, 13.90 mmol, 7.0 equiv) were added to the reaction mixture. The reaction was stirred at 25° C. for 12 h and concentrated. EtOAc and H$_2$O were added to the residue. The organic layer was washed with NaOH (1 N), H$_2$O, and brine, dried (Na$_2$SO$_4$), and concentrated. Flash chromatography on silica gel (40:1 hexanes/EtOAc) yielded 400 mg of compound 2 (52% for 2 steps): $^1$H NMR (400 MHz, CDCl$_3$) δ 7.47-7.41 (m, 2H), 7.31-7.24 (m, 3H), 7.08 (dd, J=9.2, 9.2 Hz, 1H), 6.77 (dd, J=9.2, 3.7 Hz, 1H), 3.88 (s, 3H), 2.36 (d, J=2.3 Hz, 3H); MS (ESI) m/z 261.12 (M+H).

Compound 3

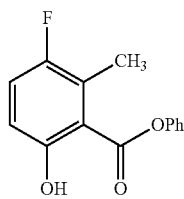

3

BBr$_3$ (1.85 mL, 1 M, 1.85 mmol, 1.2 equiv) was added to a CH$_2$Cl$_2$ solution (8 mL) of 2 (400 mg, 1.54 mmol) at −78° C. The reaction was stirred from −78° C. to 25° C. for 1.5 h, quenched with saturated NaHCO$_3$ and concentrated. EtOAc and H$_2$O were added to the reaction mixture. The aqueous layer was extracted with EtOAc. The combined EtOAc extracts were dried (Na$_2$SO$_4$) and concentrated to yield 360 mg of crude 3: $^1$H NMR (400 MHz, CDCl$_3$) δ 10.66 (s, 1H), 7.50-7.44 (m, 2H), 7.36-7.31 (m, 1H), 7.26-7.18 (m, 3H), 6.86 (dd, J=9.3, 4.9 Hz, 1H), 2.60 (d, J=2.4 Hz, 3H); MS (ESI) m/z 245.11 (M−H).

Compound 4

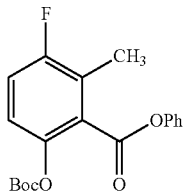

Boc₂O (350 mg, 1.60 mmol, 1.1 equiv) and DMAP (20 mg, 0.16 mmol, 0.1 equiv) were added to a CH₂Cl₂ solution of crude 3 (360 mg). The reaction was stirred at 25° C. for 1.5 h and concentrated. Flash chromatography on silica gel (35:1 hexanes/EtOAc) yielded 400 mg of compound 4 (94% for 2 steps): ¹H NMR (400 MHz, CDCl₃) δ 7.46-7.41 (m, 2H), 7.31-7.23 (m, 3H) 7.18 (dd, J=8.8, 8.7 Hz, 1H), 7.10 (dd, J=8.8, 4.4 Hz, 1H), 2.41 (d, J=2.3 Hz, 3H), 1.44 (s, 9H); MS (ESI) m/z 345.18 (M−H).

Compound 5

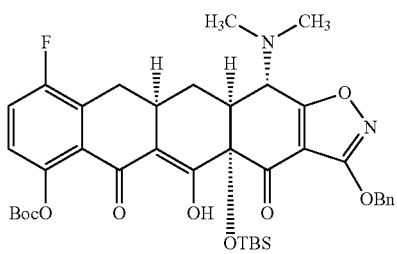

A THF solution (6 mL) of 4 (487 mg, 1.40 mmol, 2.0 equiv) was added to a THF solution (5 mL) of LDA (6.30 mL, 10% wt, 4.20 mmol, 6.0 equiv) and TMEDA (1.70 mL, 11.20 mmol, 16.0 equiv) at −78° C. The reaction was stirred at −78° C. for 5 min. A THF solution of enone (339 mg, 0.70 mmol, 1.0 equiv) was added to the reaction mixture dropwise. The reaction was stirred from −78° C. to 25° C. for 1 h, quenched with saturated NH₄Cl, and extracted with EtOAc. The combined EtOAc extracts were dried (Na₂SO₄) and concentrated to yield the crude product. Preparative reverse phase HPLC purification on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 80→100% B over 15 min; mass-directed fraction collection]. Fractions with the desired MW, eluting at 6.3-8.0 min, were collected and concentrated on a RotaVap at rt to remove most of the acetonitrile. The resulting mostly aqueous solution was extracted with EtOAc. The combined EtOAc extracts were dried (Na₂SO₄) and concentrated to give 185 mg of pure 5 (35%): ¹H NMR (400 MHz, CDCl₃) δ 15.67 (s, 1H), 7.51-7.46 (m, 2H), 7.39-7.29 (m, 3H), 7.21 (dd, J=8.9, 8.9 Hz, 1H), 7.03 (dd, J=8.9, 4.0 Hz, 1H), 5.34 (s, 2H), 3.93 (d, J=10.4 Hz, 1H), 3.30-3.21 (m, 1H), 3.10-3.00 (m, 1H), 2.57-2.41 (m, 3H), 2.48 (s, 6H), 2.17-2.12 (m, 1H), 1.53 (s, 9H), 0.82 (s, 9H), 0.26 (s, 3H), 0.12 (s, 3H); MS (ESI) m/z 735.45 (M+H).

Compound 6

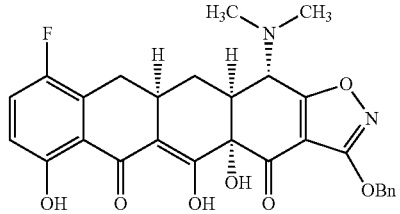

Aqueous HF (3 mL, 48%) and TFA (4 μL) were added to a CH₃CN solution (7 mL) of 5 (210 mg, 0.29 mmol) in a polypropylene tube at 25° C. The reaction was stirred at 25° C. for 18 h. The resulting mixture was poured into an aqueous solution of K₂HPO₄ (21 g, dissolved in 150 mL water). The mixture was extracted with EtOAc. The combined EtOAc extracts were dried (Na₂SO₄) and concentrated to yield 180 mg of crude 6: ¹H NMR (400 MHz, CDCl₃) δ 14.64 (s, 1H), 11.47 (s, 1H), 7.49-7.45 (m, 2H), 7.39-7.32 (m, 3H), 7.14 (dd, J=9.2, 8.8 Hz, 1H), 6.77 (dd, J=9.2, 4.3 Hz, 1H), 5.36 (s, 2H), 3.68 (d, J=3.7 Hz, 1H), 3.09 (dd, J=15.6, 4.6 Hz, 1H), 3.02-2.92 (m, 1H), 2.84-2.79 (m, 1H), 2.49 (s, 6H), 2.34-2.22 (m, 1H), 2.09-2.02 (m, 1H), 1.55-1.44 (m, 1H); MS (ESI) m/z 521.30 (M+H).

Compound 7

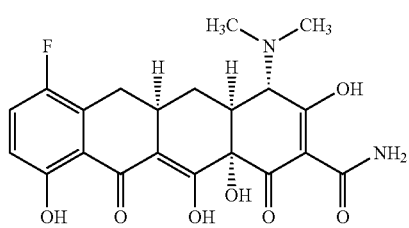

Palladium on carbon (35 mg, 10 wt %) was added to a MeOH/dioxane solution (4 mL/4 mL) of crude 6 (180 mg). The reaction was purged with hydrogen and stirred under H₂ (balloon) at 25° C. for 1 h. The reaction mixture was filtered through a small Celite plug. The filtrate was concentrated to yield the crude product. Preparative reverse phase HPLC purification on a Waters Autopurification system using a Phenomenex Polymerx 10μ, RP-1 100A column [10 μm, 150× 21.20 mm; flow rate, 20 mL/min; Solvent A: 0.05 N HCl/water; Solvent B: CH₃CN; injection volume: 4.0 mL (0.05 N HCl/water); gradient: 0→100% B over 15 min; mass-directed fraction collection]. Fractions with the desired MW, eluting at 6.4-8.2 min, were collected and freeze-dried to yield 51 mg of compound 7 (41% for 2 steps): ¹H NMR (400 MHz, CD₃OD) δ 7.26 (dd, J=9.2, 9.2 Hz, 1H), 6.80 (dd, J=9.2, 4.3 Hz, 1H), 4.09 (br s, 1H), 3.14 (dd, J=15.0, 4.6 Hz, 1H), 3.04 (s, 3H), 2.96 (s, 3H), 3.09-2.91 (m, 2H), 2.31-2.18 (m, 2H), 1.68-1.56 (m, 1H); MS (ESI) m/z 433.28 (M+H).

Compound 8

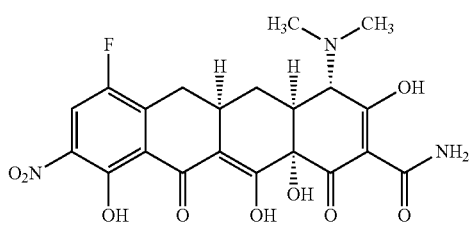

Compound 11

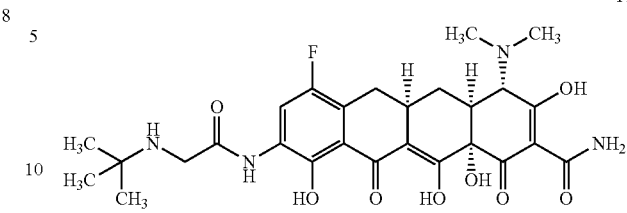

A mixture of HNO₃ (8.5 µL, 69%) and H₂SO₄ (0.5 mL) was added to a H₂SO₄ solution (1 mL) of 7 (51 mg, 0.12 mmol) at 0° C. The reaction was stirred at 0° C. for 30 min. The resulting mixture was added dropwise to vigorously stirred diethyl ether (60 mL). The suspension was filtered through a small Celite pad and washed several times with more diethyl ether. The Celite pad was then eluted with MeOH until the eluent became colorless. The yellow MeOH eluent was collected and concentrated under reduced pressure to afford crude 8: $^1$H NMR (400 MHz, CD₃OD) δ 8.03 (d, J=8.5 Hz, 1H), 4.09 (br s, 1H), 3.50-2.97 (m, 3H), 3.04 (s, 3H), 2.96 (s, 3H), 2.46-2.36 (m, 1H), 2.29-2.20 (m, 1H), 1.71-1.59 (m, 1H); MS (ESI) m/z 478.20 (M+H).

2-t-Butylaminoacetylchloride hydrochloride (4.2 mg, 0.022 mmol, 2.0 equiv) was added to a DMF solution (0.1 mL) of 9 (5 mg, 0.011 mmol) at 25° C. The reaction was stirred at 25° C. for 30 min. The reaction mixture was diluted with 0.05 N HCl (2 mL) and injected into a Waters Autopurification system equipped with a Phenomenex Polymerx 10 g RP-1 100A column [10 µm, 150×21.20 mm; flow rate, 20 mL/min; Solvent A: 0.05 N HCl; Solvent B: CH₃CN; gradient: 0-100% B over 20 min; mass-directed fraction collection]. Fractions with the desired MW, eluting at 6.4-7.0 min, were collected and freeze-dried to yield 3.9 mg of pure 11 (62%): $^1$H NMR (400 MHz, CD₃OD) δ 8.25 (d, J=11.0 Hz, 1H), 4.11 (br s, 1H), 4.09 (s, 2H), 3.22-2.86 (m, 3H), 3.05 (s, 3H), 2.97 (s, 3H), 2.33-2.20 (m, 2H), 1.69-1.57 (m, 1H), 1.42 (s, 9H); MS (ESI) m/z 561.39 (M+H).

Compound 9

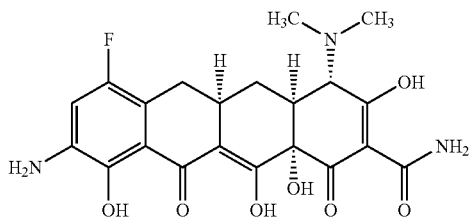

Compound 32

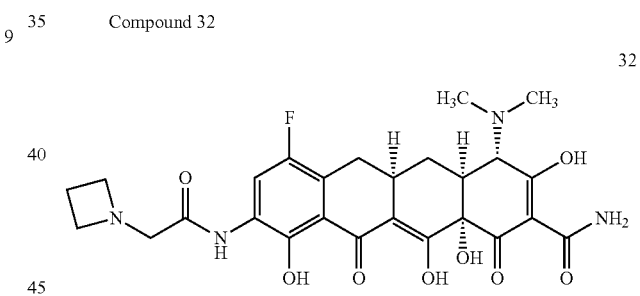

Palladium on carbon (12 mg, 10 wt %) was added to a MeOH solution (4 mL) of crude 8. The reaction was purged with hydrogen and stirred under H₂ (balloon) at 25° C. for 2 h. The catalyst was filtered off with a small Celite pad. The filtrate was concentrated to yield crude 9. Preparative reverse phase HPLC purification on a Waters Autopurification system using a Phenomenex Polymerx 10µ RP-1 100A column [10 µm, 150×21.20 mm; flow rate, 20 mL/min; Solvent A: 0.05 N HCl; Solvent B: CH₃CN; injection volume: 4.0 mL (0.05 N HCl/water); gradient: 0-100% B over 15 min; mass-directed fraction collection]. Fractions with the desired MW, eluting at 5.0-6.6 min, were collected and freeze-dried to yield 43 mg of pure 9 (81% for 2 steps): $^1$H NMR (400 MHz, CD₃OD) δ 7.43 (d, J=8.5 Hz, 1H), 4.11 (br s, 1H), 3.22-3.16 (m, 1H), 3.15-3.08 (m, 1H), 3.06-2.95 (m, 1H), 3.04 (s, 3H), 2.96 (s, 3H), 2.40-2.31 (m, 1H), 2.28-2.21 (m, 1H), 1.71-1.59 (m, 1H); MS (ESI) m/z 448.24 (M+H).

Anhydrous Na₂CO₃ (16 mg, 0.15 mmol, 5.5 equiv) was added to an anhydrous DMPU/acetonitrile (150 µL/50 µL) solution of 9 (12 mg, 0.027 mmol). Bromoacetyl bromide (2.8 µL, 0.032 mmol, 1.2 equiv) was added to the mixture. The reaction was stirred at 25° C. for 10 min. LC/MS analysis indicated complete formation of intermediate 10. Azetidine (36 µL, 0.54 mmol, 20 equiv) was added to the reaction mixture. The reaction was stirred at 25° C. for 2 h. The reaction mixture was concentrated and acidified with HCl (0.5 N in ° MeOH, 0.7 mL). The resulting mixture was added dropwise to vigorously stirred diethyl ether (10 mL). The suspension was filtered through a small Celite pad and washed several times with more diethyl ether. The Celite pad was then eluted with MeOH until the eluent became colorless. The yellow MeOH eluent was collected and concentrated under reduced pressure to afford crude 32. Preparative reverse phase HPLC purification on a Waters Autopurification system using a Phenomenex Polymerx 10μ RP-1 100A column [10 μm, 150×21.20 mm; flow rate, 20 mL/min; Solvent A: 0.05 N HCl; Solvent B: CH₃CN; injection volume: 2.0 mL (0.05 N HCl/water); gradient: 10→20% B over 30 min; mass-directed fraction collection]. Fractions with the desired MW, eluting at 10.8-12.5 min, were collected and freeze-dried to yield 2.0 mg of pure 32: $^1$H NMR (400 MHz, CD$_3$OD) δ 8.18 (d, J=11.0 Hz, 1H), 4.41-4.31 (m, 2H), 4.32 (s, 2H), 4.24-4.13 (m, 2), 4.08 (br s, 1H), 3.18-2.86 (m, 3H), 3.03 (s, 3H), 2.95 (s, 3H), 2.71-2.57 (m, 1H), 2.54-2.42 (m, 1H), 2.33-2.16 (m, 2H), 1.69-1.57 (m, 1H); MS (ESI) m/z 545.20 (M+H).

Compounds 12-31 and Compounds 33-46 are prepared similarly to Compounds 11 or 32, substituting the appropriate acyl halide for 2-t-Butylaminoacetylchloride in the synthesis of Compound 11 or cyclic amine for azetidine in the synthesis of Compound 32.

Compound 12

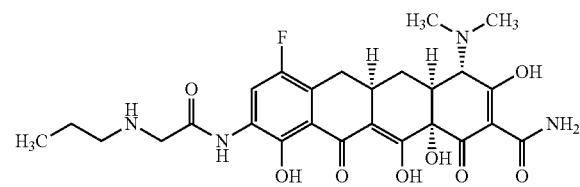

12

$^1$H NMR (400 MHz, CD$_3$OD) δ 8.23 (d, J=11.2 Hz, 1H), 4.08 (s, 3H), 3.17-2.97 (m, 11H), 2.31 (dd, J=14.8, 14.8 Hz, 1H), 2.24 (ddd, J=14.0, 5.2, 2.8 Hz, 1H), 1.79-1.72 (m, 2H), 1.66 (ddd, J=13.6, 13.6, 13.6 Hz, 1H), 1.05 (t, J=7.2 Hz, 3H); MS (ESI) m/z 547.2 (M+H).

Compound 13

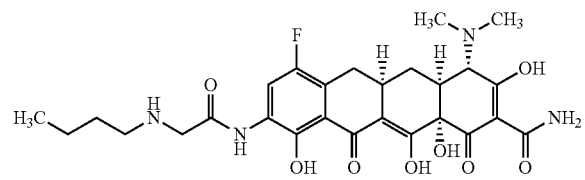

13

$^1$H NMR (400 MHz, CD$_3$OD) δ 8.23 (d, J=11.2 Hz, 1H), 4.08 (s, 3H), 3.16-2.97 (m, 11H), 2.30 (dd, J=14.8, 14.8 Hz, 1H), 2.24 (ddd, J=14.4, 5.2, 2.8 Hz, 1H), 1.75-1.69 (m, 2H), 1.66 (ddd, J=13.6, 13.6, 13.6 Hz, 1H), 1.49-1.41 (m, 2H), 1.01 (t, J=7.2 Hz, 3H); MS (ESI) m/z 561.2 (M+H).

Compound 14

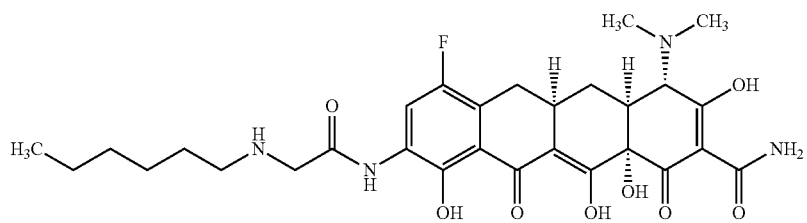

14

$^1$H NMR (400 MHz, CD$_3$OD) δ 8.21 (d, J=11.2 Hz, 1H), 4.08 (s, 1H), 4.06 (s, 2H), 3.16-2.96 (m, 11H), 2.28 (dd, J=14.8, 14.8 Hz, 1H), 2.22 (ddd, J=14.4, 5.2, 2.8 Hz, 1H), 1.77-1.71 (m, 2H), 1.66 (ddd, J=14.0, 14.0, 14.0 Hz, 1H), 1.43-1.35 (m, 6H), 0.93 (t, J=7.2 Hz, 3H); MS (ESI) m/z 589.2 (M+H).

Compound 15

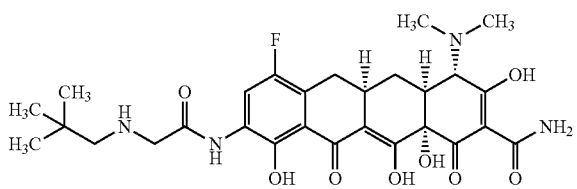

15

$^1$H NMR (400 MHz, CD$_3$OD) δ 8.23 (d, J=10.8 Hz, 1H), 4.09 (s, 2H), 4.07 (s, 1H), 3.15-2.95 (m, 11H), 2.29 (dd, J=14.4, 14.4 Hz, 1H), 2.25 (ddd, J=14.4, 5.2, 2.8 Hz, 1H), 1.66 (ddd, J=13.2, 13.2, 13.2 Hz, 1H), 1.10 (s, 9H); MS (ESI) m/z 575.2 (M+H).

Compound 16

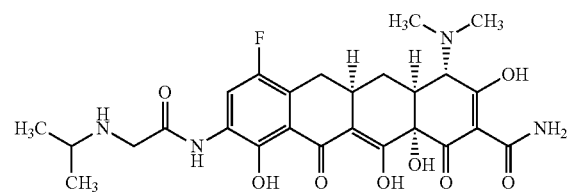

16

$^1$H NMR (400 MHz, CD$_3$OD) δ 8.24 (d, J=11.0 Hz, 1H), 4.08 (s, 2H), 4.01-3.89 (m, 1H), 3.50-3.42 (m, 1H), 3.20-2.84 (m, 9H), 2.30 (at, J=14.7 Hz, 1H), 2.23-2.15 (m, 1H), 1.70-1.58 (m, 1H), 1.37 (d, J=6.7 Hz, 6H); MS (ESI) m/z 547.25 (M+H).

Compound 17

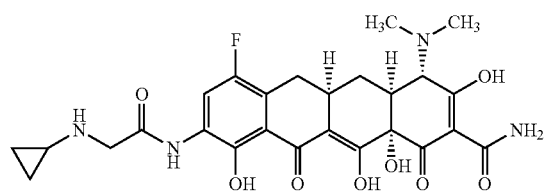

¹H NMR (400 MHz, CD₃OD) δ 8.24 (d, J=11.0 Hz, 1H), 4.20 (s, 2H), 4.09 (br s, 1H), 3.19-3.13 (m, 1H), 3.12-2.89 (m, 2H), 2.89-2.38 (m, 1H), 3.04 (s, 3H), 2.96 (s, 3H), 2.35-2.19 (m, 2H), 1.71-1.59 (m, 1H), 0.95 (br s, 2), 0.94 (br s, 2); MS (ESI) m/z 545.37 (M+H).

Compound 18

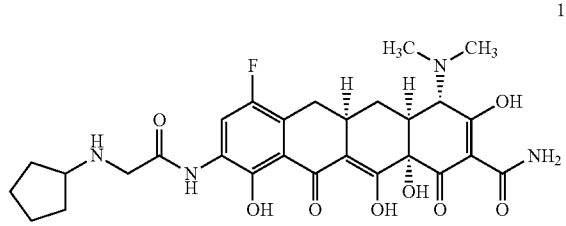

¹H NMR (400 MHz, CD₃OD) δ 8.23 (d, J=10.8 Hz, 1H), 4.09 (s, 3H), 3.68-3.61 (m, 1H), 3.16-2.97 (m, 9H), 2.29 (dd, J=14.4, 14.4 Hz, 1H), 2.25 (ddd, J=14.4, 5.2, 2.8 Hz, 1H), 2.20-2.12 (m, 2H), 1.98-1.91 (m, 2H), 1.75-1.68 (m, 4H), 1.66 (ddd, J=13.6, 13.6, 13.6 Hz, 1H); MS (ESI) m/z 573.1 (M+H).

Compound 19

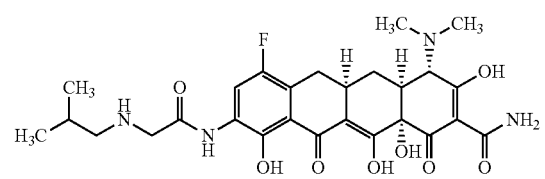

¹H NMR (400 MHz, CD₃OD) δ 8.26 (d, J=11.0 Hz, 1H), 4.09 (br s, 3H), 3.19-2.93 (m, 5H), 3.04 (s, 3H), 2.96 (s, 3H), 2.35-2.26 (m, 1H), 2.25-2.18 (m, 1H), 2.14-2.02 (m, 1H), 1.71-1.59 (m, 1H), 1.07 (d, J=6.7, 6H); MS (ESI) m/z 561.24 (M+H).

Compound 20

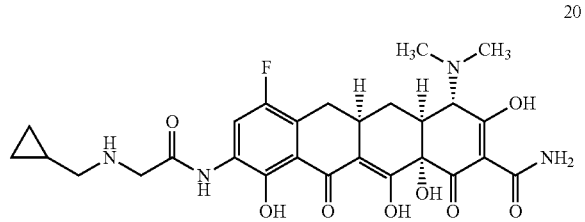

¹H NMR (400 MHz, CD₃OD) δ 8.24 (d, J=11.0 Hz, 1H), 4.11 (s, 2H), 4.08 (br s, 1H), 3.22-2.92 (m, 5H), 3.03 (s, 3H), 2.95 (s, 3H), 2.33-2.24 (m, 1H), 2.24-2.17 (m, 1H), 1.69-1.58 (m, 1H), 1.17-1.07 (m, 1H), 0.77-0.71 (m, 2H), 0.46-0.40 (m, 2H); MS (ESI) m/z 559.23 (M+H).

Compound 21

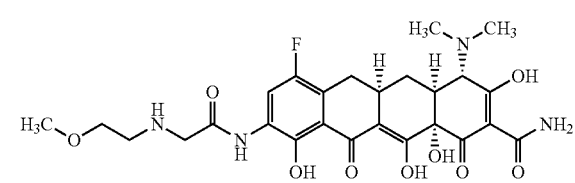

¹H NMR (400 MHz, CD₃OD) δ 8.25 (d, J=11.0 Hz, 1H), 4.12 (s, 2H), 4.09 (s, 1H), 3.72-3.67 (m, 2H), 3.43 (s, 3H), 3.19-2.92 (m, 11H), 2.35-2.18 (m, 2H) 1.71-1.58 (m, 1H); MS (ESI) m/z 563.23 (M+H).

Compound 22

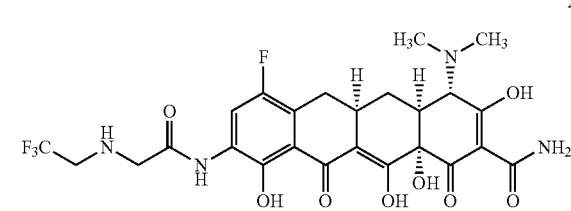

¹H NMR (400 MHz, CD₃OD) δ 8.25 (d, J=11.0 Hz, 1H), 4.22 (s, 2H), 4.14-4.05 (m, 3H), 3.18-2.84 (m, 9H), 2.34-2.17 (m, 2H), 1.70-1.57 (m, 1H); MS (ESI) m/z 587.28 (M+H).

Compound 23

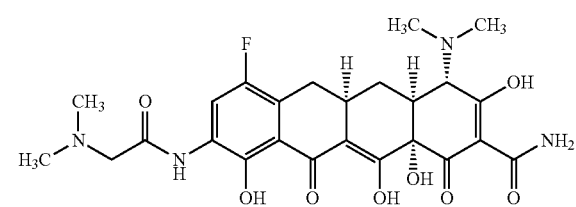

¹H NMR (400 MHz, CD₃OD) δ 8.24 (d, J=11.0 Hz, 1H), 4.24 (s, 2H), 4.09 (s, 1H), 3.14-2.93 (m, 15H), 2.24-2.18 (m, 2H), 1.65 (dt, J=13.4, 11.6 Hz, 1H); MS (ESI) m/z 533.17 (M+H).

Compound 24

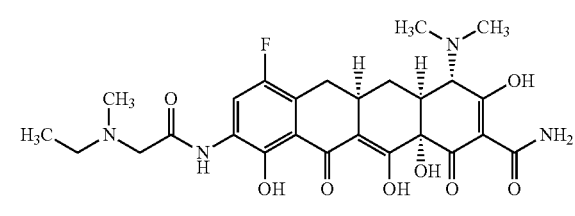

¹H NMR (400 MHz, CD₃OD) δ 8.23 (d, J=10.4 Hz, 1H), 4.29 (d, J=16.5 Hz, 1H), 4.18 (d, J=15.9 Hz, 1H), 4.09 (s, 1H), 3.19-2.89 (m, 14H), 2.36-2.17 (m, 2H), 1.70-1.58 (m, 1H), 1.38 (t, J=7.32 Hz, 3H); MS (ESI) m/z 547.25 (M+H).

Compound 25

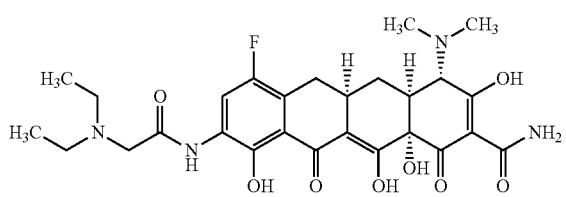

¹H NMR (400 MHz, CD₃OD) δ 8.21 (d, J=10.8 Hz, 1H), 4.25 (s, 2H), 4.10 (s, 1H), 3.35 (t, J=7.2 Hz, 3H), 3.34 (t, J=7.2 Hz, 3H), 3.13-2.99 (m, 9H), 2.31 (dd, J=14.8, 14.8 Hz, 1H), 2.27 (ddd, J=14.8, 5.2, 2.8 Hz, 1H), 1.78-1.74 (m, 2H), 1.68 (ddd, J=13.6, 13.6, 13.6 Hz, 1H), 1.38 (t, J=7.2 Hz, 6H); MS (ESI) m/z 561.2 (M+H).

Compound 26

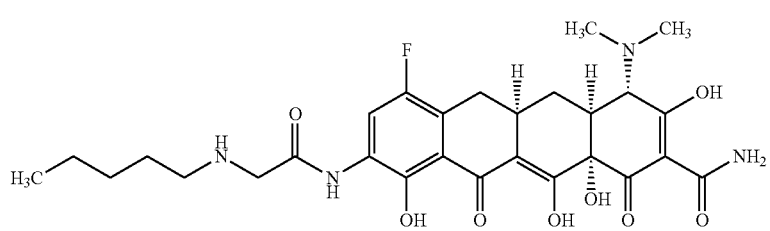

¹H NMR (400 MHz, CD₃OD) δ 8.23 (d, J=11.2 Hz, 1H), 4.10 (s, 3H), 3.16-2.96 (m, 11H), 2.31 (dd, J=14.4, 14.4 Hz, 1H), 2.24 (ddd, J=14.4, 5.2, 2.8 Hz, 1H), 1.78-1.71 (m, 2H), 1.66 (ddd, J=14.0, 14.0, 14.0 Hz, 1H), 1.45-1.38 (m, 4H), 0.98 (t, J=7.2 Hz, 3H); MS (ESI) m/z 575.2 (M+H).

Compound 27

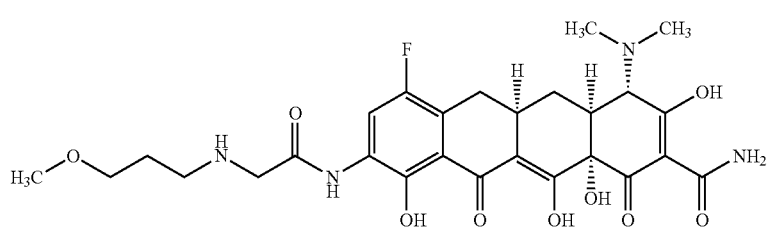

¹H NMR (400 MHz, CD₃OD) δ 8.24 (d, J=10.8 Hz, 1H), 4.09 (s, 3H), 3.59 (t, J=5.6 Hz, 2H), 3.40 (s, 3H), 3.23 (t, J=5.6 Hz, 2H), 3.15-2.94 (m, 9H), 2.32 (dd, J=15.2, 15.2 Hz, 1H), 2.24 (ddd, J=14.0, 5.2, 2.8 Hz, 1H), 2.08-2.02 (m, 2H), 1.66 (ddd, J=15.2, 15.2, 15.2 Hz, 1H); MS (ESI) m/z 577.2 (M+H).

Compound 28

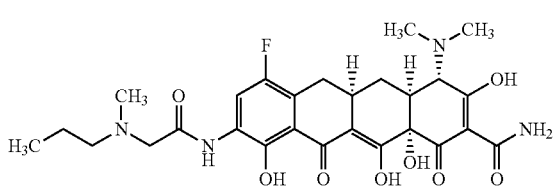

¹H NMR (400 MHz, CD₃OD) δ 8.24 (d, J=10.8 Hz, 1H), 4.32 (d, J=8.0 Hz, 1H), 4.21 (d, J=8.0 Hz, 1H), 4.10 (s, 1H), 3.18-2.99 (m, 9H), 3.01 (s, 3H), 2.33 (dd, J=14.8, 14.8 Hz, 1H), 2.29 (ddd, J=15.2, 5.2, 2.8 Hz, 1H), 1.78-1.74 (m, 2H), 1.88-1.81 (m, 2H), 1.68 (ddd, J=15.6, 15.6, 15.6 Hz, 1H), 1.08 (t, J=7.2 Hz, 3H); MS (ESI) m/z 561.2 (M+H).

Compound 29

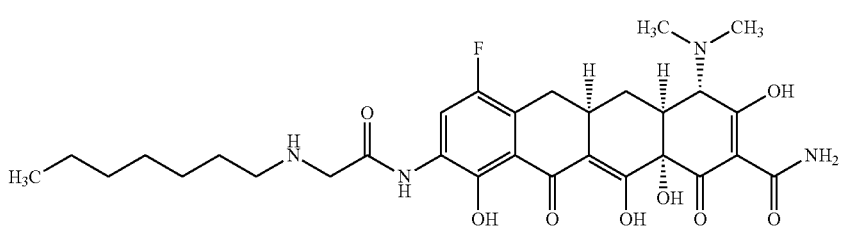

$^1$H NMR (400 MHz, CD$_3$OD) δ 8.25 (d, J=10.8 Hz, 1H), 4.10 (s, 3H), 3.18-2.98 (m, 11H), 2.31 (dd, J=14.8, 14.8 Hz, 1H), 2.26 (ddd, J=14.4, 5.2, 2.8 Hz, 1H), 1.78-1.74 (m, 2H), 1.66 (ddd, J=13.6, 13.6, 13.6 Hz, 1H), 1.42-1.30 (m, 8H), 0.94 (t, J=6.8 Hz, 3H); MS (ESI) m/z 603.2 (M+H).

Compound 30

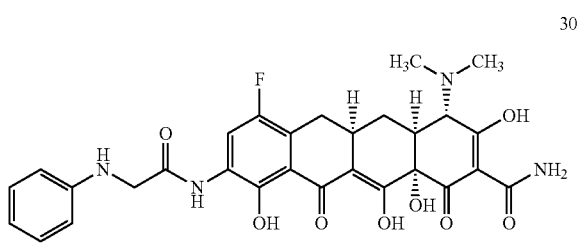

$^1$H NMR (400 MHz, CD$_3$OD) δ 8.32 (d, J=10.4 Hz, 1H), 7.38-7.34 (m, 2H), 7.10-7.06 (m, 3H), 4.17 (s, 2H), 4.10 (s, 1H), 3.18-2.99 (m, 11H), 2.29 (dd, J=15.6, 15.6 Hz, 1H), 2.25 (ddd, J=14.8, 5.2, 2.8 Hz, 1H), 1.66 (ddd, J=14.8, 14.8, 14.8 Hz, 1H); MS (ESI) m/z 581.1 (M+H).

Compound 31

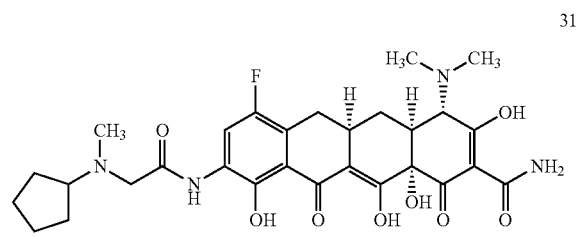

$^1$H NMR (400 MHz, CD$_3$OD) δ 8.25 (d, J=10.8 Hz, 1H), 4.36 (d, J=8.0 Hz, 1H), 4.21 (d, J=8.0 Hz, 1H), 4.10 (s, 1H), 3.68-3.61 (m, 1H), 3.18-2.98 (m, 9H), 3.00 (s, 3H), 2.29 (dd, J=14.4, 14.4 Hz, 1H), 2.20-2.10 (m, 3H), 1.96-1.89 (m, 2H), 1.78-1.68 (m, 4H), 1.66 (ddd, J=14.4, 14.4, 14.4 Hz, 1H); MS (ESI) m/z 587.2 (M+H).

Compound 33

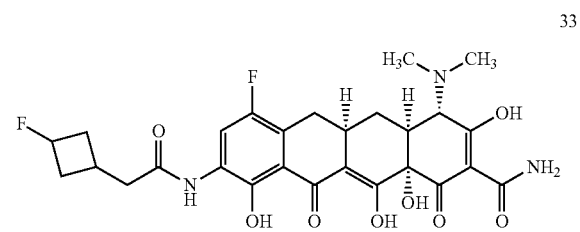

$^1$H NMR (400 MHz, CD$_3$OD) δ 8.20 (d, J=11.0 Hz, 1H), 5.54-5.33 (m, 2H), 4.71-4.37 (m, 4H), 4.40 (s, 2H), 4.06 (br s, 1H), 3.17-2.92 (m, 3H), 2.99 (s, 6H), 2.33-2.24 (m, 1H), 2.23-2.16 (m, 1H), 1.70-1.58 (m, 1H); MS (ESI) m/z 563.20 (M+H).

Compound 34

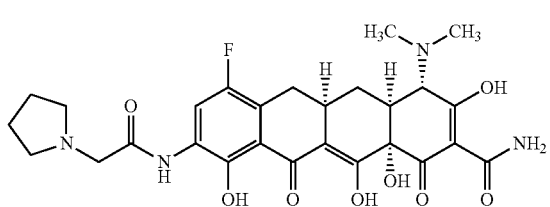

$^1$H NMR (400 MHz, CD$_3$OD) δ 8.22 (d, J=11.0 Hz, 1H), 4.33 (s, 2H), 4.10 (s, 1H), 3.83-3.72 (m, 2H), 3.25-2.89 (m, 12H), 2.32-2.00 (m, 6H), 1.69-1.56 (m, 1H); MS (ESI) m/z 559.39 (M+H).

Compound 35

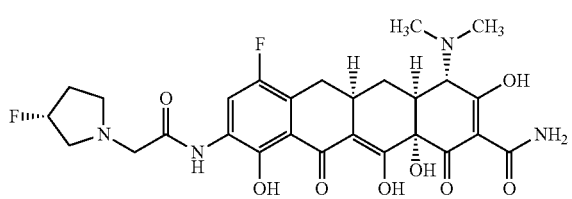

$^1$H NMR (400 MHz, CD$_3$OD) δ 8.25 (d, J=11.0 Hz, 1H), 5.54-5.31 (m, 1H), 4.39-4.20 (m, 2H), 4.09-4.01 (m, 1H), 3.40-3.30 (m, 2H), 3.09-2.89 (m, 12H), 2.50-2.34 (m, 2H), 2.34-2.25 (m, 1H), 2.24-2.16 (m, 1H), 1.71-1.58 (m, 1H); MS (ESI) m/z 577.32 (M+H).

Compound 36

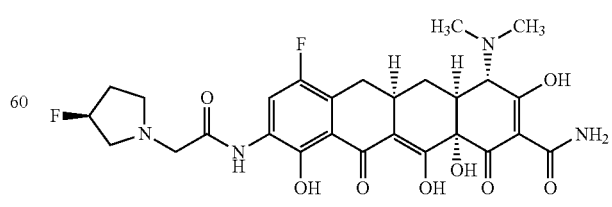

$^1$H NMR (400 MHz, CD$_3$OD) δ 8.23 (d, J=10.4 Hz, 1H), 5.57-5.37 (m, 1H), 4.47-4.33 (m, 2H), 4.15-3.87 (m, 2H), 3.72-3.40 (m, 1H), 3.17-2.83 (m, 12H), 2.55-2.34 (m, 2H), 2.33-2.18 (m, 2H), 1.69-1.57 (m, 1H); MS (ESI) m/z 577.37 (M+H).

Compound 37

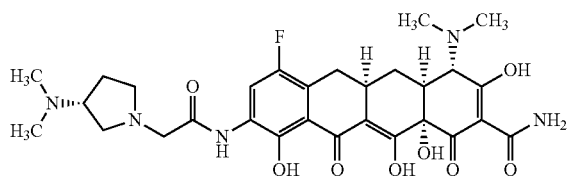

37

¹H NMR (400 MHz, CD₃OD) δ 8.28 (d, J=10.7 Hz, 1H), 4.08 (s, 1H), 4.00-3.91 (m, 2H), 3.09-2.57 (m, 18H), 3.26-3.18 (m, 3H), 2.49-2.34 (m, 2H), 2.35-2.06 (m, 2H), 1.72-1.59 (m, 1H); MS (ESI) m/z 602.37 (M+H).

Compound 38

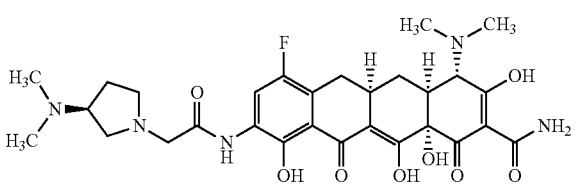

38

¹H NMR (400 MHz, CD₃OD) δ 8.24 (d, J=11.0 Hz, 1H), 4.46-4.32 (m, 2H), 4.26-4.16 (m, 1H), 4.08 (s, 2H), 4.00-3.72 (m, 2H), 3.18-2.91 (m, 16H), 2.68-2.56 (m, 1H), 2.51-2.39 (m, 1H), 2.34-2.24 (m, 1H), 2.23-2.17 (m, 1H), 1.70-1.57 (m, 1H); MS (ESI) m/z 602.37 (M+H).

Compound 39

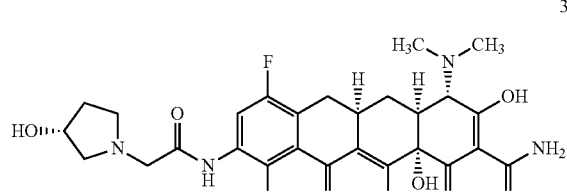

39

¹H NMR (400 MHz, CD₃OD) δ 8.23 (d, J=11.0 Hz, 1H), 4.62-4.54 (m, 1H), 4.48-4.24 (m, 2H), 4.08 (s, 1H), 3.99-3.69 (m, 3H), 3.50-3.40 (m, 1H), 3.17-2.90 (m, 9H), 2.44-2.11 (m, 4H), 2.10-2.00 (m, 1H), 1.69-1.56 (m, 1H); MS (ESI) m/z 575.27 (M+H).

Compound 40

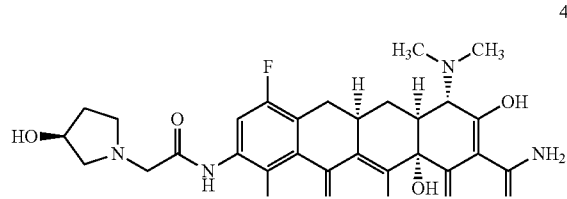

40

¹H NMR (400 MHz, CD₃OD) δ 8.23 (d, J=11.0 Hz, 1H), 4.62-4.54 (m, 1H), 4.50-4.38 (m, 1H), 4.37-4.27 (m, 1H), 4.10 (s, 1H), 3.99-3.70 (m, 3H), 3.50-3.40 (m, 1H), 3.24-2.84 (m, 9H), 2.40-2.11 (m, 4H), 2.10-2.01 (m, 1H), 1.70-1.57 (m, 1H); MS (ESI) m/z 575.33 (M+H).

Compound 41

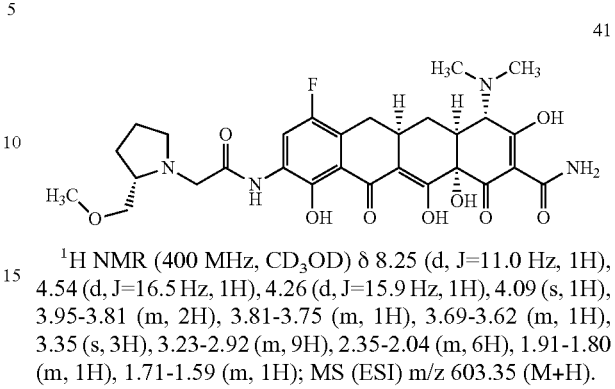

41

¹H NMR (400 MHz, CD₃OD) δ 8.25 (d, J=11.0 Hz, 1H), 4.54 (d, J=16.5 Hz, 1H), 4.26 (d, J=15.9 Hz, 1H), 4.09 (s, 1H), 3.95-3.81 (m, 2H), 3.81-3.75 (m, 1H), 3.69-3.62 (m, 1H), 3.35 (s, 3H), 3.23-2.92 (m, 9H), 2.35-2.04 (m, 6H), 1.91-1.80 (m, 1H), 1.71-1.59 (m, 1H); MS (ESI) m/z 603.35 (M+H).

Compound 42

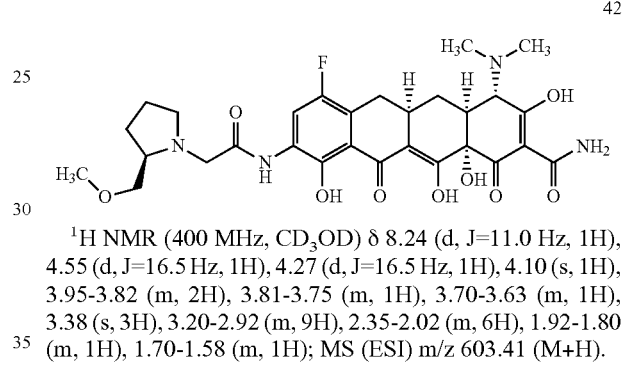

42

¹H NMR (400 MHz, CD₃OD) δ 8.24 (d, J=11.0 Hz, 1H), 4.55 (d, J=16.5 Hz, 1H), 4.27 (d, J=16.5 Hz, 1H), 4.10 (s, 1H), 3.95-3.82 (m, 2H), 3.81-3.75 (m, 1H), 3.70-3.63 (m, 1H), 3.38 (s, 3H), 3.20-2.92 (m, 9H), 2.35-2.02 (m, 6H), 1.92-1.80 (m, 1H), 1.70-1.58 (m, 1H); MS (ESI) m/z 603.41 (M+H).

Compound 43

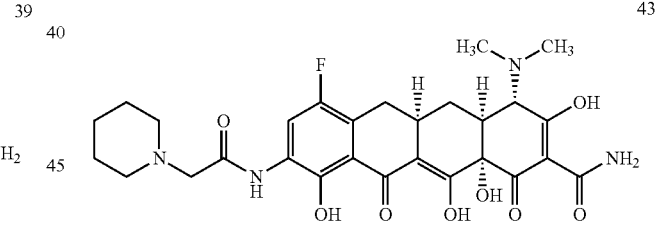

43

¹H NMR (400 MHz, CD₃OD) δ 8.22 (d, J=11.0 Hz, 1H), 4.19 (s, 2H), 4.09 (s, 1H), 3.65-3.58 (m, 2H), 3.19-2.92 (m, 10H), 2.34-2.18 (m, 2H), 2.02-1.79 (m, 6H), 1.69-1.50 (m, 2H); MS (ESI) m/z 573.35 (M+H).

Compound 44

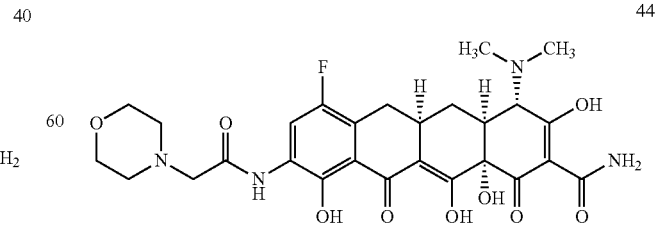

44

¹H NMR (400 MHz, CD₃OD) δ 8.24 (d, J=11.0 Hz, 1H), 4.28 (s, 2H), 4.03-4.00 (m, 2H), 3.94-3.81 (m, 2H), 3.68-.3.55

(m, 2H), 3.20-2.88 (m, 12H), 2.36-2.18 (m, 2H), 1.71-1.57 (m, 1H); MS (ESI) m/z 575.37 (M+H).

Compound 45

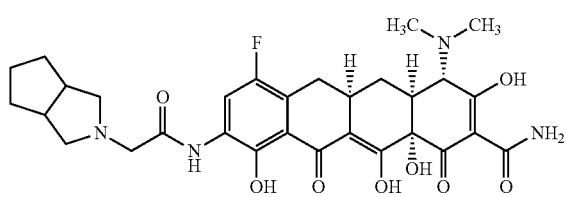

45

¹H NMR (400 MHz, CD₃OD, 2:1 mixture of diastereomers) δ 8.25 (d+d, J=11.0 Hz, 1H), 4.29, 4.24 (s+s, 2H), 4.08 (s+s, 1H), 4.01-3.92 (m+m, 3H), 3.20-2.62 (m+m, 13H), 2.35-2.16 (m+m, 3H), 1.83-1.46 (m+m, 5H); MS (ESI) m/z 599.36 (M+H).

Compound 46

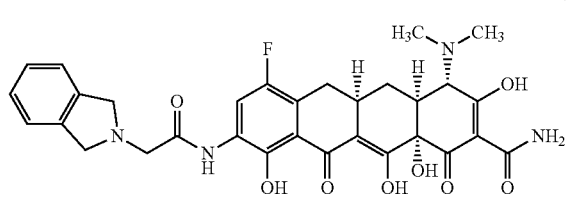

46

¹H NMR (400 MHz, CD₃OD) δ 8.29 (d, J=11.0 Hz, 1H), 7.41 (s, 5H), 4.50-4.37 (m, 2H), 4.05 (s, 1H), 3.95-3.81 (m, 2H), 3.40-3.37 (m, 1H), 3.24-3.15 (m, 3H), 3.10-2.70 (m, 9H), 2.36-2.25 (m, 1H), 2.25-2.16 (m, 1H), 1.72-1.59 (m, 1H); MS (ESI) m/z 607.34 (M+H).

Compound 47

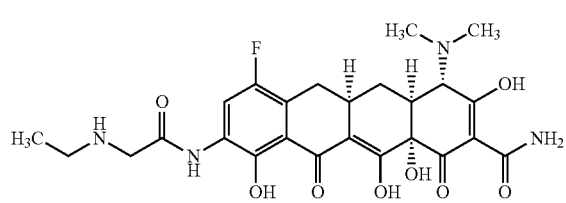

47

¹H NMR (400 MHz, CD₃OD) δ 8.15 (d, J=10.8 Hz, 1H), 4.00 (s, 1H), 3.99 (s, 2H), 3.10-2.87 (m, 11H), 2.32-2.12 (m, 2H), 1.59-1.51 (m, 1H), 1.26 (t, J=7.2 Hz, 3H); MS (ESI) m/z 533.1 (M+H).

Compound 48

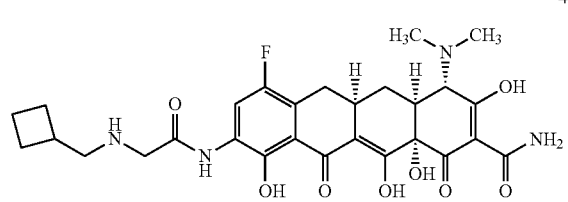

48

¹H NMR (400 MHz, CD₃OD) δ 8.15 (d, J=11.2 Hz, 1H), 4.00 (s, 1H), 3.96 (s, 2H), 3.08-2.87 (m, 11H), 2.70-2.61 (m, 1H), 2.23-2.09 (m, 4H), 1.97-1.75 (m, 4H), 1.59-1.51 (m, 1H); MS (ESI) m/z 572.2 (M+H).

Compound 49

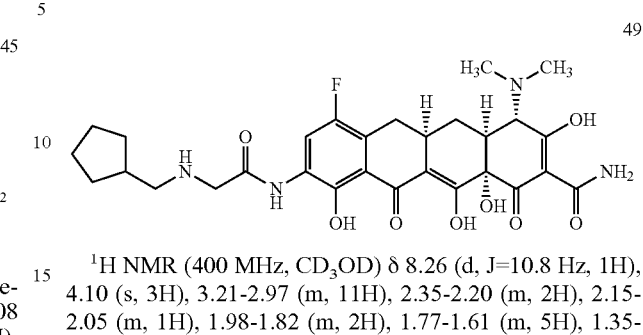

49

¹H NMR (400 MHz, CD₃OD) δ 8.26 (d, J=10.8 Hz, 1H), 4.10 (s, 3H), 3.21-2.97 (m, 11H), 2.35-2.20 (m, 2H), 2.15-2.05 (m, 1H), 1.98-1.82 (m, 2H), 1.77-1.61 (m, 5H), 1.35-1.26 (m, 2 µl); MS (ESI) m/z 587.1 (M+H).

Compound 50

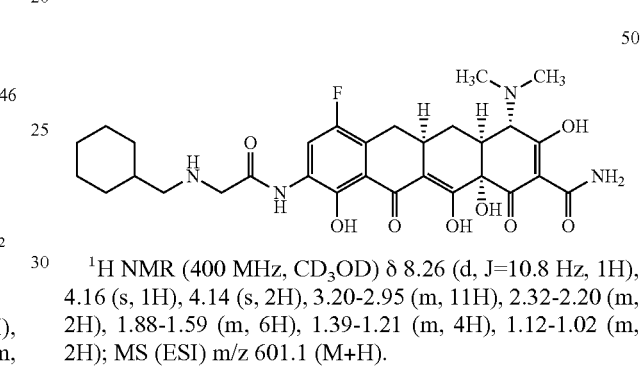

50

¹H NMR (400 MHz, CD₃OD) δ 8.26 (d, J=10.8 Hz, 1H), 4.16 (s, 1H), 4.14 (s, 2H), 3.20-2.95 (m, 11H), 2.32-2.20 (m, 2H), 1.88-1.59 (m, 6H), 1.39-1.21 (m, 4H), 1.12-1.02 (m, 2H); MS (ESI) m/z 601.1 (M+H).

Compound 51

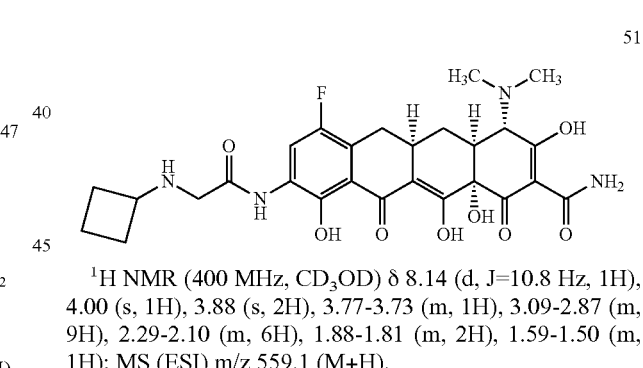

51

¹H NMR (400 MHz, CD₃OD) δ 8.14 (d, J=10.8 Hz, 1H), 4.00 (s, 1H), 3.88 (s, 2H), 3.77-3.73 (m, 1H), 3.09-2.87 (m, 9H), 2.29-2.10 (m, 6H), 1.88-1.81 (m, 2H), 1.59-1.50 (m, 1H); MS (ESI) m/z 559.1 (M+H).

Compound 52

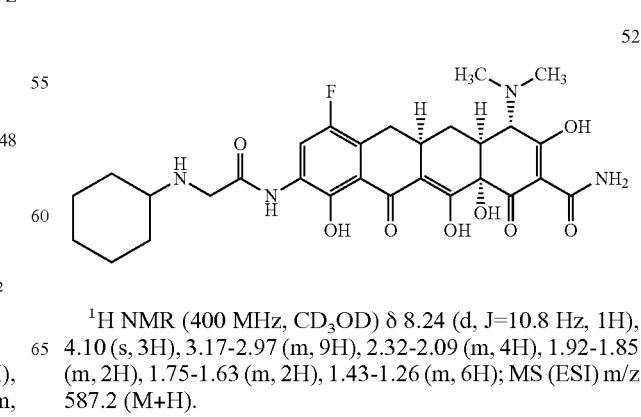

52

¹H NMR (400 MHz, CD₃OD) δ 8.24 (d, J=10.8 Hz, 1H), 4.10 (s, 3H), 3.17-2.97 (m, 9H), 2.32-2.09 (m, 4H), 1.92-1.85 (m, 2H), 1.75-1.63 (m, 2H), 1.43-1.26 (m, 6H); MS (ESI) m/z 587.2 (M+H).

Compound 53

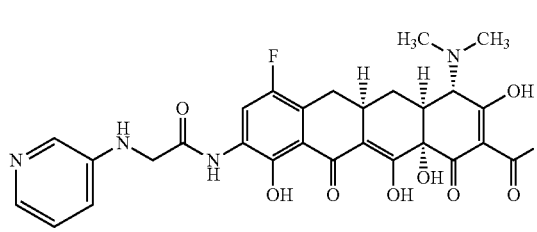

¹H NMR (400 MHz, CD₃OD) δ 8.20 (d, J=11.2 Hz, 1H), 8.16 (d, J=2.4 Hz, 1H), 8.06 (d, J=5.2 Hz, 1H), 7.85-7.78 (m, 2H), 4.27 (s, 2H), 4.11 (s, 1H), 3.18-2.98 (m, 9H), 2.32-2.21 (m, 2H), 1.70-1.60 (m, 1H); MS (ESI) m/z 582.2 (M+H)

Compound 54

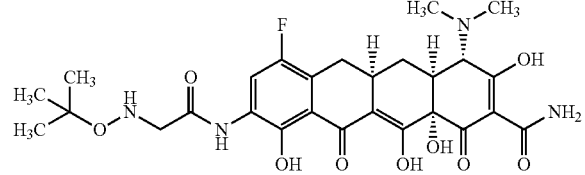

¹H NMR (400 MHz, CD₃OD) δ 8.24 (d, J=11.0 Hz, 1H), 4.31 (s, 2H), 4.11 (s, 1H), 3.22-2.88 (m, 9H), 2.36-2.16 (m, 2H), 1.70-1.56 (m, 1H), 1.44 (s, 9H); MS (ESI) m/z 577.41 (M+H).

Compound 55

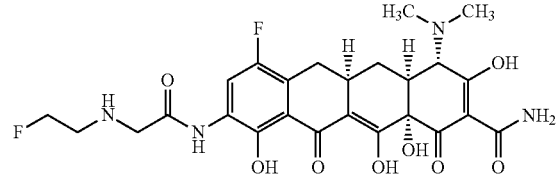

¹H NMR (400 MHz, CD₃OD) δ 8.15 (d, J=10.8 Hz, 1H), 4.65 (t, J=4.8 Hz, 2H), 4.08 (s, 2H), 4.00 (s, 1H), 3.45 (t, J=4.4 Hz, 1H), 3.38 (t, J=5.6 Hz, 1H), 3.20-2.87 (m, 9H), 2.25-2.09 (m, 2H), 1.59-1.50 (m, 1H); MS (ESI) m/z 551.0 (M+H).

Compound 56

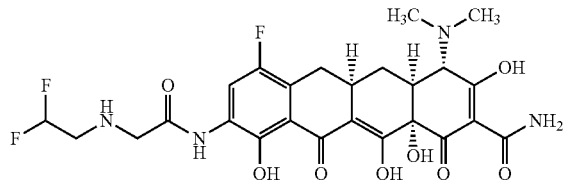

¹H NMR (400 MHz, CD₃OD) δ 8.25 (d, J=11.2 Hz, 1H), 6.39 (tt, J=53.6, 3.2 Hz, 1H), 4.24 (s, 2H), 4.13 (s, 1H), 3.71 (td, J=15.2, 2.8 Hz, 2H), 3.19-2.91 (m, 9H), 2.33-2.24 (m, 2H), 1.70-1.60 (m, 1H); MS (ESI) m/z 569.0 (M+H).

Compound 57

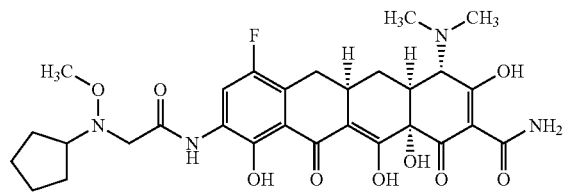

¹H NMR (400 MHz, CD₃OD) δ 8.21 (d, J=10.8 Hz, 1H), 4.01 (s, 1H), 3.85 (s, 2H), 3.73 (s, 3H), 3.59-3.51 (m, 1H), 3.12-2.87 (m, 9H), 2.23-2.12 (m, 2H), 1.88-1.50 (m, 9H); MS (ESI) m/z 559.1 (M+H).

Compound 58

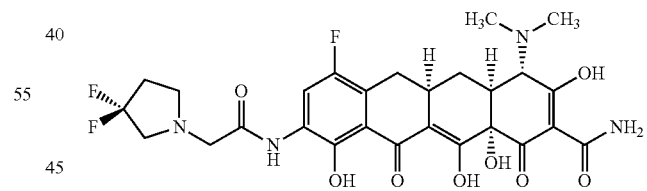

¹H NMR (400 MHz, CD₃OD) δ 8.24 (d, J=10.8 Hz, 1H), 4.48 (s, 2H), 4.12 (s, 1H), 4.10-4.07 (m, 2H), 3.93-3.86 (m, 2H), 3.19-2.90 (m, 9H), 2.79-2.67 (m, 2H), 2.37-2.21 (m, 2H), 1.59-1.51 (m, 1H); MS (ESI) m/z 595.0 (M+H).

Example 2

Synthesis of Compounds of Structural Formula (I), Wherein R¹ and R² Taken Together with the Nitrogen to which they are Bonded Form a Monocyclic or Bicyclic Heteroaryl

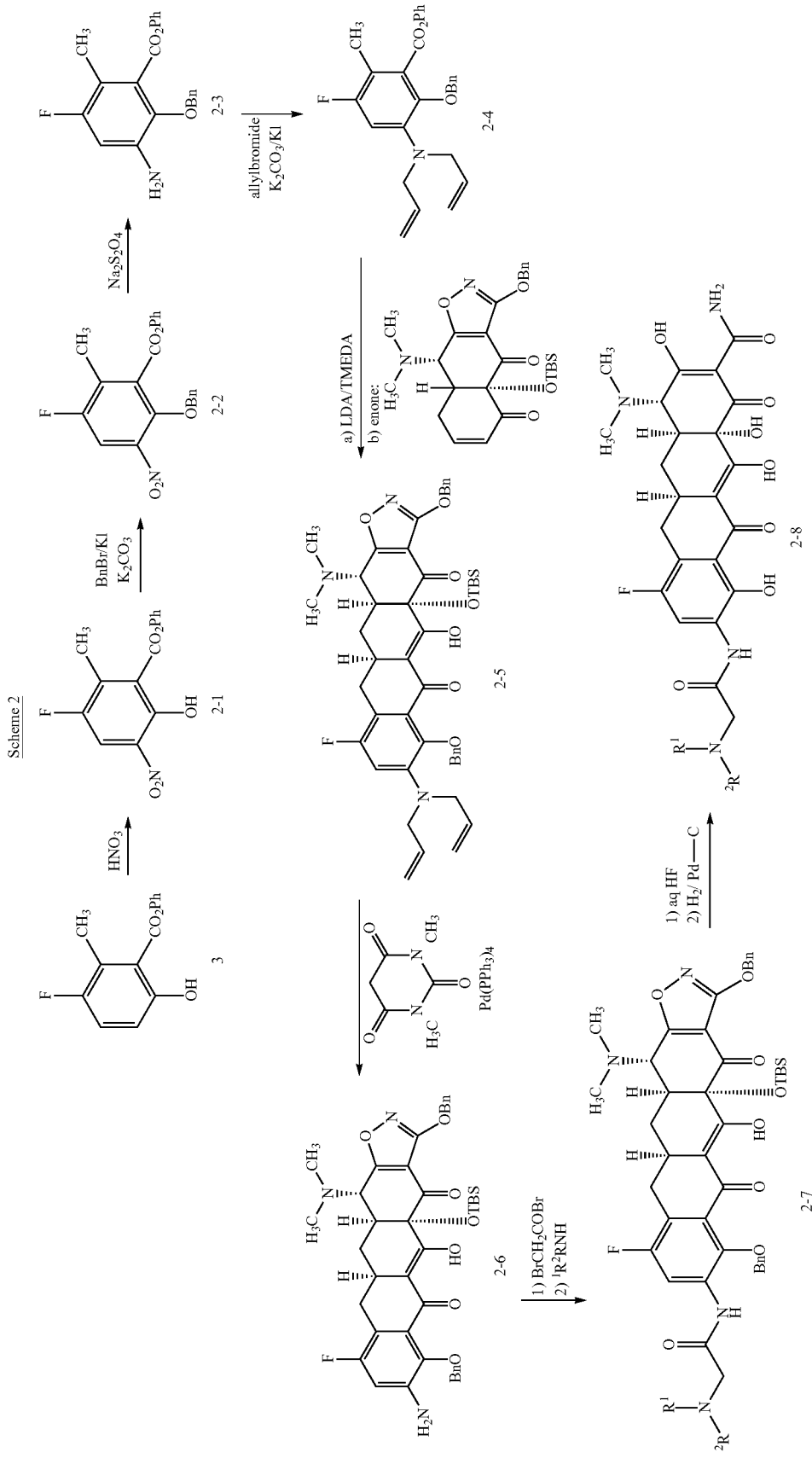

The following compounds were prepared according to Scheme 2.

Compound 2-1

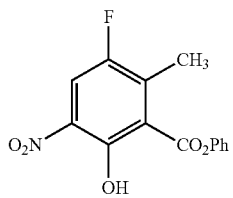

To a 250 mL round bottom flask was added compound 3 (14.47 g, 56.30 mmol, 1.0 equiv, crude), tetrabutylammonium bromide (0.90 g, 2.80 mmol, 0.05 equiv), 1,2-dichloroethane (60 mL), and water (60 mL). The clear bi-layer was cooled in a 20° C. water bath. Nitric acid (7.2 mL, 70 wt %, 112.60 mmol, 2.0 equiv) was added. After the addition, the reaction temperature slowly rose to 26° C. The reaction was stirred at room temperature overnight (19 hrs). TLC (heptane/EtOAc=9.5/0.5) showed the reaction was complete. The organic layer was separated, washed with water (60 mL×2) and brine, and dried over anhydrous sodium sulfate. The solvent was removed to give compound 2-1 as a brown oil, which solidified on standing (17.71 g, quantitative). The crude product was used directly for the next step.

Compound 2-2

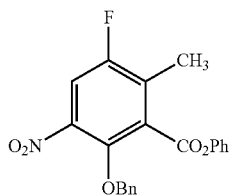

To a 250 mL round bottom flask was added compound 2-1 (17.7 g, 56.30 mmol 1.0 equiv), acetone (177 mL), anhydrous potassium carbonate (15.6 g, 113.00 mmol, 2.0 equiv), and potassium iodide (0.47 g, 2.80 mmol, 0.05 equiv). To the stirred suspension at room temperature was added benzyl bromide (7.03 mL, 59.10 mmol, 1.05 equiv). The suspension was then heated to 56° C. for 4 hrs. TLC (heptane/EtOAc=9/1) showed the reaction was complete. The solid was removed by filtration and washed with acetone (30 mL). The filtrated was concentrated to give a paste. The paste was partitioned between methyl t-butyl ether (MTBE, 120 mL) and water (80 mL). The organic layer was washed with water (80 mL) and brine, dried over anhydrous sodium sulfate, and concentrated to give compound 2-2 as a brown oil (21.09 g, 98%). The crude product was used directly for the next step.

Compound 2-3

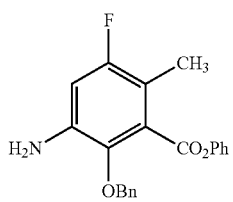

To a 1 L round bottom flask was added compound 2-2 (21.08 g, 55.40 mmol, 1.0 equiv) and THF (230 mL). The solution was cooled in a cold water bath to 10° C. To another 500 mL round bottom flask containing water (230 mL), sodium hydrosulfite ($Na_2S_2O_4$, 56.7 g, 276.80 mmol, 5.0 equiv) was added slowly with stirring. The aqueous solution of sodium hydrosulfite was added to the THF solution of compound 2-2. The temperature quickly rose from 10° C. to 20.4° C. after the addition. The yellow suspension was stirred while the cold water bath slowly warmed up to room temperature overnight to give an orange cloudy solution. The reaction temperature during this period was between 15° C. to 19° C. TLC (heptane/EtOAc=9/1) showed the reaction was complete. The orange cloudy solution was diluted with EtOAc (460 mL). The organic layer was washed with water (150 mL×2) and brine, dried over anhydrous sodium sulfate, and concentrated under reduced pressure to give the crude product as a brown oil. The crude product was purified by flash silica gel column eluted with heptane/EtOAc 9/1 to yield the desired product 2-3 (15.83 g, 80%, 3 steps).

Compound 2-4

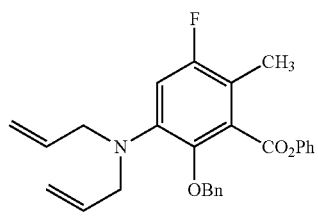

To an NMP solution (50 mL) aniline 2-3 (10.02 g, 28.5 mmol, 1 equiv) was added allyl bromide (7.65 mL, 85.5 mmol, 3 equiv) and potassium carbonate (11.79 g, 85.5 mmol, 3 equiv). Potassium iodide (994.8 mg, 6 mmol, 0.2 equiv) was added and the reaction mixture was placed under nitrogen and heated to 100° C. After 16 h, the reaction was cooled, diluted with water (60 mL), and extracted with EtOAc (75 mL, then 2×50 mL). The combined organic extracts were washed with water (2×35 mL), were dried ($Na_2SO_4$), filtered, and concentrated to yield the crude product. Purification via flash column chromatography on silica gel (RediSep, 125 g, gradient 1-6% EtOAc in hexanes) gave 10.97 g of pure 2-4 (89%): $^1$H NMR (400 MHz, $CDCl_3$) δ 7.42-7.30 (m, 7H), 7.42-7.20 (m, 1H), 7.00 (d, J=8.5 Hz, 2H), 6.72 (d, J=11.0 HZ, 1H), 5.77-5.70 (m, 2H), 5.20-5.12 (m, 6H), 3.81 (d, J=6.1 Hz, 4H), 2.26 (s, 3H); MS (ESI) m/z 432.34 (M+H).

Compound 2-5

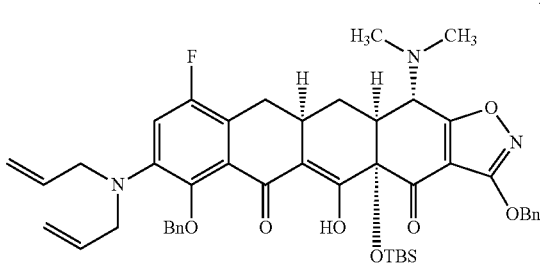

A THF solution (6.5 mL) of 2-4 (875 mg, 2.03 mmol, 1.25 equiv) was added to a freshly-prepared solution of LDA in THF (0.051 M, 2.03 mmol, 40 mL, 1.25 equiv) and TMEDA (304 μL, 2.03 mmol, 1.25 equiv) at −78° C. The reaction was stirred at −78° C. for 15 min. A THF solution (6.5 mL) of enone (784 mg, 1.62 mmol, 1.0 equiv) was added to the reaction mixture dropwise, followed by addition of LHMDS solution (1.0 M in THF, 2.03 mL, 2.03 mmol, 1.25 equiv). The reaction was stirred from −78° C. to −10° C. for 1 h, quenched with saturated $NH_4Cl$ (6 mL), and warmed to 25° C. The solution was poured into saturated NH₄Cl (20 mL) and extracted with EtOAc (2×75 mL). The combined EtOAc extracts were dried (Na₂SO₄), filtered, and concentrated to yield the crude product. Preparative reverse phase HPLC purification on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4×3.6-4.2 mL (CH₃CN); gradient: 88-100% B over 12 min; mass-directed fraction collection]. Fractions with the desired MW, eluting at 6.6-10.6 min, were collected and lyophilized to give 552 mg of pure 2-5 (41%): ¹H NMR (400 MHz, CDCl₃) δ 16.22 (s, 1H), 7.49-7.47 (m, 4H), 7.37-7.31 (m, 6H), 6.80 (d, J=11.0 Hz, 1H), 5.76-5.64 (m, 2H), 5.35 (s, 2H), 5.17-5.11 (m, 4H), 4.98 (d, J=9.2, 1H), 4.87 (d, J=9.8 Hz, 1H), 3.96 (m, J=10.4 Hz, 1H), 3.83-3.71 (m, 4H), 3.14 (dd, J=14.7, 4.3 Hz, 1H), 3.0-2.87 (m, 1H), 2.55-2.35 (m, 9H), 2.11 (d, J=14.7 Hz, 1H), 0.82 (s, 9H), 0.26 (s, 3H), 0.13 (s, 3H); MS (ESI) m/z 820.55 (M+H).

Compound 2-6

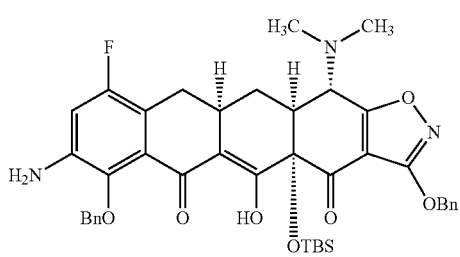

2-6

A solution of 2-5 (550 mg, 0.671 mmol, 1.0 equiv) in degassed CH₂Cl₂ (2.5 mL, with 1 and 1.5 mL rinse) was added under nitrogen via syringe to a flame-dried flask containing N,N-dimethylbarbituric acid (324 mg, 2.07 mmol, 3.0 equiv), and Tetrakis(triphenylphosphine)palladium(0) (56.9 mg, 0.0492 mmol, 0.07 equiv). The resulting solution was heated to 35° C. for 4 h, then concentrated to remove the solvent. The resulting crude mixture was purified via preparative reverse phase HPLC on a Waters Autopurification system using a Sunfire Prep C18 OBD column [5 19×50 mm; flow rate, 20 mL/min; Solvent A: H₂O with 0.1% HCO₂H; Solvent B: CH₃CN with 0.1% HCO₂H; injection volume: 3×3.1 mL (CH₃CN); gradient: 80→100% B over 17 min; mass-directed fraction collection]. Fractions with the desired MW, eluting at 6.1-10.1 min, were collected and freeze-dried to give 352 mg of pure 2-6 (71%): ¹H NMR (400 MHz, CDCl₃) δ 16.10 (s, 1H), 7.51-7.43 (m, 4H), 7.9-7.29 (m, 6H), 6.61 (d, J=9.8 Hz, 1H), 5.35 (s, 2H), 4.87 (dd, J=22.6, 10.4 Hz, 2H), 3.96 (d, J=10.4 Hz, 1H), 3.91 (s, 2H), 3.12 (dd, J=15.3, 10.1 Hz, 1H), 3.04-2.92 (m, 1H), 2.55-2.31 (m, 9H), 2.11 (d, J=14.7 Hz, 1H), 0.82 (s, 9H), 0.27 (s, 3H), 0.12 (s, 3H); MS (ESI) m/z 740.44 (M+H).

Compound 59

59

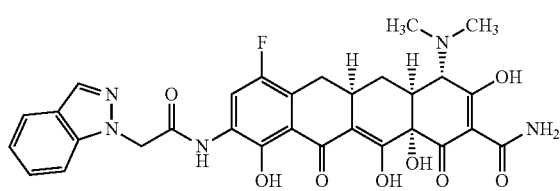

To a solution of aniline 2-6 (30 mg, 0.041 mmol, 1 equiv) in THF (600 μL) was added bromoacetylbromide (3.7 μl, 0.043 mmol, 1.05 equiv). After 15 minutes, indazole (53 mg, 0.45 mmol, 10 equiv) was added. After 15 h the reaction was heated to 80° C. After an additional 26 h, another 20 mg indazole (0.17 mmol, 4 equiv) was added and the reaction heated at 80° C. After 20 h, the solvent was removed in vacuo and the resulting crude mixture dried under vacuum.

The above crude intermediate was transferred to a plastic vial in dioxane (1.2 mL) and an aqueous solution of hydrogen fluoride (50%, 300 μL) was added. After five hours, the reaction solution was diluted with an aqueous solution of K₂HPO₄ (3.6 g in 30 mL) and extracted with EtOAc (2×30 mL). The combined organic layers were dried (Na₂SO₄), filtered, and concentrated to yield the crude product.

Palladium on carbon (10%, 10 mg) was added to solution of the above crude intermediate in dioxane:methanol (1:1, 1 mL). The flask was fitted with a septum and evacuated and back-filled three times with hydrogen gas. Hydrogen gas was bubbled through the reaction solution for two minutes, then the reaction was stirred under an atmosphere (balloon) of hydrogen gas for 1.5 h. The reaction mixture was filtered through celite to remove the palladium catalyst and concentrated under reduced pressure. Preparative reverse phase HPLC purification of the resulting oil was performed on a Waters Autopurification system using a Polymerx 10μ RP-γ 100 R column [30×21.20 mm, 10 micron, solvent A: 0.05N HCl in water, solvent B: CH₃CN; injection volume: 4.8 mL (0.05N HCl in water); gradient elution with 10→60% B over 15 min, then held at 100% for 5 min; mass-directed fraction collection]. Fractions with the desired MW, eluting at 14-14.65 min, were collected and freeze-dried to yield 3.6 mg of compound 59 (15%): ¹H NMR (400 MHz, CD₃OD) δ 8.71 (s, 1 μl), 8.19 (d, J=11.0 Hz, 1H), 7.92-7.90 (m, 1H), 7.72-7.57 (m, 2H), 7/35-7.29 (m, 1H), 5.65 (s, 2H), 4.08 (s, 1H), 3.16-2.92 (m, 9H), 2.31-2.18 (m, 2H), 1.67-1.60 (m, 1H); MS (ESI) m/z 606.41 (M+H).

Compound 60

60

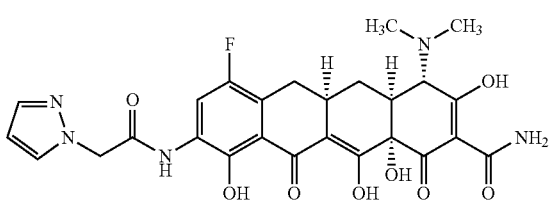

To a solution of aniline 2-6 (22 mg, 0.030 mmol, 1 equiv) in THF (500 μL) was added bromoacetylbromide (2.7 μL, 0.031 mmol, 1.05 equiv). After 30 minutes, pyrazole (36 mg, 0.53 mmol, 18 equiv) was added. After 20 min the reaction was heated to 80° C. for 1.5 h, cooled to room temperature for 15 h, then heated at 80° C. for 4.5 h. The solvent was removed in vacuo and the resulting crude mixture dried under vacuum.

The above crude intermediate was transferred to a plastic vial in acetonitrile (1.0 mL) and an aqueous solution of hydrogen fluoride (50%, 200 μL) was added. After 20 h, the reaction solution was diluted with an aqueous solution of K₂HPO₄ (2.4 g in 20 mL) and extracted with EtOAc (2×25 mL). The combined organic layers were dried (Na₂SO₄), filtered, and concentrated to yield the crude product.

Palladium on carbon (10%, 10 mg) was added to solution of the above crude intermediate in dioxane:methanol (1:1, 1 mL). The flask was fitted with a septum and evacuated and back-filled three times with hydrogen gas. Hydrogen gas was bubbled through the reaction solution for two minutes and the reaction was stirred under an atmosphere (balloon) of hydrogen gas for 1.5 h. The reaction mixture was filtered through celite to remove the palladium catalyst and concentrated under reduced pressure. Preparative reverse phase HPLC purification of the resulting oil was performed on a Waters Autopurification system using a Polymerx 10μ RP-γ 100 R column [30×21.20 mm, 10 micron, solvent A: 0.05N HCl in water, solvent B: CH₃CN; injection volume. 3.0 mL (10% CH₃CN in 0.05N HCl in water); gradient elution with 10→60% B over 10 min, then held at 100% for 5 min; mass-directed fraction collection]. Fractions with the desired MW, eluting at 8.8-10.2 min were collected and freeze-dried. The resulting yellow solid was purified a second time via preparative reverse phase HPLC purification using the above procedure with a gradient over 20 minutes, with the fractions with the desired MW eluting at 10.7-12.4 min were collected and freeze-dried to give 8.2 mg of pure 60 (50%): $^1$H NMR (400 MHz, CD₃OD) δ 8.19 (d, J=11.0 Hz, 1H), 8.05-7.92 (m, 2H), 6.62-6.57 (m, 1H), 5.33 (d, J=4.9 Hz, 2H), 4.08 (s, 1H), 3.16-2.90 (m, 9H), 2.31-2.17 (m, 2H), 1.69-1.55 (m, 1H); MS (ESI) m/z 556.42 (M+H).

Compound 61

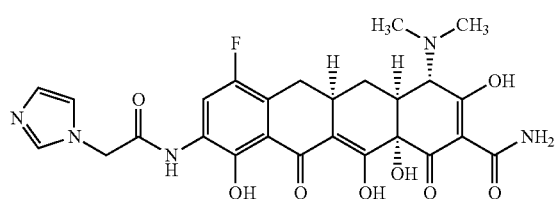

61

To a solution of aniline 2-6 (23 mg, 0.032 mmol, 1 equiv) in THF (500 μL) was added bromoacetylbromide (2.9 μL, 0.034 mmol, 1.05 equiv). After 30 minutes, imidazole (32 mg, 0.47 mmol, 15 equiv) was added and the solution was heated to 80° C. After 2 h, the solution was cooled and the solvent was removed in vacuo.

The above crude intermediate was transferred to a plastic vial in dioxane (1.2 mL) and an aqueous solution of hydrogen fluoride (50%, 200 μL) was added. After 1.5 h, the reaction solution was diluted with an aqueous solution of K₂HPO₄ (2.4 g in 30 mL) and extracted with EtOAc (2×25 mL). The combined organic layers were dried (Na₂SO₄), filtered, and concentrated to yield the crude product.

Palladium on carbon (10%, 8 mg) was added to solution of the above crude intermediate in dioxane:methanol (1:1, 1 mL). The flask was fitted with a septum and evacuated and back-filled three times with hydrogen gas. Hydrogen gas was bubbled through the reaction solution and the reaction was stirred under an atmosphere (balloon) of hydrogen gas for 1.5 h. More palladium catalyst was added and the evacuation and backfilling with hydrogen was performed twice more at 1.5 h and 5 h. The reaction mixture was filtered through celite to remove the palladium catalyst and concentrated under reduced pressure. Preparative reverse phase HPLC purification of the resulting oil was performed on a Waters Autopurification system using a Polymerx 10μ RP-γ 100 R column [30×21.20 mm, 10 micron, solvent A: 0.05N HCl in water, solvent B: CH₃CN; injection volume: 2.8 mL (0.05N HCl in water); gradient elution with 10→60% B over 15 min, then held at 100% for 5 min; mass-directed fraction collection]. Fractions with the desired MW, eluting at 7.0-7.8 min were collected and freeze-dried to give 4.1 mg of pure 61 (23%): $^1$H NMR (400 MHz, CD₃OD) δ 9.02 (s, 1H), 8.17 (d, J=11.0 Hz, 1H), 7.67 (s, 1H), 7.61 (s, 1H), 5.34 (s, 2H), 4.09 (s, 1H), 3.18-2.90 (m, 9H), 2.34-21.7 (m, 2H), 1.71-1.56 (m, 1H); MS (ESI) m/z 556.45 (M+H).

Compound 62

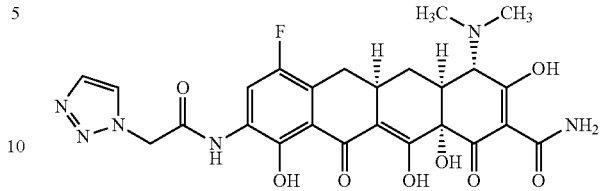

62

To a solution of aniline 2-6 (20.2 mg, 0.027 mmol, 1 equiv) in THF (500 μL) was added bromoacetylbromide (2.5 μL, 0.029 mmol, 1.05 equiv). After 30 minutes, 1H-1,2,3-triazole (31 μL, 0.54 mmol, 20 equiv) was added and the solution was heated to 80° C. After 17 h, an additional 31 μL (20 equiv) of 1H-1,2,3-triazole was added and the solution was heated for 22 h. The solution was cooled and the solvent was removed in vacuo.

The above crude intermediate was transferred to a plastic vial in dioxane (1.0 mL) and an aqueous solution of hydrogen fluoride (50%, 200 μL) was added. After 17 h, the reaction solution was diluted with an aqueous solution of K₂HPO₄ (2.4 g in 20 mL) and extracted with EtOAc (2×25 mL). The combined organic layers were dried (Na₂SO₄), filtered, and concentrated to yield the crude product.

Palladium on carbon (10%, 7 mg) was added to solution of the above crude intermediate in dioxane:methanol (1:1, 1 mL). The flask was fitted with a septum and evacuated and back-filled three times with hydrogen gas. Hydrogen gas was bubbled through the reaction solution and the reaction was stirred under an atmosphere (balloon) of hydrogen gas for 1.5 h. The reaction mixture was filtered through celite to remove the palladium catalyst and concentrated under reduced pressure. Preparative reverse phase HPLC purification of the resulting oil was performed on a Waters Autopurification system using a Polymerx 10μ RP-γ 100 R column [30×21.20 mm, 10 micron, solvent A: 0.05N HCl in water, solvent B: CH₃CN; injection volume: 2.5 mL (0.05N HCl in water); gradient elution with 10→60% B over 15 min, then held at 100% for 5 min; mass-directed fraction collection]. Fractions with the desired MW, eluting at 9.25-10.5 min were collected and freeze-dried. Purification was performed a second time as above and the fractions with the desired MW, eluting at 9.75-10.25 min were collected and freeze-dried to give 1.5 mg of pure 62 (10%): $^1$H NMR (400 MHz, CD₃OD) δ 8.24 (s, 1H), 8.17 (d, J=11.0 Hz, 1H), 8.00 (s, 1H), 5.57 (s, 2H), 4.09 (s, 1H), 3.16-2.92 (m, 9H), 2.34-2.16 (m, 2H), 1.71-1.67 (m, 1H); MS (ESI) m/z 557.44 (M+H).

Compound 63

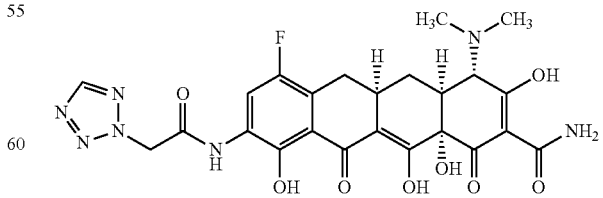

63

To a solution of aniline 2-6 (16.7 mg, 0.023 mmol, 1 equiv) in THF (500 μL) was added bromoacetylbromide (2.0 μL, 0.024 mmol, 1.05 equiv). After 20 minutes, a tetrazole solution (0.45M in CH₃CN, 500 μL, 0.23 mmol, 10 equiv) was added and the solution was heated to 80° C. After 4 h, potassium carbonate (35 mg, 0.25 mmol, 11 equiv) was added and the reaction heated for 35 minutes. The solution was cooled and filtered through celite, and the solvent was removed in vacuo.

The above crude intermediate was transferred to a plastic vial in dioxane (1.0 mL) and an aqueous solution of hydrogen fluoride (50%, 200 µL) was added. After 18 h, the reaction solution was diluted with an aqueous solution of $K_2HPO_4$ (2.4 g in 20 mL) and extracted with EtOAc (2×25 mL). The combined organic layers were dried ($Na_2SO_4$), filtered, and concentrated to yield the crude product.

Palladium on carbon (10%, 7 mg) was added to solution of the above crude intermediate in dioxane:methanol (1:1, 1 mL). The flask was fitted with a septum and evacuated and back-filled three times with hydrogen gas. Hydrogen gas was bubbled through the reaction solution and the reaction was stirred under an atmosphere (balloon) of hydrogen gas for 1 h.

ond time as above with the gradient extended over 20 min. Fractions with the desired MW, eluting at 13.7-14.5 min were collected and freeze-dried to give 1.6 mg of pure 63 (13%): $^1$H NMR (400 MHz, $CD_3OD$) δ 8.78 (s, 1H), 8.14 (d, J=11.0 Hz, 1H), 5.78 (s, 2H), 4.07 (s, 1H), 3.17-2.81 (m, 9H), 2.36-2.16 (m, 2H), 1.70-1.52 (m, 1H); MS (ESI) m/z 558.43 (M+H).

Example 3

Synthesis of Compounds of Structural Formula (A), Wherein X is hydrogen and Y is —NH—C(O)-heterocyclyl, —NH—C(O)-heteroaryl —NH—C(O)—$C(R^D)(R^E)]_{0-1}$—$NR^A)(R^B)$, —NH—C(O)-carbocyclyl, —NH—C(O)-aryl, —NH—$SO_2$—($C_1$-$C_6$) alkyl, —NH—$SO_2$-carbocyclyl, —NH—$SO_2$-aryl, —NH—$SO_2$-heterocyclyl or —NH—$SO_2$-heteroaryl

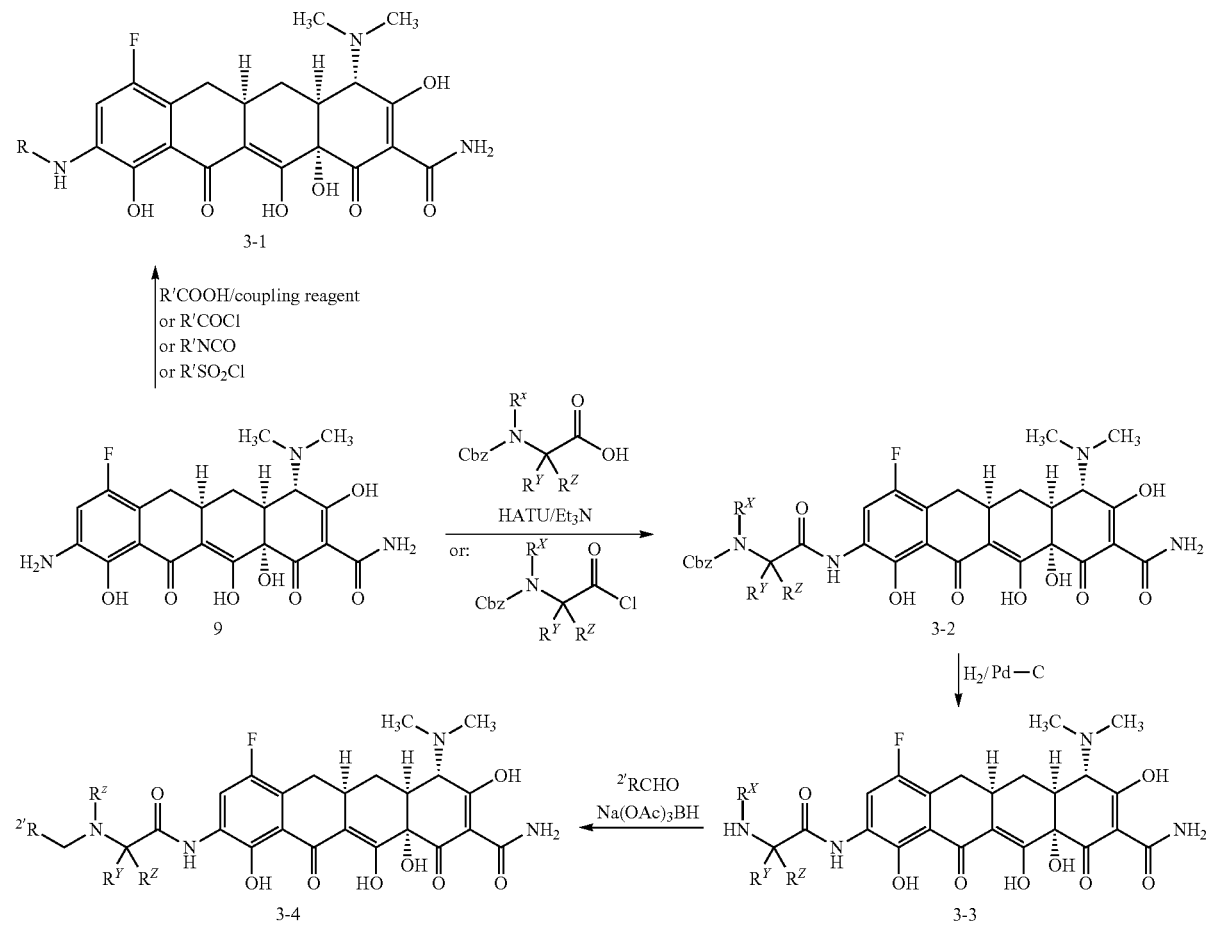

Scheme 3

(R = R'CO, R'NHCO, or R'SO$_2$)

The reaction mixture was filtered through celite to remove the palladium catalyst and concentrated under reduced pressure. Preparative reverse phase HPLC purification of the resulting oil was performed on a Waters Autopurification system using a Polymerx 10µ RP-γ 100 R column [30×21.20 mm, 10 micron, solvent A: 0.05N HCl in water, solvent B: $CH_3CN$; injection volume. 2.5 mL (10% $CH_3CN$ in 0.05N HCl in water); gradient elution with 10→60% B over 15 min, then held at 100% for 5 min; mass-directed fraction collection]. Fractions with the desired MW, eluting at 11.2-12.1 min were collected and freeze-dried. Purification was performed a sec- In Scheme 3, R' represents heterocyclyl, heteroaryl, carbocyclyl, aryl, ($C_1$-$C_6$)alkyl, or —[$C(R^D)(R^E)]_{0-1}$—$N(R^A)$ ($R^B$); and $R^2$ represents hydrogen, ($C_1$-$C_6$)alkyl, —($C_0$-$C_5$) alkylene-carbocyclyl, —($C_0$-$C_5$)alkylene-aryl, —($C_0$-$C_5$) alkylene-heteroaryl, or —($C_0$-$C_5$)alkylene-heterocyclyl. For certain compounds made by Scheme 3 and described below, $R^Z$ is hydrogen and $R^X$ and $R^Y$ are taken together with the carbon and nitrogen atoms to which they are bound to form an optionally substituted 4-7 membered saturated heterocyclyl. It will be readily apparent to those of skill in the art, however, that this Scheme 3 will also be useful to synthesize compounds where $R^X$, $R^Y$ and $R^Z$ are $R^B$, $R^D$ and $R^E$, respectively, as defined in structural formula (A).

The following compounds were prepared according to Scheme 3.

Compound 64

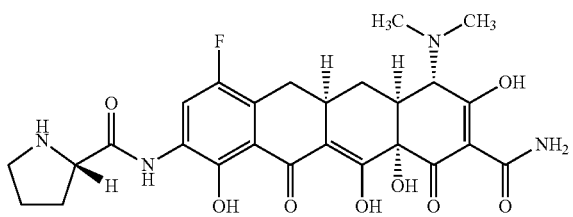

64

To a solution of aniline 9 (17.0 mg, 0.038 mmol, 1 equiv) in DMF (200 μL) was added N-Benzyloxycarbonyl-L-proline acid chloride (1.0 M in toluene, 57 μL, 1.5 equiv). After 50 min the reaction mixture was diluted to 3 mL with 0.05 N HCl in H₂O and filtered to remove any solids. Preparative reverse phase HPLC purification of the resulting solution was performed on a Waters Autopurification system using a Polymerx 10μ, RP-γ 100 R column [30×21.20 mm, 10 micron, solvent A: 0.05N HCl in water, solvent B: CH₃CN; injection volume: 3.5 mL (0.05N HCl in water); gradient elution with 10→20% B over 25 min, then held at 100% for 5 min; mass-directed fraction collection]. Fractions with the desired MW, eluting at 27.1-28.4 min, were collected and freeze-dried.

Palladium on carbon (10%, 10 mg) was added to a solution of the above intermediate in dioxane:MeOH (1:3, 2.3 mL). The flask was fitted with a septum and evacuated and back-filled three times with hydrogen gas. The reaction solution was stirred under an atmosphere (balloon) of hydrogen gas for 1.7 h, then was filtered through celite to remove the palladium catalyst and concentrated under reduced pressure. Half of the resulting residue was purified via preparative reverse phase HPLC purification on a Waters Autopurification system using a Polymerx 10μ, RP-γ 100 R column [30× 21.20 mm, 10 micron, solvent A: 0.05N HCl in water, solvent B: CH₃CN; injection volume: 1.8 mL (0.05 N HCl in water); gradient elution with 0→35% B over 10 min, then held at 100% for 5 min; mass-directed fraction collection]. Fractions with the desired MW, eluting at 7.8-8.5 min, were collected and freeze-dried to yield 1.9 mg of compound 64 (30%): ¹H NMR (400 MHz, CD₃OD) δ 8.16 (d, J=11.0 Hz, 1H), 4.59-4.56 (m, 1H), 4.10 (s, 1H), 3.48-3.33 (m, 2H), 3.18-2.95 (m, 9H), 2.59-2.50 (m, 1H), 2.34-2.05 (m, 5H), 1.70-1.60 (m, 1H); MS (ESI) m/z 545.38 (M+H).

Compound 65

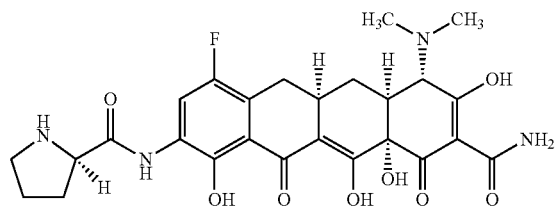

65

To a solution of aniline 9 (15.7 mg, 0.035 mmol, 1 equiv) in DMF (200 μL) was added N-Benzyloxycarbonyl-D-proline acid chloride (1.0 M in toluene, 53 μL, 1.5 equiv). After 50 min, the reaction was complete. The reaction mixture was diluted to 3 mL with 0.05 N HCl in H₂O and filtered to remove any solids. Preparative reverse phase HPLC purification of the resulting solution was performed on a Waters Autopurification system using a Polymerx 10μ, RP-γ 100 R column [30×21.20 mm, 10 micron, solvent A: 0.05 N HCl in water, solvent B: CH₃CN; injection volume: 3.5 mL (0.05 N HCl in water); gradient elution with 15-80% B over 10 min, then held at 100% for 5 min; mass-directed fraction collection]. Fractions with the desired MW, eluting at 6.95-8.10 min, were collected and freeze-dried.

Palladium on carbon (10%, 15 mg) was added to a solution of the above intermediate in dioxane:MeOH (1:3, 2.3 mL). The flask was fitted with a septum and evacuated and back-filled three times with hydrogen gas, and the reaction was stirred under an atmosphere (balloon) of hydrogen gas for 1.5 h. The reaction mixture was filtered through celite to remove the palladium catalyst and concentrated under reduced pressure. Half of the resulting residue was purified via preparative reverse phase HPLC purification on a Waters Autopurification system using a Polymerx 10μ, RP-γ 100 R column [30× 21.20 mm, 10 micron, solvent A: 0.05 N HCl in water, solvent B: CH₃CN; injection volume: 1.8 mL (0.05 N HCl in water); gradient elution with 0→35% B over 10 min, then held at 100% for 5 min; mass-directed fraction collection]. Fractions with the desired MW, eluting at 8.35-8.85 min, were collected and freeze-dried to yield 0.93 mg of compound 65 (24%): ¹H NMR (400 MHz, CD₃OD) δ 8.17 (d, J=11.0 Hz, 1H), 4.59-4.53 (m, 1H), 4.09 (s, 1H), 3.48-3.37 (m, 2H), 3.18-2.90 (m, 9H), 2.59-2.50 (m, 1H), 2.34-2.05 (m, 5H), 1.70-1.59 (m, 1H); MS (ESI) m/z 545.37 (M+H).

Compound 66

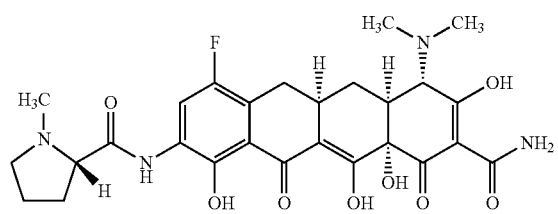

66

The second half of crude 64 (0.012 mmol, 1.0 equiv) was dissolved in DMF (500 μL), and formaldehyde (37% aqueous solution, 5.3 μL, 0.072 mmol, 6 equiv), triethylamine (5.0 μL, 0.036 mmol, 3 equiv), and sodium triacetoxyborohydride (8.4 mg, 0.039 mmol, 3.2 equiv) were added sequentially. After 2 h, the reaction mixture was diluted to 1.8 mL with 0.05N HCl in H₂O and purified via preparative reverse phase HPLC on a Waters Autopurification system using a Polymerx 10μ RP-γ 100 R column [30×21.20 mm, 10 micron, solvent A: 0.05 N HCl in water, solvent B: CH₃CN; injection volume: 1.8 mL (0.05 N HCl in water); gradient: 0-30% B over 10 min; mass-directed fraction collection]. Fractions with the desired MW, eluting at 8.6-9.35 min, were collected and freeze-dried to provide a mixture of the desired compound and an over-formylated product. The resulting compound mixture was dissolved in 4 N aqueous HCl solution (1.5 mL) and stirred for 50 h, then freeze-dried to provide 1.0 mg of the desired compound 66 (15%): ¹H NMR (400 MHz, CD₃OD) δ 8.17 (d, J=10.4 Hz, 1H), 4.36 (t, J=8.6 Hz, 1H), 4.08 (s, 1H), 3.82-3.73 (m, 1H), 3.20-2.90 (m, 12H), 2.73-2.68 (m, 1H), 2.35-2.10 (m, 5H), 1.70-1.60 (m, 1H); MS (ESI) m/z 559.38 (M+H).

Compound 67

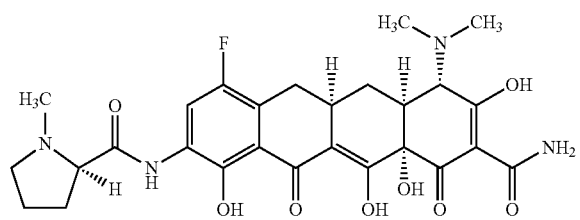

The second half of crude 65 (0.007 mmol, 1.0 equiv) was dissolved in DMF (500 μL), and formaldehyde (37% aqueous solution, 3.1 μL, 0.042 mmol, 6 equiv) and TEA (3.0 μL, 0.021 mmol, 3 equiv), and sodium triacetoxyborohydride (4 mg, 0.026 mmol, 2.6 equiv) were added sequentially. After 2.2 h, the reaction mixture was diluted to 1.8 mL with 0.05N HCl in H$_2$O and purified via preparative reverse phase HPLC on a Waters Autopurification system using a using a Polymerx 10μ RP-γ 100 R column [30×21.20 mm, 10 micron, solvent A: 0.05 N HCl in water, solvent B: CH$_3$CN; injection volume: 2.0 mL (0.05 N HCl in water); gradient: 0→30% B over 10 min; mass-directed fraction collection]. Fractions with the desired MW, eluting at 8.9-9.6 min, were collected and freeze-dried to provide a mixture of the desired compound and an over-formylated product. The resulting compound mixture was dissolved in 6 N aqueous HCl solution and stirred for 50 h, then freeze-dried to provide 1.5 mg of the desired compound 67 (38%): $^1$H NMR (400 MHz, CD$_3$OD) δ 8.17 (d, J=10.4 Hz, 1H), 4.45-4.34 (m, 1H), 4.08 (s, 1H), 3.84-3.74 (m, 1H), 3.20-2.90 (m, 12H), 2.79-2.65 (m, 1H), 2.33-2.05 (m, 5H), 1.70-1.58 (m, 1H); MS (ESI) m/z 559.40 (M+H).

Compound 68

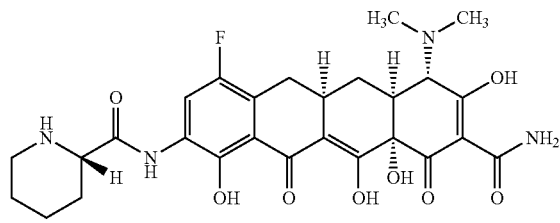

To a solution of (5)-(−)-1-Cbz-piperidinecarboxylic acid (34.2 mg, 0.13 mmol, 3 equiv), and (2-(7-aza-1H-benzotriazole-1-yl)-1,1,3,3-tetramethyluronium hexafluoro-phosphate) (50.0 mg, 0.13 mol, 3 equiv) in DMF (200 μL) was added triethylamine (18 μL, 0.13 mmol, 3 equiv). After 30 min, aniline 9 (17.5 mg, 0.039 mmol, 1 equiv) was added. After 16 h, the reaction mixture was diluted to 3 mL with 0.05 N HCl in H$_2$O and purified via preparative reverse phase HPLC on a Waters Autopurification system using a Polymerx 10μ, RP-γ 100 R column [30×21.20 mm, 10 micron, solvent A: 0.05 N HCl in water, solvent B: CH$_3$CN; injection volume: 3.5 mL (0.05 N HCl in water); gradient elution with 15→70% B over 10 min, then held at 100% for 5 min; mass-directed fraction collection]. Fractions with the desired MW, eluting at 9.07-10.0 min, were collected and freeze-dried. Palladium on carbon (10%, 4 mg) was added to a solution of this foam in dioxane:MeOH (1:3, 1.2 mL). The flask was fitted with a septum and evacuated and back-filled three times with hydrogen gas. The reaction mixture was stirred under an atmosphere (balloon) of hydrogen gas for 1.5 h, then was filtered through celite to remove the palladium catalyst and concentrated under reduced pressure. Preparative reverse phase HPLC purification of the resulting oil was performed on a Waters Autopurification system using a Polymerx 10μ, RP-γ 100 R column [30×21.20 mm, 10 micron, solvent A: 0.05 N HCl in water, solvent B: CH$_3$CN; injection volume: 2.0 mL (0.05 N HCl in water); gradient elution with 0→35% B over 10 min, then held at 100% for 5 min; mass-directed fraction collection]. Fractions with the desired MW, eluting at 8.15-8.58 min, were collected and freeze-dried to yield 0.75 mg of compound 68 (4%): $^1$H NMR (400 MHz, CD$_3$OD) δ 8.15 (d, J=11.0 Hz, 1H), 4.12-4.06 (m, 2H), 3.48-3.40 (m, 2H), 3.20-2.90 (m, 9H), 2.36-2.18 (m, 3H), 2.02-1.90 (m, 2H), 1.82-1.60 (m, 4H); MS (ESI) m/z 559.37 (M+H).

Compound 69

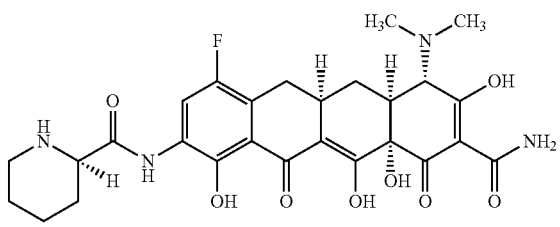

To a solution of (R)-(+)-1-Cbz-piperidinecarboxylic acid (35.0 mg, 0.13 mmol, 3 equiv), and (2-(7-aza-1H-benzotriazole-1-yl)-1,1,3,3-tetramethyluronium hexafluoro-phosphate) (50.0 mg, 0.13 mol, 3 equiv) in DMF (200 μL) was added TEA (18 μL, 0.13 mmol, 3 equiv). After 30 min, aniline 9 (16.6 mg, 0.037 mmol, 1 equiv) was added. After 16 h, the reaction mixture was diluted to 3 mL with 0.05 N HCl in H$_2$O and purified via preparative reverse phase HPLC on a Waters Autopurification system using a Polymerx 10μ RP-γ 100 R column [30×21.20 mm, 10 micron, solvent A: 0.05 N HCl in water, solvent B: CH$_3$CN; injection volume: 3.5 mL (0.05 N HCl in water); gradient elution with 10→50% B over 10 min, then held at 100% for 5 min; mass-directed fraction collection]. Fractions with the desired MW, eluting at 12.1-12.9 min, were collected and freeze-dried. Palladium on carbon (10%, 5 mg) was added to a solution of this foam in dioxane: MeOH (1:3, 800 μL). The flask was fitted with a septum and evacuated and back-filled three times with hydrogen gas. The reaction mixture was stirred under an atmosphere (balloon) of hydrogen gas for 1.75 h, then was filtered through celite to remove the palladium catalyst and concentrated under reduced pressure. Preparative reverse phase HPLC purification of the resulting oil was performed on a Waters Autopurification system using a Polymerx 10μ RP-γ 100 R column [30×21.20 mm, 10 micron, solvent A: 0.05 N HCl in water, solvent B: CH$_3$CN; injection volume: 2.0 mL (0.05 N HCl in water); gradient elution with 0→35% B over 10 min, then held at 100% for 5 min; mass-directed fraction collection]. Fractions with the desired MW, eluting at 8.75-9.16 min, were collected and freeze-dried to yield 0.55 mg of compound 69 (3%): $^1$H NMR (400 MHz, CD$_3$OD) δ 8.16 (d, J=11.0 Hz, 1H), 4.13-4.06 (m, 2H), 3.50-3.43 (m, 2H), 3.20-2.90 (m, 9H), 2.38-2.18 (m, 3H), 2.04-1.88 (m, 2H), 1.83-1.60 (m, 4H); MS (ESI) m/z 559.38 (M+H).

Compound 70

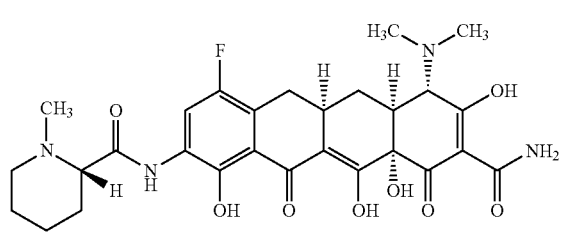

To a solution of compound 68 (0.0138 mmol, 1 equiv) in DMF (750 µL), were added formaldehyde (37% aqueous solution, 6.2 µL, 0.083 mmol, 6 equiv), TEA (5.8 µL, 0.041 mmol, 3 equiv), and sodium triacetoxyborohydride (11 mg, 0.051 mmol, 3.7 equiv) sequentially. After 17 h, the reaction mixture was concentrated to remove amine and 6 N aqueous HCl (500 µL) was added. After 19 days, the reaction solution was purified via preparative reverse phase HPLC on a Waters Autopurification system using a Polymerx 10µ, RP-γ 100 R column [30×21.20 mm, 10 micron, solvent A: 0.05 N HCl in water, solvent B: $CH_3CN$; injection volume: 2.5 mL (0.05 N HCl in water); gradient: 15→50% B over 15 min; mass-directed fraction collection]. Fractions with the desired MW, eluting at 5.75-6.2 min, were collected and freeze-dried to provide 2.4 mg of the desired compound 70 (31%): $^1$H NMR (400 MHz, $CD_3OD$) δ 8.16 (d, J=11.0 Hz, 1H), 4.08-4.04 (m, 1H), 3.59-3.53 (m, 1H), 3.20-3.10 (m, 5H), 3.06-2.96 (m, 5H), 2.90 m (s, 3H), 2.36-2.25 (m, 2H), 2.11-2.05 (m, 1H), 2.02-1.94 (m, 2H), 1.90-1.74 (m, 2H), 1.71-1.58 (m, 2H); MS (ESI) m/z 573.33 (M+H).

Compound 71

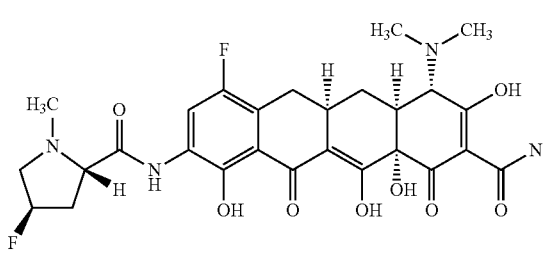

Compound 9 (20 mg, 0.045 mmol, 1.0 equiv) in THF was added $Na_2CO_3$ (9.5 mg, 0.089 mmol, 2.0 equiv), (4R)-4-fluoro-1-methyl-L-proline (9.8 mg, 0.067 mmol, 1.5 equiv) and HATU (34.6 mg, 0.047 mmol, 2.0 equiv). The reaction mixture was stirred at room temperature for 20 hour. LC-MS analysis indicated the starting material was consumed completely. HCl/MeOH (1 mL, 4 N) was added to the mixture at 0° C. and stirred for 2 min. The mixture was concentrated under vacuum, the residue was purified by reverse phase HPLC to afford product 71 (6.1 mg): $^1$H NMR (400 MHz, $CD_3OD$) δ 8.18 (d, J=10.8 Hz, 1H), 5.51 (d, J=51.6 Hz, 1H), 4.76-4.72 (m, 1H), 4.22-4.16 (m, 1H), 4.10 (s, 1H), 3.74-3.63 (m, 1H), 3.21-2.97 (m, 14H), 2.35-2.21 (m, 2H), 1.69-1.60 (m, 1H); MS (ESI) m/z 577.1 (M+H).

Compounds 72 and 73 were prepared similarly to compound 71 using the corresponding amino acids.

Compound 72

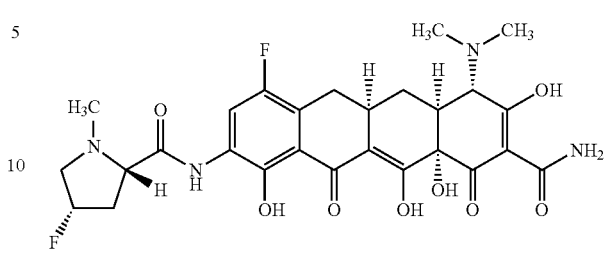

Prepared similarly to compound 71: $^1$H NMR (400 MHz, $CD_3OD$) δ 8.16 (d, J=10.8 Hz, 1H), 5.48 (d, J=51.2 Hz, 1H), 4.60-4.56 (m, 1H), 4.11 (s, 1H), 4.05-3.98 (m, 1H), 3.67-3.54 (m, 1H), 3.24-2.96 (m, 13H), 2.55-2.44 (m, 1H), 2.34-2.22 (m, 2H), 1.70-1.66 (m, 1H); MS (ESI) m/z 577.1 (M+H).

Compound 73

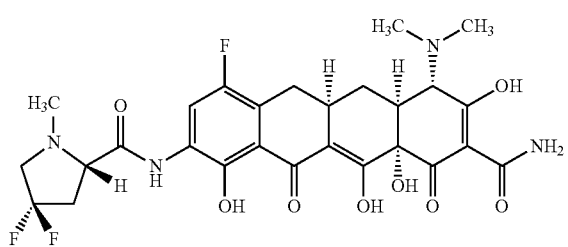

Prepared similarly to compound 71: $^1$H NMR (400 MHz, $CD_3OD$) δ 8.18 (d, J=10.8 Hz, 1H), 4.76-4.71 (m, 1H), 4.17-4.12 (m, 1H), 4.09 (s, 1H), 3.96-3.86 (m, 1H), 3.67-3.53 (m, 1H), 3.55-3.53 (m, 1H), 3.25-2.73 (m, 12H), 2.33-2.19 (m, 2H), 1.68-1.59 (m, 1H); MS (ESI) m/z 595.3 (M+H).

Compound 3-1-1

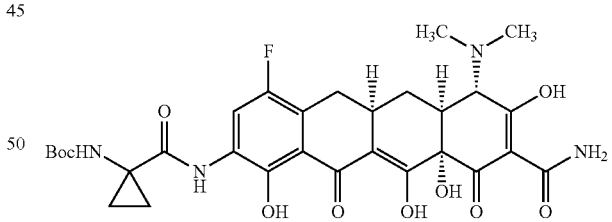

1-(Bocamino)cyclopropanecarboxylic acid (67.4 mg, 0.335 mmol), O-(7-azabenzotriazol-1-yl)-N,N,N',N'-tetramethyluronium hexafluorophosphate (127 mg, 0.335 mmol), and triethylamine (0.078 mL, 0.56 mmol) were stirred in DMF (1 mL) for 30 minutes. Compound 9 (50 mg, 0.112 mmol) was added. After stirring overnight, the reaction mixture was purified directly by preparative reverse phase HPLC purification on a Waters Autopurification system using a Polymerx 10µ RP-γ 100 R column [30×21.20 mm, 10 micron, solvent A: 0.05N HCl, solvent B: $CH_3CN$, gradient elution with 0→50% B over 10 min; mass-directed fraction collection]. Fractions with the desired MW were collected and freeze-dried. The material was repurified by preparative reverse phase HPLC purification on a Waters Autopurification system using a Polymerx 10μ RP-γ 100 R column [30× 21.20 mm, 10 micron, solvent A: 0.05N HCl, solvent B: CH₃CN, gradient elution with 0→100% B over 15 min; mass-directed fraction collection]. Fractions with the desired MW were collected and freeze-dried. This gave 42 mg of compound 3-1-1 (59%, ~80% pure) which was used without further purification. MS (ESI) m/z 631.41 (M+H).

Compound 74

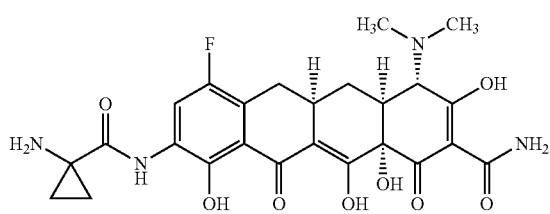

74

Compound 3-1-1 (42 mg, 0.067 mmol, ~80% pure) was stirred in 4M HCl in 1,4-dioxane (5 mL) overnight. The reaction mixture was concentrated under reduced pressure and was purified by preparative reverse phase HPLC purification on a Waters Autopurification system using a Polymerx 10μ, RP-γ 100 R column [30×21.20 mm, 10 micron, solvent A: 0.05N HCl, solvent B: CH₃CN, gradient elution with 0→50% B over 10 min; mass-directed fraction collection]. Fractions with the desired MW were collected and freeze-dried. The material was dissolved in MeOH (1 mL), and the solution was added dropwise to vigorously stirring diethyl ether (200 mL). The resulting solid was collected by filtration on a pad of Celite. This was washed with diethyl ether (3 times), and the solid was dissolved in MeOH and concentrated under reduced pressure. The material was freeze-dried, yielding 25.8 mg of compound 74: ¹H NMR (400 MHz, CD₃OD with 1 drop DCl) δ 8.00 (d, J=7.0 Hz, 1H), 4.05 (s, 1H), 3.20-2.85 (m, 9H), 2.36-2.06 (m, 2H), 1.70-1.52 (m, 3H), 1.35-1.22 (m, 2H); MS (ESI) m/z 531.33 (M+H).

Compound 75

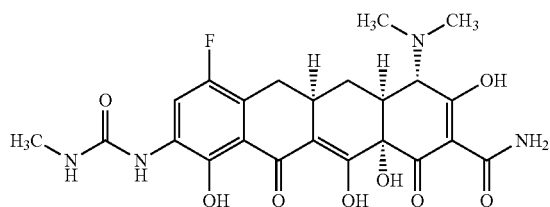

75

To a dichloromethane (5 mL) suspension of compound 9 (0.260 g, 0.50 mmol, 1.0 equiv) at rt was added triethylamine (0.139 mL, 1.00 mmol, 2.0 equiv). The reaction was stirred at rt until form a clear solution. Methylisocyanate (89.4 μL, 1.50 mmol, 3.0 equiv) was added to the reaction mixture dropwise. The reaction was allowed to stir at 25° C. for 1 h. Additional methylisocyanate (45 μL, 0.75 mmol, 1.5 equiv) was added and stirred overnight. LCMS indicate there are still starting material present. The solvent was removed under vacuum to give the crude 75. The crude product was purified by HPLC on a Polymerx 10μ RP-γ 100 R column [30×21.20 mm, 10 micron, solvent A: 0.05 N HCl, solvent B: CH₃CN, sample in 2.0 mL (0.05 N HCl), gradient elution with 15→65% B over 15 min, mass-directed fraction collection] to yield the desired product 75 as a yellow solid (80 mg, 31.7%): ¹H NMR (400 MHz, CD₃OD) δ 8.12 (d, J=11.4 Hz, 1H), 4.07 (s, 1H), 3.04 (s, 3H), 2.96 (s, 3H), 3.13-2.93 (m, 3H), 2.77 (s, 3H), 2.27-2.15 (m, 2H), 1.69-1.57 (m, 1H); MS (ESI) m/z 505.41 (M+H).

Compound 76

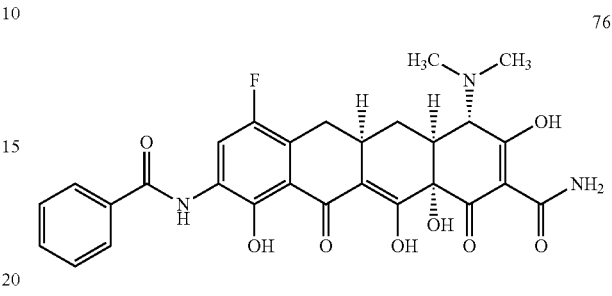

76

Compound 9 (20 mg, 0.045 mmol, 1.0 equiv) in THF was added Na₂CO₃ (9.5 mg, 0.089 mmol, 2.0 equiv) and 0.1 mL benzoyl chloride solution (54 u L in 1 mL THF, 0.047 mmol, 1.05 equiv). The reaction mixture was stirred at room temperature for 1 hour. LC-MS analysis indicated the starting material was consumed completely. HCl/MeOH (1 mL, 4 N) was added to the mixture at 0° C. and stirred for 2 min. The mixture was concentrated under vacuum, the residue was purified by reverse phase HPLC to afford product 76 (5.5 mg): ¹H NMR (400 MHz, CD₃OD) δ 8.23 (d, J=10.8 Hz, 1H), 7.97 (d, J=7.6 Hz, 2H), 7.66-7.54 (m, 3H), 4.11 (s, 1H), 3.21-2.90 (m, 9H), 2.37-2.24 (m, 2H), 1.72-1.66 (m, 1H); MS (ESI) m/z 552.1 (M+H).

Compounds 77-83 were prepared similarly to compound 76 using the corresponding acid chlorides.

Compound 77

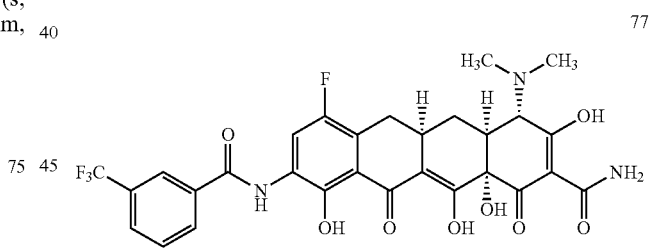

77

¹H NMR (400 MHz, CD₃OD) δ 8.25 (s, 1H), 8.21 (d, J=8.0 Hz, 1H), 8.14 (d, J=10.4 Hz, 1H), 7.92 (d, J=8.0 Hz, 1H), 7.76 (t, J=8.0 Hz, 1H), 4.08 (s, 1H), 3.21-2.89 (m, 9H), 2.35-2.22 (m, 2H), 1.71-1.61 (m, 1H); MS (ESI) m/z 620.1 (M+H).

Compound 78

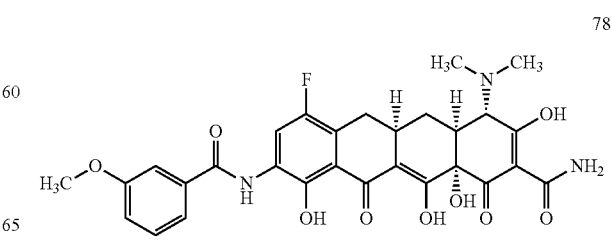

78

¹H NMR (400 MHz, CD₃OD) δ 8.10 (d, J=10.8 Hz, 1H), 7.41-7.33 (m, 3H), 7.09-7.07 (m, 1H), 4.00 (s, 1H), 3.78 (s, 3H), 3.12-2.86 (m, 9H), 2.23-2.13 (m, 2H), 1.60-1.50 (m, 1H); MS (ESI) m/z 582.1 (M+H).

Compound 79

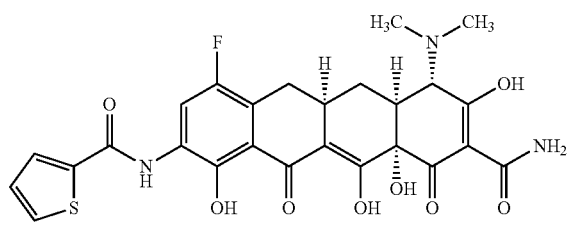

¹H NMR (400 MHz, CD₃OD) δ 8.12 (d, J=10.8 Hz, 1H), 7.89 (d, J=3.2 Hz, 1H), 7.78 (d, J=4.8 Hz, 1H), 7.22 (t, J=8.8 Hz, 1H), 4.10 (s, 1H), 3.20-2.98 (m, 9H), 2.36-2.20 (m, 2H), 1.68-1.61 (m, 1H); MS (ESI) m/z 558.1 (M+H).

Compound 80

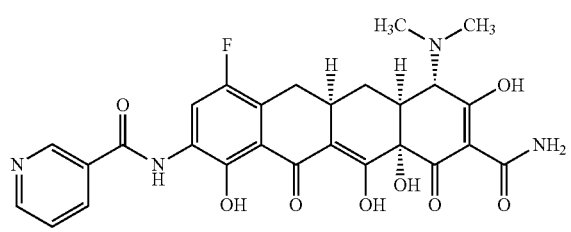

¹H NMR (400 MHz, CD₃OD) δ 9.34 (s, 1H), 9.04-9.00 (m, 2H), 8.20-8.15 (m, 2H), 4.07 (s, 1H), 3.27-2.94 (m, 9H), 2.34-2.18 (m, 2H), 1.68-1.59 (m, 1H); MS (ESI) m/z 553.1 (M+H).

Compound 81

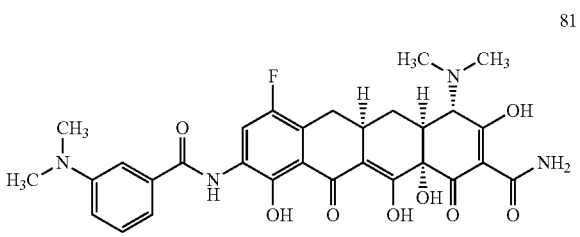

¹H NMR (400 MHz, CD₃OD) δ 8.13-8.06 (m, 2H), 7.98 (d, J=7.6 Hz, 1H), 7.77 (d, J=7.2 Hz, 1H), 7.67 (t, J=8.0 Hz, 1H), 4.01 (s, 1H), 3.26 (s, 6H), 3.14-2.83 (m, 9H), 2.27-2.13 (m, 2H), 1.64-1.52 (m, 1H); MS (ESI) m/z 595.1 (M+H).

Compound 82

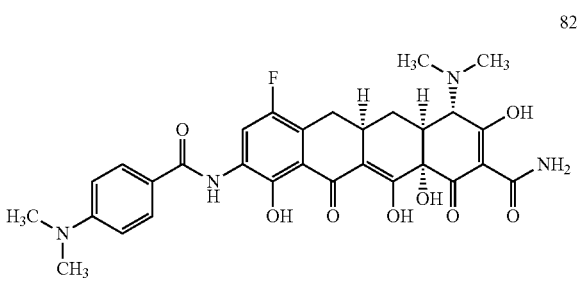

¹H NMR (400 MHz, CD₃OD) δ 8.08 (d, J=10.8 Hz, 1H), 7.98 (d, J=8.4 Hz, 2H), 7.49 (d, J=8.4 Hz, 2H), 4.02 (s, 1H), 3.19 (s, 6H), 3.12-2.88 (m, 9H), 2.24-2.13 (m, 2H), 1.60-1.51 (m, 1H); MS (ESI) m/z 595.1 (M+H).

Compound 83

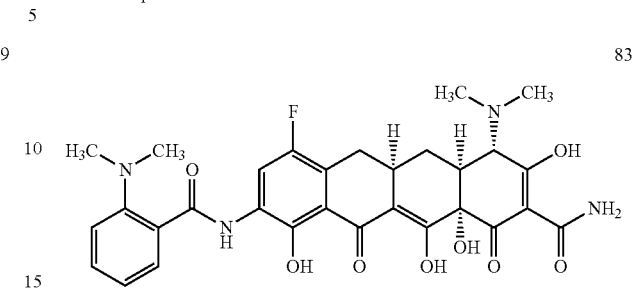

¹H NMR (400 MHz, CD₃OD) δ 8.19-8.14 (m, 2H), 8.05 (d, J=8.4 Hz, 1H), 7.91-7.89 (m, 1H), 7.76-7.74 (m, 1H), 4.12 (s, 1H), 3.32 (s, 6H), 3.21-2.96 (m, 9H), 2.41-1.98 (m, 2H), 1.72-1.59 (m, 1H); MS (ESI) m/z 595.0 (M+H).

Compound 84

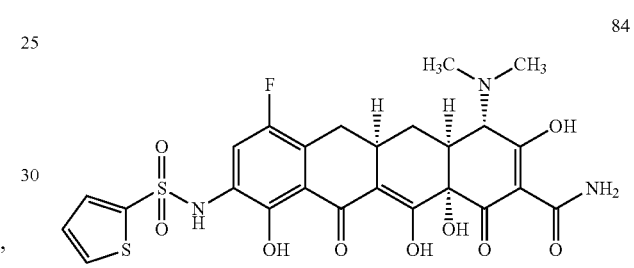

Compound 9 (20 mg, 0.045 mmol, 1.0 equiv) in THF was added DIEA (11.5 mg, 0.089 mmol, 2.0 equiv) and 2-thiophenesulfonyl chloride (12.2 mg, 0.067 mmol, 1.5 equiv). The reaction mixture was stirred at room temperature for 20 hour. LC-MS analysis indicated the starting material was consumed completely. HCl/MeOH (1 mL, 4 N) was added to the mixture at 0° C. and stirred for 2 min. The mixture was concentrated under vacuum, the residue was purified by reverse phase HPLC to afford compound 84 (2.0 mg): ¹H NMR (400 MHz, CD₃OD) δ 7.75 (dd, J=5.2, 1.2 Hz, 1H), 7.59 (d, J=2.8 Hz, 1H), 7.52 (d, J=10.4 Hz, 1H), 7.09 (t, J=4.4 Hz, 1H), 4.07 (s, 1H), 3.11-2.92 (m, 9H), 2.30-2.18 (m, 2H), 1.68-1.58 (m, 1H); MS (ESI) m/z 593.9 (M+H).

Compounds 85-87 were prepared similarly to compound 84 using the corresponding sulfonyl chlorides.

Compound 85

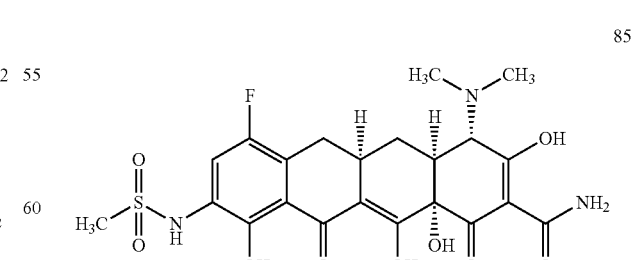

¹H NMR (400 MHz, CD₃OD) δ 7.44 (d, J=10.0 Hz, 1H), 4.10 (s, 1H), 3.21-2.90 (m, 12H), 2.34-2.22 (m, 2H), 1.67-1.61 (m, 1H); MS (ESI) m/z 526.1 (M+H).

Compound 86
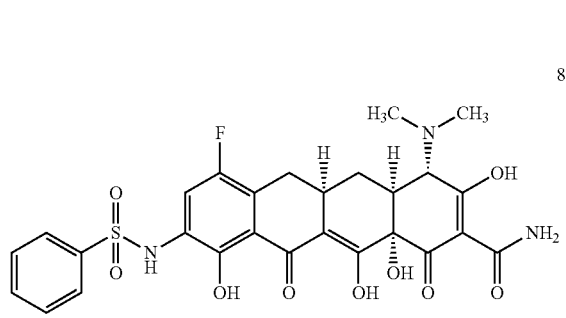
¹H NMR (400 MHz, CD₃OD) δ 7.82 (d, J=7.6 Hz, 2H), 7.58-7.46 (m, 4H), 4.07 (s, 1H), 3.10-2.92 (m, 9H), 2.35-2.25 (m, 2H), 1.65-1.55 (m, 1H); MS (ESI) m/z 552.1 (M+H).
Compound 87
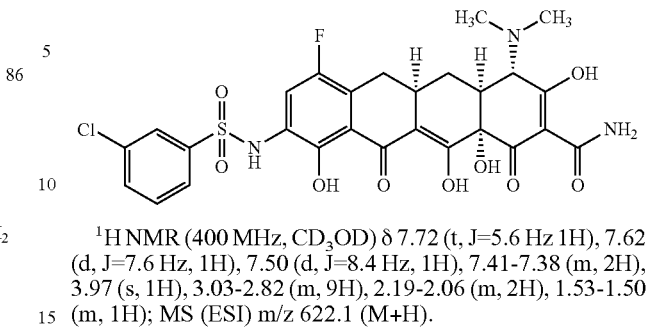
¹H NMR (400 MHz, CD₃OD) δ 7.72 (t, J=5.6 Hz 1H), 7.62 (d, J=7.6 Hz, 1H), 7.50 (d, J=8.4 Hz, 1H), 7.41-7.38 (m, 2H), 3.97 (s, 1H), 3.03-2.82 (m, 9H), 2.19-2.06 (m, 2H), 1.53-1.50 (m, 1H); MS (ESI) m/z 622.1 (M+H).
Example 4
Synthesis of Compounds of Structural Formula (I), Wherein X is hydrogen and Y is
—NH—C(O)-heterocycly or
—NH—C(O)-heteroaryl
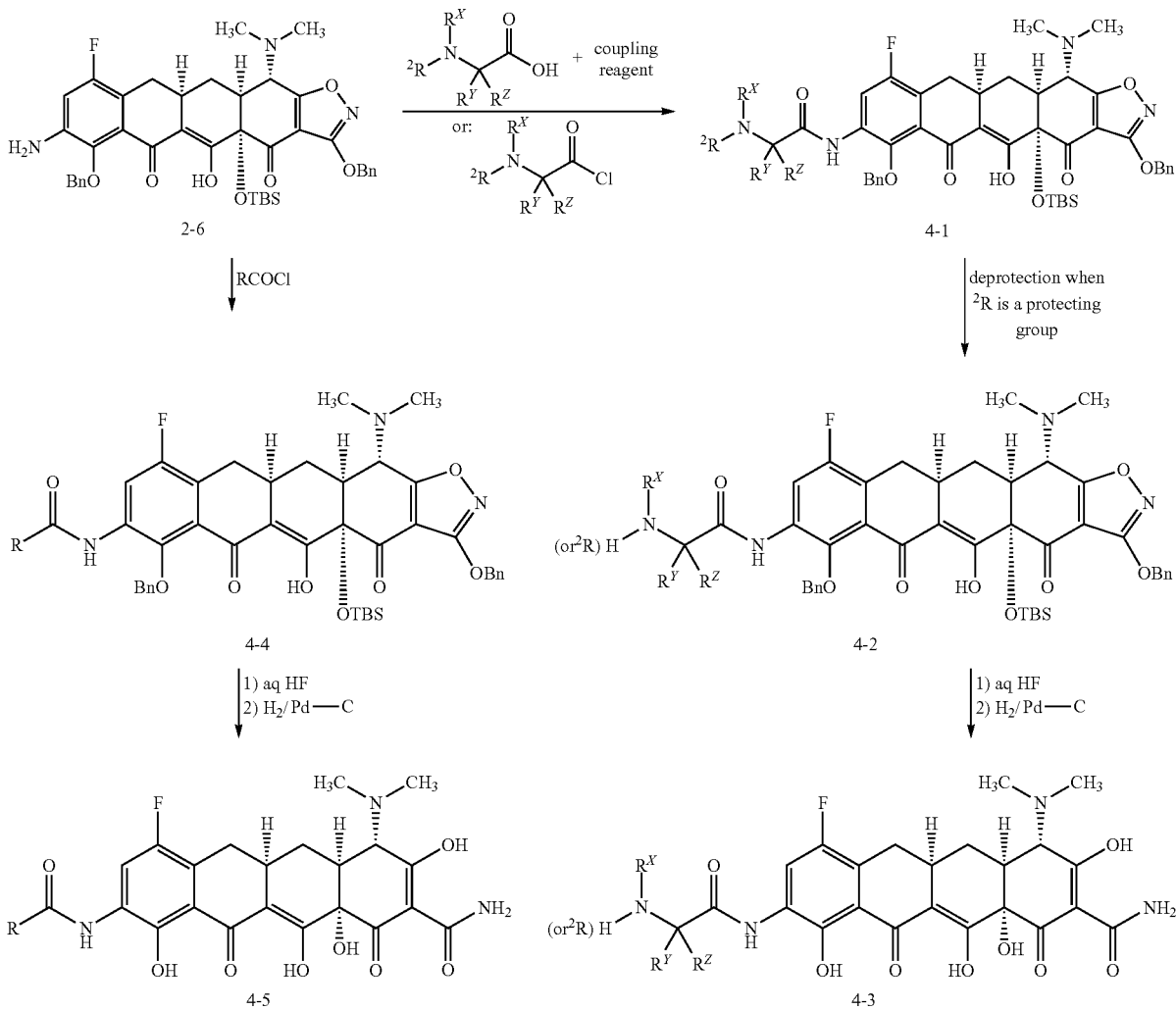

In Scheme 4, R represents heteroaryl and $R^2$ is $R^A$ as defined in Structural Formula (A). For certain compounds made by Scheme 4 and described below, $R^Z$ is hydrogen and $R^X$ and $R^Y$ are taken together with the carbon and nitrogen atoms to which they are respectively bound to form an optionally substituted 4-7 membered saturated heterocyclyl. It will be readily apparent to those of skill in the art, however, that this Scheme 4 will also be useful to synthesize compounds where $R^X$, $R^Y$ and $R^X$ are $R^B$, $R^D$ and $R^E$, respectively, as defined in structural formula (A).

The following compounds were prepared according to Scheme 4.

Compound 88

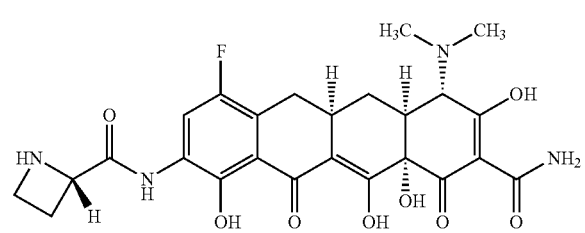

88

To a suspension of 1-Fmoc-L-azetidine-2-carboxylic acid (135 mg, 0.42 mmol, 2.9 equiv), and (2-(7-aza-1H-benzotriazole-1-yl)-1,1,3,3-tetramethyluronium hexafluoro-phosphate) (164 mg, 0.43 mol, 3 equiv) in THF (1.5 mL) was added triethylamine (60 µL, 0.43 mmol, 3 equiv). After 30 min, aniline 2-6 (106 mg, 0.14 mmol, 1 equiv) was added. After 18 h, the reaction mixture was concentrated under reduced pressure. Preparative reverse phase HPLC of the resulting oil was performed on a Waters Autopurification system using a Sunfire Prep C18 OBD column [5 µm, 19×50 mm; flow rate, 20 mL/min; Solvent A: H₂O with 0.1% HCO₂H; Solvent B: CH₃CN with 0.1% HCO₂H; injection volume: 3×2.0 mL (CH₃CN); gradient: 80→100% B over 15 min; mass-directed fraction collection]. Fractions with the desired MW, eluting at 10.35-12.0 min, were collected and freeze-dried to provide 131 mg of a yellow powder.

To a solution of the above intermediate in CH₂Cl₂ (2 mL) was added piperidine (500 µL). After 30 min, the reaction solution was poured into aqueous pH 7 phosphate buffer and extracted with EtOAc (3×20 mL). The combined organic layers were dried (Na₂SO₄), filtered, and concentrated under reduced pressure. Purification of the resulting crude oil via flash column chromatography on silica gel (Silicycle, 5 g, 0 to 5 to 10 to 50% EtOAc in hexane gradient) provided 47.6 mg of the intermediate.

Half of the above intermediate (24 mg) was dissolved in acetonitrile (1 mL), and an aqueous solution of HF (50%, 200 µL) was added. After 18.5 h, the reaction solution was poured into an aqueous K₂HPO₄ solution (2.5 g in 20 mL) and extracted with EtOAc (2×25 mL). The combined organic layers were dried (Na₂SO₄), filtered, and concentrated under reduced pressure.

Palladium on carbon (10%, 12.5 mg) was added to a solution of the above intermediate in dioxane:MeOH (1:1, 1 mL). The flask was fitted with a septum and evacuated and back-filled three times with hydrogen gas. Hydrogen gas was bubbled through the reaction solution for three minutes, and the reaction mixture was stirred under an atmosphere (balloon) of hydrogen gas for 4.5 h. The reaction mixture was filtered through celite to remove the palladium catalyst and concentrated under reduced pressure. Preparative reverse phase HPLC purification of the resulting oil was performed on a Waters Autopurification system using a Polymerx 10µ RP-γ 100 R column [30×21.20 mm, 10 micron, solvent A: 0.05N HCl in water, solvent B: CH₃CN; injection volume: 3.0 mL (0.05N HCl in water); gradient elution with 0→30% B over 10 min, then held at 100% for 5 min; mass-directed fraction collection]. Fractions with the desired MW, eluting at 9.8-11.25 min, were collected and freeze-dried. The resulting impure powder was purified via preparative reverse phase HPLC as above with gradient elution with 15→50% B over 12 min, then held at 100% for 3 min; mass-directed fraction collection. Fractions with the desired MW, eluting at 6.5-8.0 min, were collected and freeze-dried to yield 2.0 mg of compound 88 (5%): ¹H NMR (400 MHz, CD₃OD) δ 8.25 (d, J=11.0 Hz, 1H), 5.29-5.24 (m, 1H), 4.20-4.11 (m, 1H), 4.09 (s, 1H), 3.19-2.89 (m, 10H), 2.69-2.56 (m, 1H), 2.33-2.19 (m, 2H), 1.68-1.56 (m, 1H); MS (ESI) m/z 531.30 (M+H).

N-methyl-L-azetidine-2-carboxylic acid

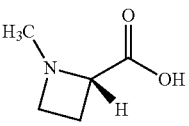

To a suspension of L-azetidine-2-carboxylic acid (290 mg, 2.87 mmol, 1 equiv) in MeOH (3.6 mL), was added aqueous formaldehyde solution (37%, 235 µL, 3.15 mmol, 1.1 equiv) and palladium on carbon (10%, 76 mg). The flask was fitted with a septum and evacuated and back-filled three times with hydrogen gas. The reaction was stirred under an atmosphere (balloon) of hydrogen gas for 19 h, and was filtered through celite to remove the palladium catalyst. The resulting solution was concentrated under reduced pressure, concentrated from toluene three times and dried under vacuum to afford N-methyl-L-azetidine-2-carboxilic acid: ¹H NMR (400 MHz, CD₃OD) δ 4.50 (t, J=9.5 Hz, 1H), 3.96 (dt, J=4.3, 9.8 Hz, 1H), 3.81 (q, J=9.8 Hz, 1H), 2.86 (s, 3H), 2.71-2.60 (m, 1H), 2.50-2.38 (m, 1H).

Compound 4-1-1

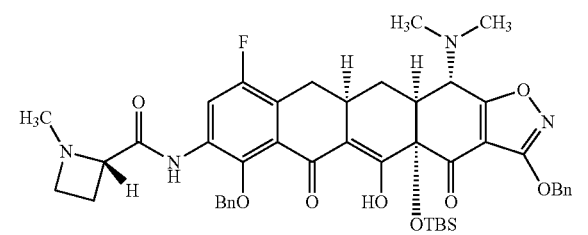

4-1-1

To a suspension of aniline 2-6 (302 mg, 0.408 mmol, 1 equiv) and N-methyl-L-azetidine-2-carboxilic acid (148 mg, 1.28 mmol, 3.1 equiv) in CH₂Cl₂ (6 mL) was added O-(Benzotriazol-1-yl)-N,N,N',N'-tetramethyluronium tetrafluoroborate (395 mg, 1.23 mmol, 3 equiv) and DIEA (285 µL, 1.64 mmol, 4 equiv). After 16.5 h, the resulting orange solution was concentrated under reduced pressure and purified via preparative reverse phase HPLC on a Waters Autopurification system using a Sunfire Prep C18 OBD column [5 µm, 19×50 mm; flow rate, 20 mL/min; Solvent A: H$_2$O with 0.1% HCO$_2$H; Solvent B: CH$_3$CN with 0.1% HCO$_2$H; injection volume: 4×2.5-3.0 mL (CH$_3$CN); gradient: 50→90% B over 15 min; mass-directed fraction collection]. Two sets of fractions with the desired MW, eluting at 4.6-6.5 min and 6.5-9.4 min, were collected separately and freeze-dried to provide 147 mg of 4-1-1 (43%): $^1$H NMR (400 MHz, CDCl$_3$) δ 16.04 (s, 1H), 10.10 (s, 1H), 8.48 (d, J=11.0 Hz, 1H), 7.54-7.48 (m, 4H), 7.40-7.32 (m, 5H), 5.36 (s, 2H), 4.99 (d, J=9.8 Hz, 1H), 4.90 (d, J=9.8 Hz, 1H), 3.96 (d, J=10.4 Hz, 1H), 3.54 (t, J=7.9 Hz, 1H), 3.39-3.34 (m, 1H), 3.25-3.19 (m, 1H), 3.05-2.92 (m, 2H), 2.58-2.36 (m, 10H), 2.23-2.06 (m, 4H), 0.81 (s, 9H), 0.28 (s, 3H), 0.11 (s, 3H); MS (ESI) m/z 837.37 (M+H).

Compound 89

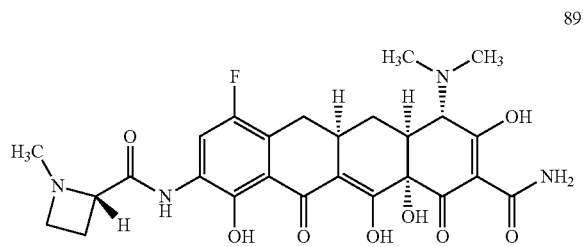

89

To a solution of 4-1-1 (147 mg, 0.175 mmol, 1 equiv) in dioxane (3.5 mL) was added an aqueous solution of HF (50%, 750 µL). After 4 h, the reaction solution was poured into an aqueous K$_2$HPO$_4$ solution (9 g in 90 mL) and extracted with EtOAc (2×50 mL). The combined organic layers were dried (Na$_2$SO$_4$), filtered, and concentrated under reduced pressure to provide 128.4 mg of a crude yellow foam.

The HF deprotection product (144 mg, 0.199 mmol, 1 equiv) was dissolved in dioxane:MeOH (1:1, 4 mL), and palladium on carbon (10%, 43.5 mg) was added. The flask was fitted with a septum and evacuated and back-filled three times with hydrogen gas. Hydrogen gas was bubbled through the reaction solution for three minutes, and the reaction mixture was stirred under an atmosphere (balloon) of hydrogen gas for 3.25 h. The reaction mixture was filtered through celite to remove the palladium catalyst and concentrated under reduced pressure. Preparative reverse phase HPLC of this oil was performed on a Waters Autopurification system using a Polymerx 10µ RP-γ 100 R column [30×21.20 mm, 10 micron, solvent A: 0.05 N HCl in water, solvent B: CH$_3$CN; injection volume: 2×3.2 mL (0.05 N HCl in water); gradient: 10→35% B over 20 min; mass-directed fraction collection]. Fractions with the desired MW, eluting at 6.10-8.40 min and 6.9-9.4 min, respectively for each run, were combined. The pH of the solution at 0° C. was adjusted (pH 1.8 to pH 7.4) via dropwise addition of 0.5 M aqueous NaOH solution (approximately 7.8 mL) and careful monitoring with an electronic pH meter. The aqueous solution was extracted with CH$_2$Cl$_2$ (3×60 mL) and the combined organic layers were dried (Na$_2$SO$_4$), filtered, and concentrated under reduced pressure to provide 79.7 mg of compound 89 as the free base (0.146 mmol, 73%). This yellow solid was dissolved in MeOH (3 mL), and MeSO$_3$H (19 µL, 0.292 mmol, 2 equiv) was added. The solution was concentrated under reduced pressure, dried under vacuum, and freeze-dried from water to provide 105 mg of 89 as the dimesylate salt. $^1$H NMR (400 MHz, CD$_3$OD) δ 8.22 (d, J=11.0 Hz, 1H), 5.16 (t, J=8.6 Hz, 1H), 4.21-4.12 (m, 1H), 4.09-4.02 (m, 2H), 3.17-2.85 (m, 10H), 2.68 (s, 6H, mesylate H), 2.64-2.59 (m, 1H), 2.34-2.15 (m, 2H), 1.70-1.58 (m, 1H); MS (ESI) m/z 545.18 (M+H).

General Procedures for the Preparation of Compounds 90-94

To a solution of aniline 2-6 (1 equiv) in THF (0.05-0.09M) was added an acid chloride (3 equiv). The reaction solution was filtered through celite and concentrated under reduced pressure. The resulting oil was dissolved in dioxane (1 mL) and an aqueous solution of HF (50%, 200 µL) was added. Upon completion, the reaction was poured into an aqueous K$_2$HPO$_4$ solution (2.6 g in 30 mL) and extracted with EtOAc (2×25 mL). The combined organic layers were dried (Na$_2$SO$_4$), filtered, and concentrated under reduced pressure. Palladium on carbon (10%) was added to a solution of this crude oil in dioxane:MeOH (1:1, 1 mL). The flask was fitted with a septum and evacuated and back-filled three times with hydrogen gas, and then the solution was degassed with bubbling hydrogen for 2 minutes. The reaction was stirred under an atmosphere (balloon) of hydrogen gas for 2 h. The reaction mixture was filtered through celite to remove the palladium catalyst and concentrated under reduced pressure. The crude products were purified by preparative reverse phase HPLC.

Compound 90

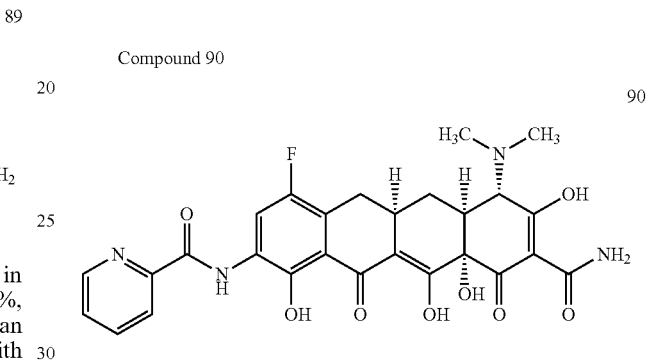

90

Prepared by above general procedure with the following reagents: aniline 2-6 (21.1 mg, 0.028 mmol, 1 equiv), picolinoyl chloride hydrochloride (15.8 mg, 0.088, 3 equiv), with triethylamine (11.7 µL, 0.084 mmol, 3 equiv), and 10% Pd—C (10 mg), provided a crude oil. Preparative reverse phase HPLC of the crude product was performed on a Waters Autopurification system using a Polymerx 10µ RP-γ 100 R column [30×21.20 mm, 10 micron, solvent A: 0.05 N HCl in water, solvent B: CH$_3$CN; injection volume: 2.5 mL (0.05 N HCl in water); gradient: 10-460% B over 20 min; mass-directed fraction collection]. Fractions with the desired MW, eluting at 14.8-16.4 min, were collected and freeze-dried to provide 5.8 mg of the desired compound 90 (37%): $^1$H NMR (400 MHz, CD$_3$OD) δ 8.73-8.69 (m, 1H), 8.58-8.52 (m, 1H), 8.27-8.21 (m, 1H), 8.08-8.00 (m, 1H), 7.66-7.60 (m, 1H), 4.09 (s, 1H), 3.29-2.92 (m, 9H), 2.38-2.18 (m, 2H), 1.72-1.60 (m, 1H); MS (ESI) m/z 553.27 (M+H).

Compound 91

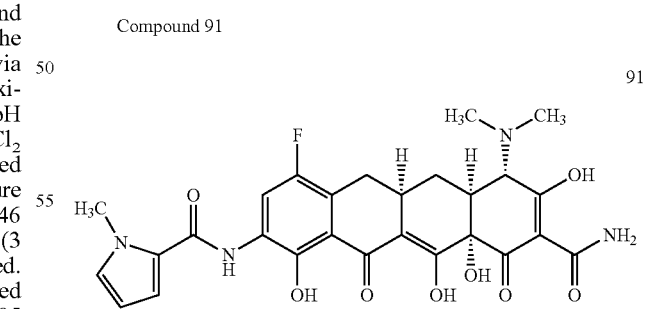

91

Prepared by above general procedure with the following reagents: aniline 2-6 (31.0 mg, 0.042 mmol, 1 equiv), 1-methylpyrrole-2-carbonyl chloride (22 mg, 0.15 mmol, 3 equiv), and 10% Pd—C (10 mg). Preparative reverse phase HPLC of the crude product was performed on a Waters Autopurification system using a Polymerx 10 RP-γ 100 R column [30×21.20 mm, 10 micron, solvent A: 0.05 N HCl in water, solvent B: CH$_3$CN; injection volume: 2.0 mL (0.05 N HCl in water);

gradient: 20→70% B over 20 min; mass-directed fraction collection]. Fractions with the desired MW were collected and freeze-dried and repurified via the same system with the gradient: 10→60% B over 20 min. Fractions with the desired MW, eluting at 15.5-16.5 min, were collected and freeze-dried to provide 2.5 mg of the desired compound 91 (11%): $^1$H NMR (400 MHz, CD$_3$OD) δ 8.20 (d, J=11.6 Hz, 1H), 6.98-6.86 (m, 2H), 6.17-6.10 (m, 1H), 4.08 (s, 1H), 3.94 (s, 3H), 3.19-2.90 (m, 9H), 2.33-2.18 (m, 2H), 1.80-1.56 (m, 1H); MS (ESI) m/z 555.32 (M+H).

Compound 92

92

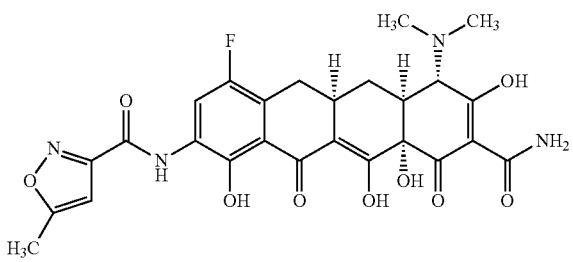

Prepared by above general procedure with the following reagents: aniline 2-6 (31.0 mg, 0.042 mmol, 1 equiv), 5-methylisoxazole-3-carbonyl chloride (19.0 mg, 0.13 mmol, 3 equiv), and 10% Pd—C (10 mg). Preparative reverse phase HPLC of the crude product was performed on a Waters Autopurification system using a Polymerx 10μ RP-γ 100 R column [30×21.20 mm, 10 micron, solvent A: 0.05 N HCl in water, solvent B: CH$_3$CN; injection volume: 2.8 mL (0.05 N HCl in water); gradient: 10→60% B over 20 min; mass-directed fraction collection]. Fractions with the desired MW, eluting at 14.5-15.5 min, were collected and freeze-dried to provide 4.0 mg of the desired compound 92 (17%): $^1$H NMR (400 MHz, CD$_3$OD) δ 8.32 (d, J=11.0 Hz, 1H), 6.59 (s, 1H), 4.09 (s, 1H), 3.19-2.90 (m, 9H), 2.52 (s, 3H), 2.34-2.18 (m, 2H), 1.71-1.58 (m, 1H); MS (ESI) m/z 557.26 (M+H).

Compound 93

93

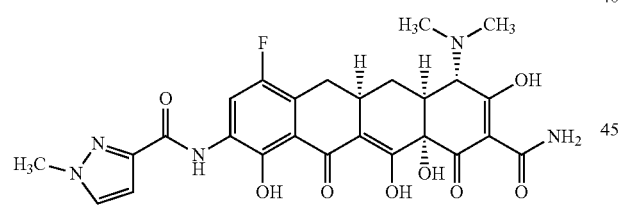

Prepared by above general procedure with the following reagents: aniline 2-6 (30.0 mg, 0.041 mmol, 1 equiv), 1-methyl-1H-pyrazole-3-carbonyl chloride (16.8 mg, 0.12 mmol, 3 equiv), and 10% Pd—C (20 mg). Preparative reverse phase HPLC of the crude product was performed on a Waters Autopurification system using a Polymerx 10μ RP-γ 100 R column [30×21.20 mm, 10 micron, solvent A: 0.05 N HCl in water, solvent B: CH$_3$CN; injection volume: 3.2 mL (0.05 N HCl in water); gradient: 10→60% B over 20 min; mass-directed fraction collection]. Fractions with the desired MW, eluting at 12.5-14.5 min, were collected and freeze-dried to provide 11.2 mg of the desired compound 93 (49%): $^1$H NMR (400 MHz, CD$_3$OD) δ 8.38 (d, J=11.0 Hz, 1H), 7.68 (s, 1H), 6.82-6.76 (m, 1H), 4.09 (s, 1H), 3.99 (s, 3H), 3.16-2.90 (m, 9H), 2.31-2.16 (m, 2H), 1.70-1.56 (m, 1H); MS (ESI) m/z 556.31 (M+H).\

Compound 94

94

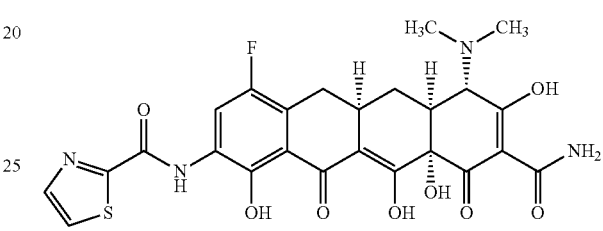

Prepared by above general procedure with the following reagents: aniline 2-6 (30.0 mg, 0.041 mmol, 1 equiv), 1,3-thiazole-2-carbonyl chloride (17.8 mg, 0.12 mmol, 3 equiv), and 10% Pd—C (15 mg). Preparative reverse phase HPLC of the crude product was performed on a Waters Autopurification system using a Polymerx 10μ RP-γ 100 R column [30×21.20 mm, 10 micron, solvent A: 0.05 N HCl in water, solvent B: CH$_3$CN; injection volume: 3.2 mL (0.05 N HCl in water); gradient: 10→60% B over 20 min; mass-directed fraction collection]. Fractions with the desired MW, eluting at 14.6-17.0 min, were collected and freeze-dried to provide 5.4 mg of the desired compound 94 (23%): $^1$H NMR (400 MHz, CD$_3$OD) δ 8.38 (d, J=11.0 Hz, 1H), 8.02 (d, J=3.0 Hz, 1H), 7.95 (d, J=2.4 Hz, 1H), 4.09 (s, 1H), 3.20-2.90 (m, 9H), 2.34-2.17 (m, 2H), 1.70-1.56 (m, 1H); MS (ESI) m/z 559.23 (M+H).

Example 5

Synthesis of Compounds of Structural Formula (A), Wherein Y is —N(R$^A$)(R$^B$), or —NH—SO$_2$—(CH$_2$)$_2$—N(R$^A$)(R$^B$)

Scheme 5

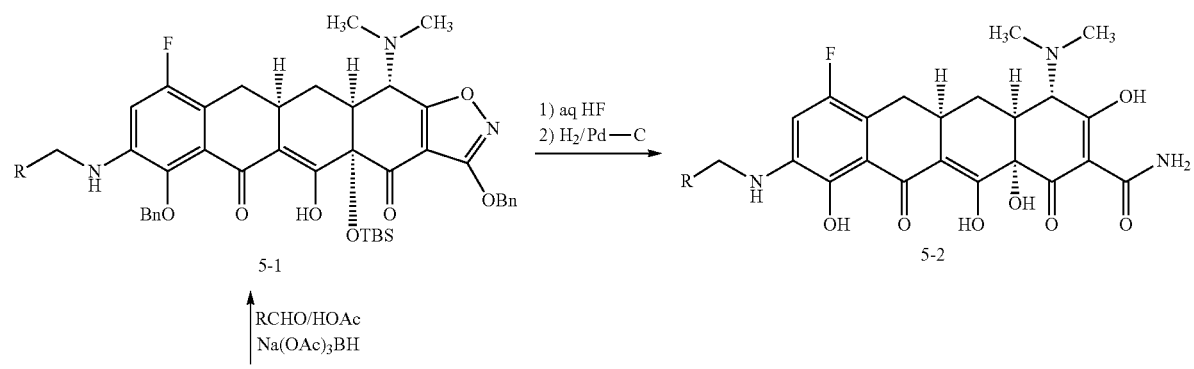

-continued

In Scheme 5, R represents —(C$_1$-C$_6$)alkyl, —(C$_0$-C$_5$)alkylene-carbocyclyl, —(C$_0$-C$_5$)alkylene-aryl, —(C$_0$-C$_5$)alkylene-heterocyclyl, —(C$_0$-C$_5$)alkylene-heteroaryl, —(C$_1$-C$_3$)alkylene-N(R$^A$)(R$^B$); Ar represents an aryl or a heteroaryl group; and R$^U$ and R$^V$ are R$^A$ and R$^B$, receptively, as defined in Structural Formula (B).

The following compounds were prepared according to Scheme 5.

Compound 5-1-1

Compound 2-6 (150 mg, 0.203 mmol, 1.0 equiv) was dissolved in 1,2-dichloroethane (3 mL). HOAc (58.1 μL, 1.01 mmol, 5 equiv.) and isovaleraldehyde (32.9 μL, 0.304 mmol, 1.5 equiv) were added. The mixture was stirred for 1 h. Na(OAc)$_3$BH (129 mg, 0.609 mmol, 3.0 equiv) was added and the resulting mixture was stirred for another hour. The mixture was washed with H$_2$O (10 mL) and concentrated to give crude 5-1-1 (250 mg), which was used for the next step without further purification: MS (ESI) m/z 810.59 (M+H).

Compound 95

Aqueous HF (0.3 mL, 48-50%) was added to a CH$_3$CN solution (1.5 mL) of 5-1-1 (250 mg crude) in a plastic vial at 25° C. The reaction was stirred at 25° C. for 18 hrs. The resulting mixture was poured into an aqueous solution (10 mL) of K$_2$HPO$_4$ (2 g). The solution was extracted with EtOAc (3×15 mL). The combined EtOAc extracts were dried over sodium sulfate and concentrated to give the crude intermediate (155 mg).

10% Pd—C (20 mg) was added to a dioxane/MeOH solution (4 mL, 1:1) of the above crude intermediate. HCl/MeOH (0.5 mL, 0.5 N) was also added. The reaction mixture was stirred under H₂ (balloon) at 25° C. for 2 hrs and filtered through a pad of Celite. The filtrate was concentrated to give the crude product 144 mg. The crude product was purified by HPLC on a Polymerx 10μ RP-γ 100 R column [30×21.20 mm, 10 micron, solvent A: 0.05 N HCl, solvent B: CH₃CN, sample in 2.0 mL (0.05 N HCl), gradient elution with 10→100% B over 15 min, mass-directed fraction collection] to yield the desired product 95 as a yellow solid (82 mg, 78%, 2 steps): ¹H NMR (400 MHz, CD₃OD) δ 7.44 (d, J=9.2 Hz, 1H), 4.12 (s, 1H), 3.42-3.37 (m, 2H), 3.05 (s, 3H), 2.97 (s, 3H), 3.21-2.97 (m, 3H), 2.39-2.30 (m, 1H), 2.29-2.22 (m, 1H), 1.79-1.59 (m, 4H), 0.98 (d, J=6.4 Hz, 6H); MS (ESI) m/z 518.43 (M+H).

Compounds 96-101 were prepared similarly to compound 95 using the corresponding aldehydes in the reductive alkylation step.

Compound 96

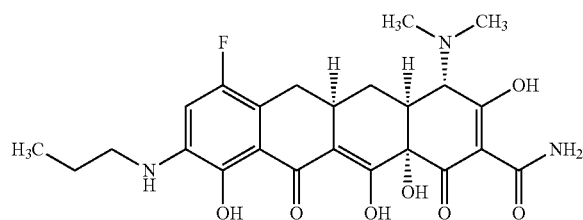

¹H NMR (400 MHz, CD₃OD) δ 7.39 (d, J=9.2 Hz, 1H), 4.10 (s, 1H), 3.34 (t, J=7.8 Hz, 2H), 3.04 (s, 3H), 2.96 (s, 3H), 3.21-2.95 (m, 3H), 2.35 (t, J=13.7 Hz, 1H), 2.27-2.20 (m, 1H), 1.82-1.72 (m, 2H), 1.71-1.60 (m, 1H), 1.05 (t, J=7.4 Hz, 3H); MS (ESI) m/z 490.32 (M+H).

Compound 97

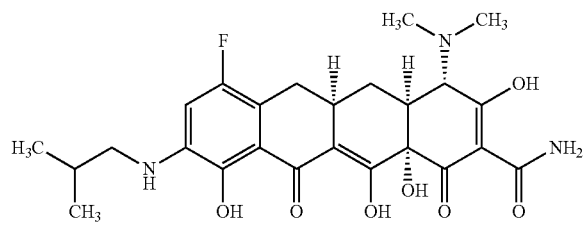

¹H NMR (400 MHz, CD₃OD) δ 7.34 (d, J=9.2 Hz, 1H), 4.10 (s, 1H), 3.34 (t, J=7.8 Hz, 2H), 3.04 (s, 3H), 2.96 (s, 3H), 3.24-2.95 (m, 11H), 2.33 (t, J=13.7 Hz, 1H), 2.27-2.20 (m, 1H), 2.11-1.98 (m, 1H), 1.71-1.60 (m, 1H), 1.08 (d, J=6.9 Hz, 6H); MS (ESI) m/z 504.46 (M+H).

Compound 98

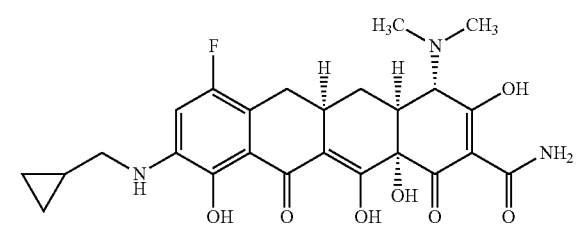

¹H NMR (400 MHz, CD₃OD) δ 7.43 (d, J=8.7 Hz, 1H), 4.10 (s, 1H), 3.34 (t, J=7.8 Hz, 2H), 3.04 (s, 3H), 2.96 (s, 3H), 3.28-2.95 (m, 11H), 2.41-2.31 (m, 1H), 2.27-2.20 (m, 1H), 2.11-1.98 (m, 1H), 1.72-1.60 (m, 1H), 1.20-1.11 (m, 1H), 0.74-0.68 (m, 2H), 0.43-0.38 (m, 2H); MS (ESI) m/z 502.40 (M+H).

Compound 99

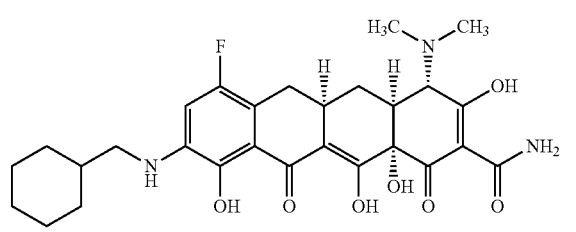

¹H NMR (400 MHz, CD₃OD) δ 6.97-6.89 (m, 1H), 4.07 (s, 1H), 3.34 (t, J=7.8 Hz, 2H), 3.03 (s, 3H), 2.95 (s, 3H), 3.14-2.92 (m, 11H), 2.30-2.15 (m, 2H), 1.89-1.59 (m, 7H), 1.38-1.20 (m, 3H), 1.11-1.00 (m, 2H); MS (ESI) m/z 544.50 (M+H).

Compound 100

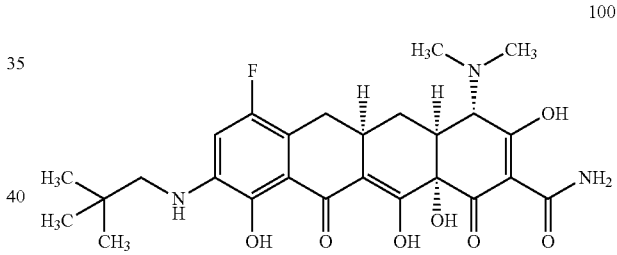

¹H NMR (400 MHz, CD₃OD) δ 6.83 (d, J=10.5 Hz, 1H), 4.06 (s, 1H), 3.34 (t, J=7.8 Hz, 2H), 3.03 (s, 3H), 2.95 (s, 3H), 3.11-2.93 (m, 5H), 2.27-2.14 (m, 2H), 1.67-1.57 (m, 1H), 1.04 (s, 9H); MS (ESI) m/z 518.48 (M+H).

Compound 101

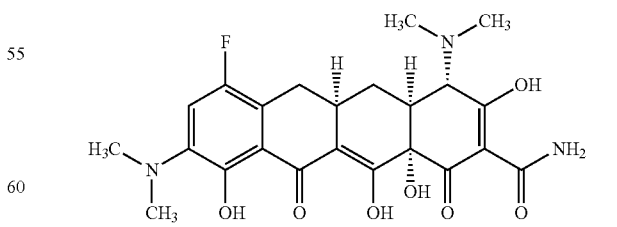

¹H NMR (400 MHz, CD₃OD) δ 7.46-7.42 (m, 1H), 4.15 (s, 1H), 3.33 (s, 6H), 3.04 (s, 3H), 2.96 (s, 3H), 3.17-2.95 (m, 3H), 2.44-2.34 (m, 1H), 2.29-2.22 (m, 1H), 1.71-1.60 (m, 1H); MS (ESI) m/z 476.29 (M+H).

Compound 102

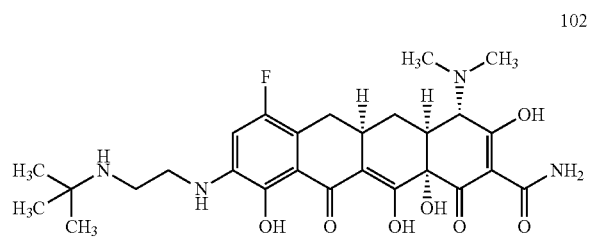

Prepared similarly to 95 using tBuN(Cbz)CH₂CHO: ¹H NMR (400 MHz, CD₃OD) δ 6.72 (d, J=11.0 Hz, 1H), 4.07 (s, 1H), 3.54-3.46 (m, 2H), 3.26-3.19 (m, 2H), 3.03 (s, 3H), 2.95 (s, 3H), 3.14-2.92 (m, 3H), 2.23-2.14 (m, 2H), 1.67-1.55 (m, 1H), 1.38 (s, 9H); MS (ESI) m/z 547.51 (M+H).

Compound 103

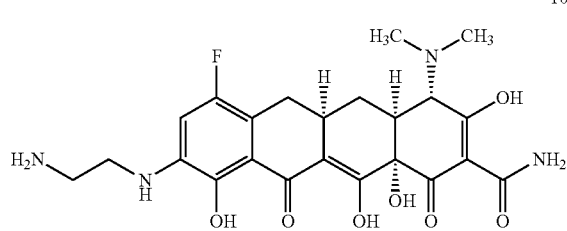

Compound 103 was also isolated from the preparation of 102: ¹H NMR (400 MHz, CD₃OD) δ 6.71 (d, J=11.0 Hz, 1H), 4.07 (s, 1H), 3.47 (t, J=6.0 Hz, 2H), 3.17 (t, J=6.0 Hz, 2H), 3.03 (s, 3H), 2.95 (s, 3H), 3.13-2.92 (m, 3H), 2.23-2.12 (m, 2H), 1.66-1.54 (m, 1H); MS (ESI) m/z 491.42 (M+H).

Compound 5-3-1

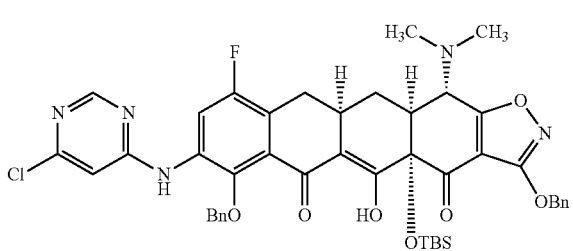

A vessel containing aniline 2-6 (18.2 mg, 0.024 mmol, 1 equiv), Pd₂dba₃ (3.0 mg, 0.0033 mmol, 0.13 equiv), Xantphos (3.4 mg, 0.0059 mmol, 0.25 equiv), K₃PO₄ (40 mg, 0.188 mmol, 7.8 equiv) and 4,6-dichloropyrimidine (6.5 mg, 0.044 mmol, 1.8 equiv) was evacuated and back-filled with nitrogen gas three times. Dioxane (500 µL) was added, and the reaction mixture stirred vigorously and heated at 80° C. for 4.5 h. The reaction mixture was filtered through celite and concentrated under reduced pressure. Preparative reverse phase HPLC of the resulting yellow oil was performed on a Waters Autopurification system using a Sunfire Prep C18 OBD column [5 µm, 19×50 mm; flow rate, 20 mL/min; Solvent A: H₂O with 0.1% HCO₂H; Solvent B: CH₃CN with 0.1% HCO₂H; injection volume: 1.8 mL (CH₃CN); gradient: 80→100% B over 15 min; mass-directed fraction collection]. Fractions with the desired MW, eluting at 9.2-9.8 min, were collected and freeze-dried to provide 7.5 mg of compound 5-3-1 (37%). ¹H NMR (400 MHz, CDCl₃) δ 15.97 (s, 1H), 8.48 (s, 1H), 8.33 (d, J=5.5 Hz, 1H), 7.52-7.46 (m, 2H), 7.40-7.28 (m, 8H), 7.07 (s, 1H), 6.11 (s, 1H), 5.34 (s, 2H), 4.97 (d, J=11.6 Hz, 1H), 4.88 (d, J=11.0 Hz, 1H), 3.95 (d, J=10.4 Hz, 1H), 3.28-3.19 (m, 1H), 3.09-2.98 (m, 1H), 2.61-2.54 (m, 1H), 2.54-2.39 (m, 8H), 2.16 (d, J=14.6 Hz, 1H), 0.83 (s, 9H), 0.28 (s, 3H), 0.14 (s, 3H); MS (ESI) m/z 852.57 (M+H).

Compound 104

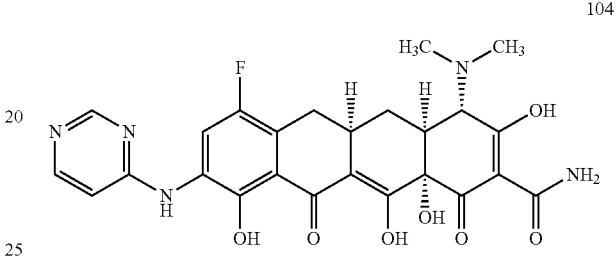

To a solution of 5-3-1 (7.5 mg, 0.0088 mmol, 1 equiv) in dioxane (1.4 mL) was added an aqueous solution of HF (50%, 200 µL). After 15.5 h, the reaction solution was poured into an aqueous K₂HPO₄ solution (2.4 g in 20 mL) and extracted with EtOAc (2×20 mL). The combined organic layers were dried (Na₂SO₄), filtered, and concentrated under reduced pressure. Palladium on carbon (10%, 10 mg) was added to a solution of this oil in dioxane:MeOH (1:1, 1 mL). The flask was fitted with a septum and evacuated and back-filled three times with hydrogen gas. Hydrogen gas was bubbled through the reaction solution for three minutes, and the reaction mixture was stirred under an atmosphere (balloon) of hydrogen gas for 2.5 h. The reaction mixture was filtered through celite to remove the palladium catalyst and concentrated under reduced pressure. Preparative reverse phase HPLC purification of the resulting oil was performed on a Waters Autopurification system using a Polymerx 10µ RP-γ 100 R column [30×21.20 mm, 10 micron, solvent A: 0.05 N HCl in water, solvent B: CH₃CN; injection volume: 2.0 mL (0.05 N HCl in water); gradient elution with 10→50% B over 10 min, then held at 100% for 5 min; mass-directed fraction collection]. Fractions with the desired MW, eluting at 6.90-7.80 min, were collected and freeze-dried to provide 2.2 mg of 104 (48%). ¹H NMR (400 MHz, CD₃OD) δ 8.83 (s, 1H), 8.37-8.25 (m, 1H), 8.18-8.05 (m, 1H), 7.30-7.20 (m, 1H), 4.10 (s, 1H), 3.20-2.90 (m, 9H), 2.40-2.29 (m, 1H), 2.27-2.19 (m, 1 µl), 1.72-1.58 (m, 1H); MS (ESI) m/z 526.31 (M+H).

Compound 105

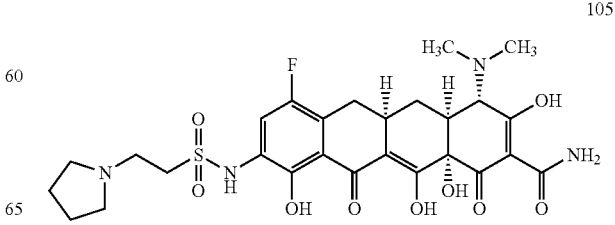

To a solution of aniline 2-6 (30.0 mg, 0.041 mmol, 1 equiv) in 1,2-dichloroethane (500 μL) was added pyridine (16.3 μL, 0.20 mmol, 5 equiv) and 2-chloroethanesulfonyl chloride (21 μL, 0.20 mmol, 5 equiv). The reaction vessel was sealed and heated to 45° C. After one hour, the reaction was a solid yellow gel, and another 500 μL 1,2-dichloroethane was added to form a suspension and the reaction was sealed and heated to 45° C. After 18.5 h pyrrolidine (68 μL, 0.82 mmol, 20 equiv) was added and the reaction heated to 45° C. for 2.5 hours. The solution was poured into aqueous pH 7 phosphate buffer (8 mL) and extracted with EtOAc (2×25 mL). The combined organic layers were dried ($Na_2SO_4$), filtered, and concentrated under reduced pressure. To a solution of this crude oil in $CH_3CN$ (1.8 mL) was added an aqueous solution of HF (50%, 300 μL). After 15 h, the reaction solution was poured into an aqueous $K_2HPO_4$ solution (3.6 g in 30 mL) and extracted with EtOAc (3×15 mL). The combined organic layers were dried ($Na_2SO_4$), filtered, and concentrated under reduced pressure. Palladium on carbon (10%, 8.4 mg) was added to a solution of this oil in dioxane:MeOH (1:1, 1.2 mL). The flask was fitted with a septum and evacuated and back-filled three times with hydrogen gas, and the reaction mixture was stirred under an atmosphere (balloon) of hydrogen gas for 1.5 h. Another 10 mg palladium catalyst was added and the reaction was evacuated and back-filled with hydrogen gas as before. After 6 h, the reaction mixture was filtered through celite to remove the palladium catalyst and concentrated under reduced pressure. Preparative reverse phase HPLC purification of the resulting oil was performed on a Waters Autopurification system using a Polymerx 10μ RP-γ 100 R column [30×21.20 mm, 10 micron, solvent A: 0.05 N HCl in water, solvent B: $CH_3CN$; injection volume: 3.5 mL (0.05 N HCl in water); gradient elution with 0-400% B over 10 min, then held at 100% for 5 min; mass-directed fraction collection]. Two sets of fractions with the desired MW, eluting at 6.3-7.1 min and 8.7-9.3 min, were collected separately and freeze-dried to provide 9.7 mg of crude compounds 105. Purification via preparative reverse phase HPLC with gradient elution with 20→70% B over 20 min; mass-directed fraction collection] provided 3.3 mg of pure 105 (13%): $^1$H NMR (400 MHz, $CD_3OD$) δ 7.44 (d, J=9.8 Hz, 1H), 4.09 (s, 1H), 3.79-3.65 (m, 4H), 3.63-3.56 (m, 2H), 3.18-2.90 (m, 11H), 2.35-2.26 (m, 1H), 2.26-2.10 (m, 3H), 2.10-1.96 (m, 2H), 1.69-1.59 (m, 1H); MS (ESI) m/z 609.36 (M+H).

Compound 106

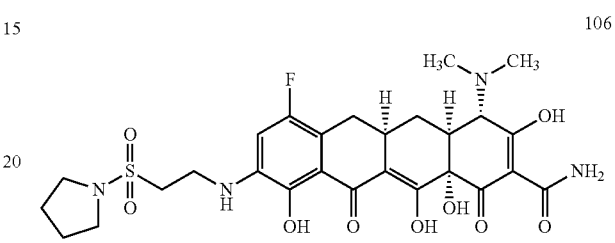

Compound 106 (1.7 mg, 7%) was also isolated from the preparation of compound 105: $^1$H NMR (400 MHz, $CD_3OD$) δ 6.71 (d, J=11.0 Hz, 1H), 4.06 (s, 1H), 3.67-3.60 (m, 2H), 3.38-3.33 (m, 4H), 3.09-2.90 (m, 9H), 2.24-2.13 (m, 2H), 1.95-1.91 (m, 5H), 1.90-1.85 (m, 1H), 1.68-1.55 (m, 1H); MS (ESI) m/z 609.36 (M+H).

Example 6

Synthesis of Compounds 107 and 108

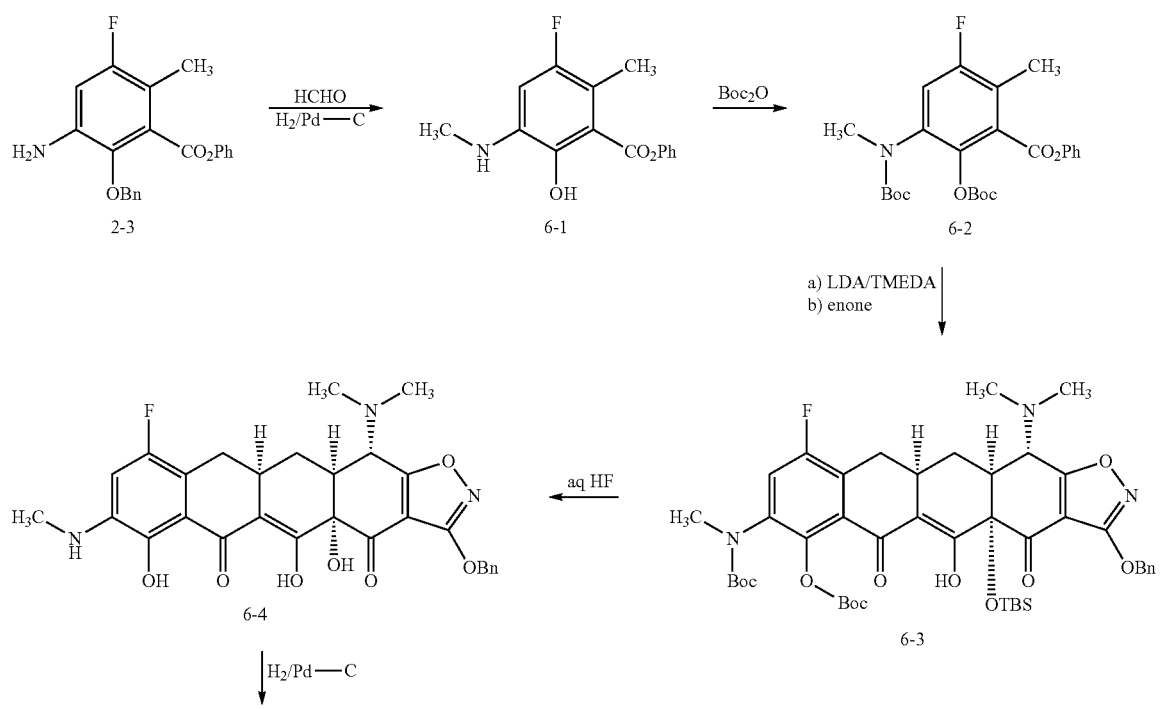

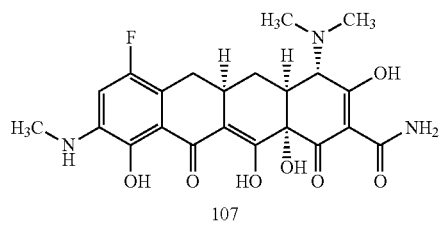

107

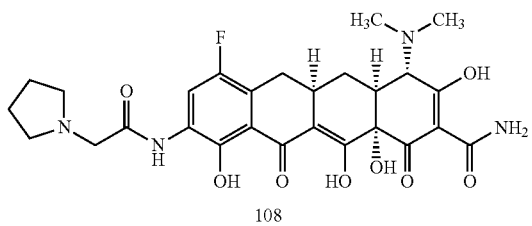

108

The following compounds were prepared according to Scheme 6.

Compound 6-1

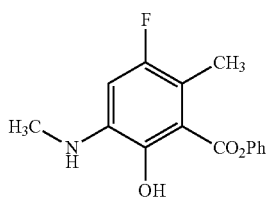
6-1

Compound 2-3 (5.0 g, 14.25 mmol, 1.0 equiv) in MeOH (20 mL) was added a aqueous solution of HCHO (2.3 g, 37%, 28.50 mmol, 2.0 equiv) and palladium on carbon (0.5 g, 10 wt %). The reaction was purged with hydrogen and stirred under H₂ (balloon) at room temperature for 2 hours. The reaction mixture was filtered through celite and concentrated to afford 1.3 g crude compound 6-1 as a yellow solid.

Compound 6-2

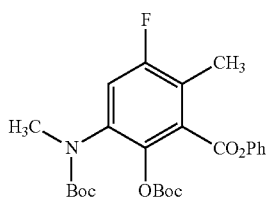
6-2

To compound 6-1 (0.9 g, 3.27 mmol, 1.0 equiv) in DCM was added Boc₂O (2.14 g, 9.81 mmol, 3.0 equiv) dropwise. DMAP (135 mg, 15 wt %) was added to the mixture and the reaction was stirred at room temperature for 1 hour. Then the reaction mixture was heated to reflux for 1 hour. The reaction mixture was concentrated. The crude compound was purified by column chromatography on silica gel eluted with (PE: EA=200:1→100:1) to yield compound 6-2 (1.16 g, 73.4%) as a light yellow solid. ¹H NMR (400 MHz, DMSO) δ 7.60 (d, J=10.0 Hz, 1H), 7.53-7.44 (m, 2H), 7.36-7.31 (m, 1H), 7.28-7.22 (m, 2H), 3.06 (s, 3H), 2.33 (d, J=2.0 Hz, 3H), 1.38 (s, 9H), 1.34 (s, 9H); MS (ESI) m/z 476.2 (M+H).

Compound 6-3

6-3

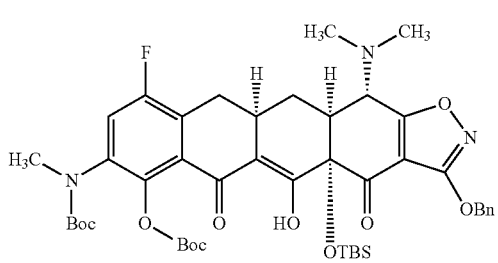

To diisopropylamine (0.28 mL, 3.2 mmol, 10.0 equiv) in THF at −78° C. was added nBuLi (0.8 mL, 2.50 M/hexane, 3.2 mmol, 10.0 equiv) and TMEDA (0.40 mL, 5.0 mmol, 10.0 equiv) at −78 C dropwise. The reaction was stirred at −78 C for 40 min. Compound 6-2 (480 mg, 1.0 mmol, 3.0 equiv) in THF was added to the reaction mixture dropwise at −78 C. The resulting deep-red solution was stirred at −78° C. 60 min, the enone (160 mg 0.33 mmol, 1.0 equiv) in THF was added to the mixture dropwise at −78 C. The deep-red solution was gradually warmed up with stirring from −78 C to −20° C. over a period of 1 h. The resulting orange solution was brought to 0° C., and quenched with aqueous saturated ammonium chloride (100 mL). The yellow-green mixture was extracted with EtOAc two times. The combined EtOAc extracts were dried (Na₂SO₄) and concentrated to yield the crude product. Flash column chromatography on silica gel with 0%, 5%, 10%, EtOAc/hexane sequentially yielded the desired product 6-3 as a light-yellow solid (42 mg, 14.8%). ¹H NMR (400 MHz, CDCl₃) δ 15.70 (s, 1H), 7.52-7.50 (m, 2H), 7.42-7.33 (m, 3H), 7.16 (d, J=8.4 Hz, 1H), 5.37 (s, 2H), 3.95 (d, J=10.8 Hz, 1H), 3.28-3.23 (m, 1H), 3.14 (s, 3H), 3.10-3.05 (m, 1H), 2.58-2.47 (m, 9H), 2.16 (d, J=14.0 Hz, 1H), 1.53 (s, 9H), 1.42 (s, 9H), 0.89 (s, 9H), 0.29 (s, 3H), 0.15 (s, 3H); MS (ESI) m/z 864.43 (M+H).

Compound 107

107

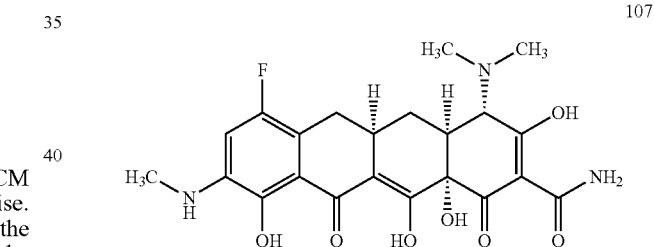

Compound 6-3 (120 mg, 0.14 mmol) was dissolved in THF (5 mL) and aqueous HF (40%, 2 mL) was added dropwise. The yellow solution was stirred at room temperature overnight. The resulting deep-red solution was slowly added into an aqueous K₂HPO₄ solution with stirring. The pH of the mixture was adjusted by aqueous K₂HPO₄ solution to about 8. The yellow mixture was extracted with EtOAc two times. The combined EtOAc extracts were dried (Na₂SO₄) and concentrated to yield the crude product.

The above crude compound (120 mg, crude, ~0.14 mmol, 1.0 equiv) was dissolved in HPLC grade MeOH (10 mL) and 10% Pd—C (25 mg, 0.03 mmol, 0.2 equiv) were added. The mixture was purged with hydrogen by bubbling hydrogen through with gentle stirring for 5 min. The reaction was then vigorously stirred under hydrogen balloon at room temperature for 2 hr. LC-MS analysis indicated the reaction completed. The catalyst was filtered off and the mixture was concentrated, the residue was purified by reverse phase HPLC to afford the desired compound 107 (50 mg, 78%) as a yellow solid. ¹H NMR (400 MHz, CD₃OD) δ 7.462 (d, J=8.4 Hz, 1H), 4.14 (s, 1H), 3.21-2.93 (m, 9H), 3.10 (s, 3H), 2.38-2.25 (m, 2H), 1.68-1.62 (m, 1H); MS (ESI) m/z 462.2 (M+H).

Compound 108

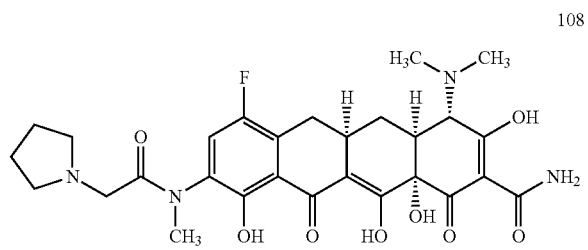

Compound 107 (15 mg, 0.033 mmol, 1.0 equiv) in THF (2 mL) was added with pyrrolidin-1-yl-acetic acid (10.2 mg, 0.066 mmol, 2.0 equiv), Na$_2$CO$_3$ (10.2 mg, 0.066 mmol, 2.0 equiv) and HATU (25.5 mg, 0.066 mmol, 2.0 equiv). The reaction mixture was stirred at room temperature for 48 hours. LC-MS analysis indicated the reaction completed. The reaction mixture was concentrated under vacuum, the crude product was purified by reverse phase HPLC to afford the desired compound 108 (2.1 mg) as a yellow solid. $^1$H NMR (400 MHz, CD$_3$OD) δ 7.44-7.40 (m, 1H), 4.02-3.97 (m, 2H), 3.83-3.76 (m, 1H), 3.60-3.58 (m, 2H), 3.15 (d, J=6.4 Hz, 3H), 3.03-2.83 (m, 11H), 2.31-2.13 (m, 2H), 2.03-1.85 (m, 4H), 1.61-1.52 (m, 1H); MS (ESI) m/z 572.9 (M+H).

Example 7

Synthesis of Compounds 109-112

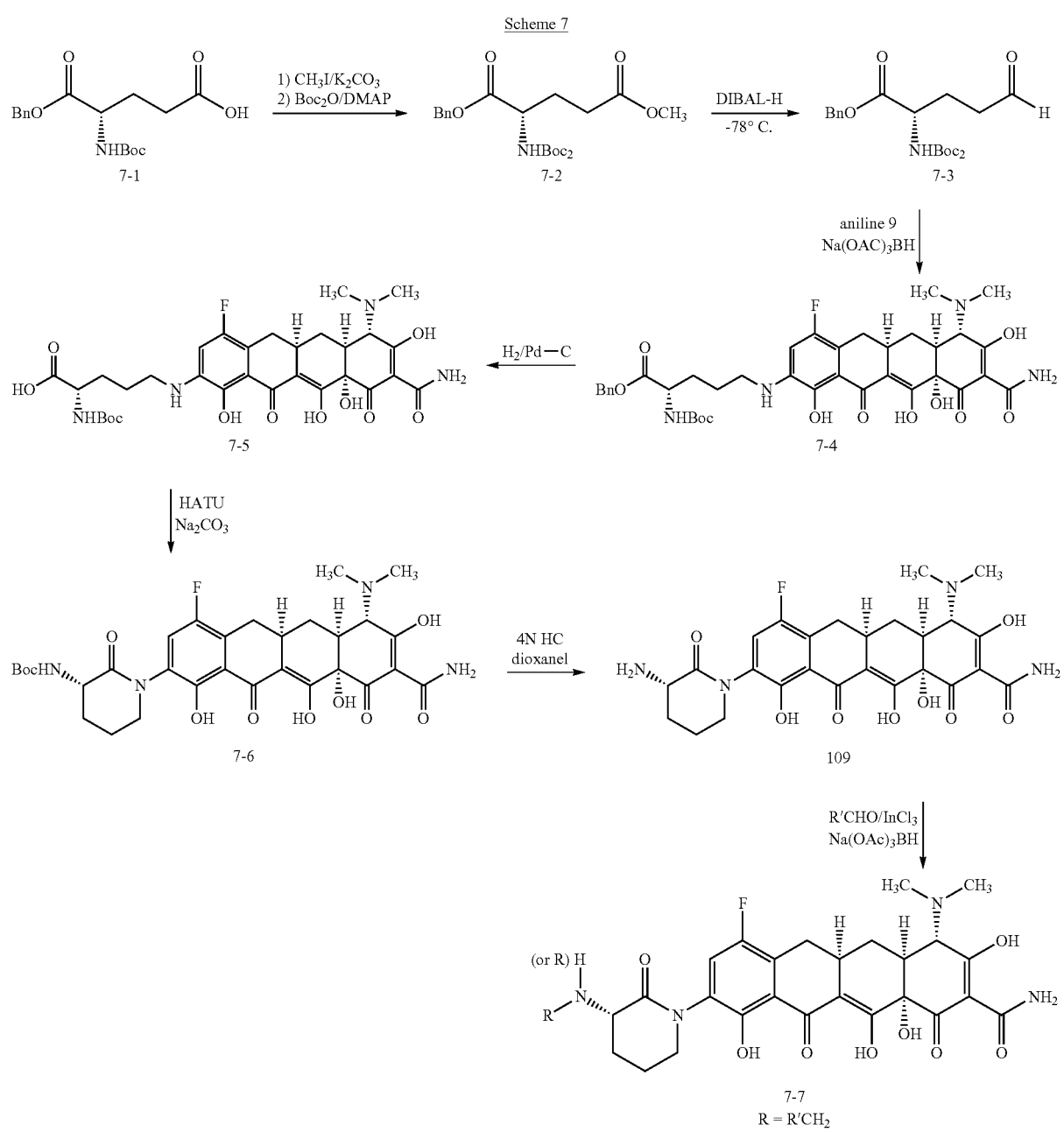

The following compounds were prepared according to Scheme 7.

Compound 7-2

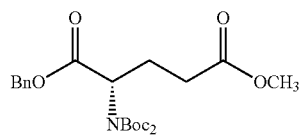

7-2

To Boc-L-glutamic acid-1-benzyl ester (7-1) (3.00 g, 8.89 mmol, 1.0 eq) in DMF (20 mL) at rt was added potassium carbonate (1.84 g, 13.33 mmol, 1.5 eq) and methyl iodide (0.67 mL, 10.74 mmol, 1.2 eq). The mixture was diluted with EtOAc (200 mL), washed with water (200 mL), saturated aqueous sodium bicarbonate (100 mL×2), and brine (100 mL×1). The EtOAc solution was dried over sodium sulfate and concentrated in vacuo: $R_f$ 0.33 (20% EtOAc/hexane).

Boc$_2$O (2.91 g, 13.33 mmol, 1.5 eq), DMAP (54 mg, 0.44 mmol, 0.05 eq), and DIEA (3.10 mL, 17.80 mmol, 2 eq) were added to the above intermediate in acetonitrile (20 mL). The solution was stirred at rt for 60 hrs, added with saturated aqueous sodium bicarbonate (100 mL), and extracted with EtOAc (100 mL×1, 50 mL×2). The EtOAc extracts were combined, dried over sodium sulfate, and concentrated in vacuo to yield the desired product 7-2 as a pale liquid (quantitative): $R_f$ 0.45 (20% EtOAc/hexane); $^1$H NMR (400 MHz, CDCl$_3$) δ 7.25-7.35 (m, 5H), 5.14 (s, 2H), 4.95 (dd, J=4.9, 9.8 Hz, 1H), 3.65 (s, 3H), 2.43-2.52 (m, 1H), 2.37-2.42 (m, 2H), 2.15-2.25 (m, 1H), 1.42 (s, 18H); MS (ESI) m/z 452.3 (M+H).

Compound 7-3

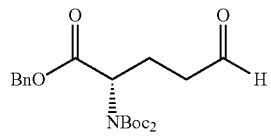

7-3

To compound 7-2 (8.89 mmol, 1 eq) in anhydrous diethyl ether (40 mL) at −78° C. was added DIBAL-H (12.33 mL, 1 M/hexane, 12.33 mmol, 1.25 eq) dropwise. The reaction was stirred at −78° C. for 2 hrs. Additional DIBAL-H (1.20 mL, 1 M/hexane, 1.20 mmol) was added. The reaction was stirred at −78° C. for another 1 hr and quenched with HOAc (2.80 mL) at −78° C. The reaction was warmed to rt and added with 10% aqueous sodium carbonate (75 mL). The mixture was stirred for 15 min and extracted with methylene chloride (200 mL×1, 50 mL×2). The methylene chloride extracts were combined, dried over sodium sulfate, and concentrated in vacuo to yield the desired product 7-3 (quantitative): $R_f$ 0.40 (20% EtOAc/hexane); $^1$H NMR (400 MHz, CDCl$_3$) δ 9.75 (s, 1H), 7.25-7.35 (m, 5H), 5.14 (s, 2H), 4.87-4.92 (m, 1H), 2.45-2.65 (m, 3H), 2.12-2.22 (m, 1H), 1.42 (s, 18H); MS (ESI) m/z 422.3 (M+H).

Compound 7-5

7-5

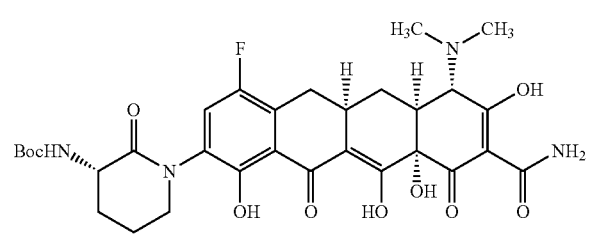

To aniline 9 (90 mg, 0.20 mmol, bis-HCl salt, 1 eq) in anhydrous DMF (2 mL) was added aldehyde 7-3 (101 mg, 0.24 mmol, 1.2 eq), triethylamine (0.028 mL, 0.20 mmol, 1 eq), and Na(OAc)$_3$BH (64 mg, 0.30 mmol, 1.5 eq). The solution was stirred at rt for 1 hr and added slowly into diethyl ether (50 mL) with rapid stirring. The yellow solid was collected, washed with more diethyl ether (5 mL×3), and dried under vacuum to afford the intermediate 7-4.

Intermediate 7-4 was dissolved in dioxane/methanol (5 mL, 1:4 v/v, containing 0.1 N HCl). 10% Pd—C (85 mg, 0.04 mmol, 0.2 eq) was added. The mixture was purged with hydrogen and stirred under 1 atm hydrogen at rt for 1 hr. The catalyst was filtered with a small Celite pad and washed with methanol (2 mL×3). The filtrate was concentrated in vacuo. The crude product was purified by reverse phase preparative HPLC using methanol and 0.05 N HCl/water as mobile phases. Free-drying yielded mostly the Boc-deprotected product as a brown solid (25 mg, 22%, 2 steps), which was re-protected by treatment with Boc$_2$O (11 mg, 0.050 mmol, 1.1 eq) and DIEA (0.039 mL, 0.22 mmol, 5 eq) in THF/water (5 mL, 1:1 v/v) at rt for 1 hr. Concentration yielded the desired product 7-5 as a yellow solid: MS (ESI) m/z 663.2 (M+H), which was used directly in the subsequent steps without further purification.

Compound 7-6

7-6

To a suspension of compound 7-5 (0.044 mmol, 1 eq) and sodium carbonate (7 mg, 0.066 mmol, 1.5 eq) in THF at rt was added HATU (20 mg, 0.053 mmol, 1.2 eq). The mixture was rapidly stirred at rt for 2 hrs. Methanol (5 mL) was added. The solids were filtered off. The filtrate was concentrated under reduced pressure to yield crude 7-6 as a yellow solid: MS (ESI) m/z 645.1 (M+H).

Compound 109

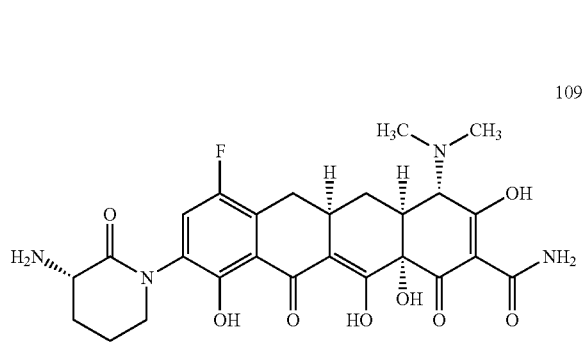

109

Compound 7-6 (0.044 mmol) was treated with 4 N HCl/dioxane (5 mL) at rt for overnight and concentrated in vacuo. The residue was re-dissolved in methanol (1 mL) and added dropwise into diethyl ether (50 mL) with rapid stirring. The yellow precipitates were collected, washed with more diethyl ether (5 mL×3), and dried under vacuo to afford crude 109 as a brown solid.

One fifth of the above crude product was purified by reverse phase HPLC to yield pure 109 as a yellow solid (1.5 mg, 31%): $^1$H NMR (400 MHz, CD$_3$OD) δ 7.36 (d, 9.2 Hz, 1H), 4.09-4.15 (m, 1H), 4.08 (s, 1H), 3.70-3.80 (m, 1H), 3.58-3.68 (m, 1H), 2.90-3.50 (m, 12H), 2.30-2.45 (m, 2H), 2.10-2.25 (m, 3H), 1.95-2.10 (m, 1H), 1.58-1.70 (m, 1H); MS (ESI) m/z 545.1 (M+H).

Compound 110

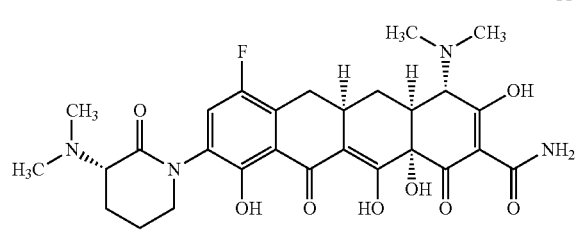

110

To ⅖ of crude 109 (0.018 mmol, 1 eq) in DMF (1 mL) was added aqueous formaldehyde (0.007 mL, 36.5%/water, 0.094 mmol, 5 eq), InCl$_3$ (0.4 mg, 0.002 mmol, 0.1 eq), and Na(OAc)$_3$BH (15 mg, 0.071 mmol, 4 eq). The reaction was stirred at rt for 2 hrs and quenched with 0.5 N HCl/methanol (1 mL). The solution was added dropwise into diethyl ether (100 mL) with rapid stirring. The precipitates were collected, washed with more diethyl ether (2 mL×4), and purified by reverse phase HPLC to afford the desired compound 110 as a yellow solid (1.8 mg, 18%): $^1$H NMR (400 MHz, CD$_3$OD) δ 7.7.44 (d, J=9.1 Hz, 1H), 4.37 (dd, J=6.1, 11.6 Hz, 1H), 4.09 (s, 1H), 3.60-3.75 (m, 2H), 2.92-3.50 (m, 15H), 2.86 (s, 3H), 2.10-2.50 (m, 6H), 1.60-1.72 (m, 1H); MS (ESI) m/z 573.3 (M+H).

Compound 111

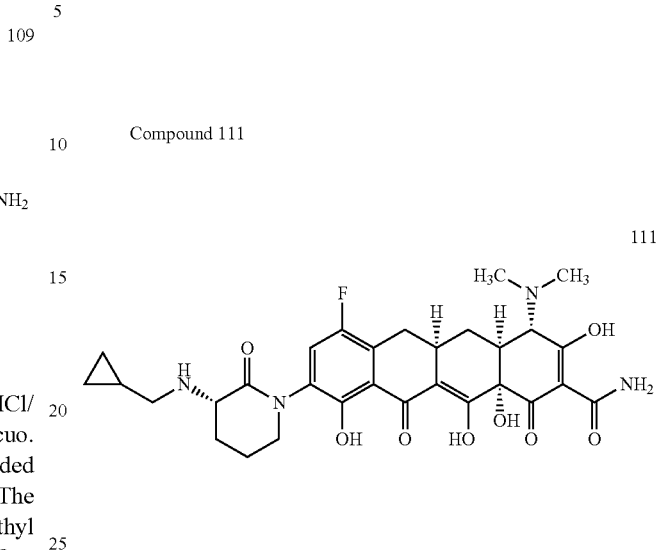

111

To ⅖ of crude 109 (0.018 mmol, 1 eq) in DMF (1 mL) was added cyclopropanecarboxaldehyde (1.4 μL, 0.018 mmol, 1 eq), InCl$_3$ (0.4 mg, 0.002 mmol, 0.1 eq), and Na(OAc)$_3$BH (6 mg, 0.028 mmol, 1.5 eq). The reaction was stirred at rt for overnight and quenched with 0.5 N HCl/methanol (1 mL). The solution was added dropwise into diethyl ether (100 mL) with rapid stirring. The precipitates were collected, washed with more diethyl ether (2 mL×4), and purified by reverse phase HPLC to afford the desired compound III as a yellow solid (1.3 mg, 12%): $^1$H NMR (400 MHz, CD$_3$OD) δ 7.38 (d, J=9.2 Hz, 1H), 4.22 (dd, J=6.1, 11.6 Hz, 1H), 4.09 (d, 1H), 3.60-3.78 (m, 2H), 2.85-3.50 (m, 12H), 2.00-2.50 (m, 6H), 1.60-1.72 (m, 1H), 1.10-1.20 (m, 1H), 0.70-0.75 (m, 2H), 0.40-0.50 (m, 2H); MS (ESI) m/z 599.4 (M+H).

Compound 112

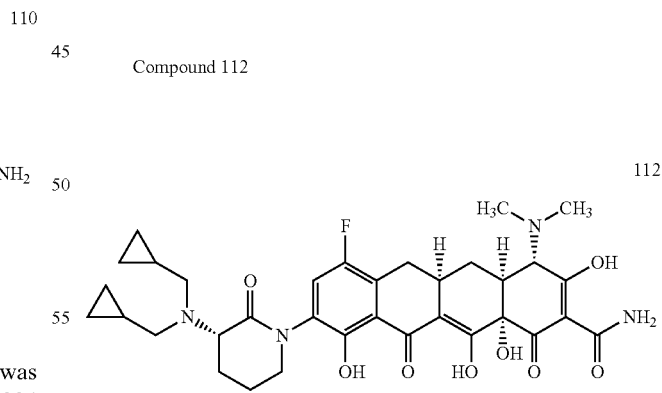

112

Dialkylated product 112 was also isolated from the preparation of compound III (1.0 mg, yellow solid, 9%): $^1$H NMR (400 MHz, CD$_3$OD) δ 7.42 (d, J=9.2 Hz, 1H), 4.70-4.80 (m, 1H), 4.09 (s, 1H), 3.55-3.80 (m, 3H), 2.95-3.50 (m, 13H), 2.10-2.50 (m, 6H), 1.55-1.75 (m, 1H), 1.20-1.30 (m, 2H), 0.68-0.90 (m, 4H), 0.38-0.58 (m, 4H); MS (ESI) m/z 653.3 (M+H).

Example 8

Synthesis of Compounds of Structrual Formula (A), Wherein Y is —(C$_1$-C$_4$)alkylene-N(R$^A$)(R$^B$), or —(C$_1$-C$_4$)alkylene-N(R$^F$)—C(O)—[C(R$^D$)(R$^E$)]$_{0-4}$—N(R$^A$)(R$^B$)

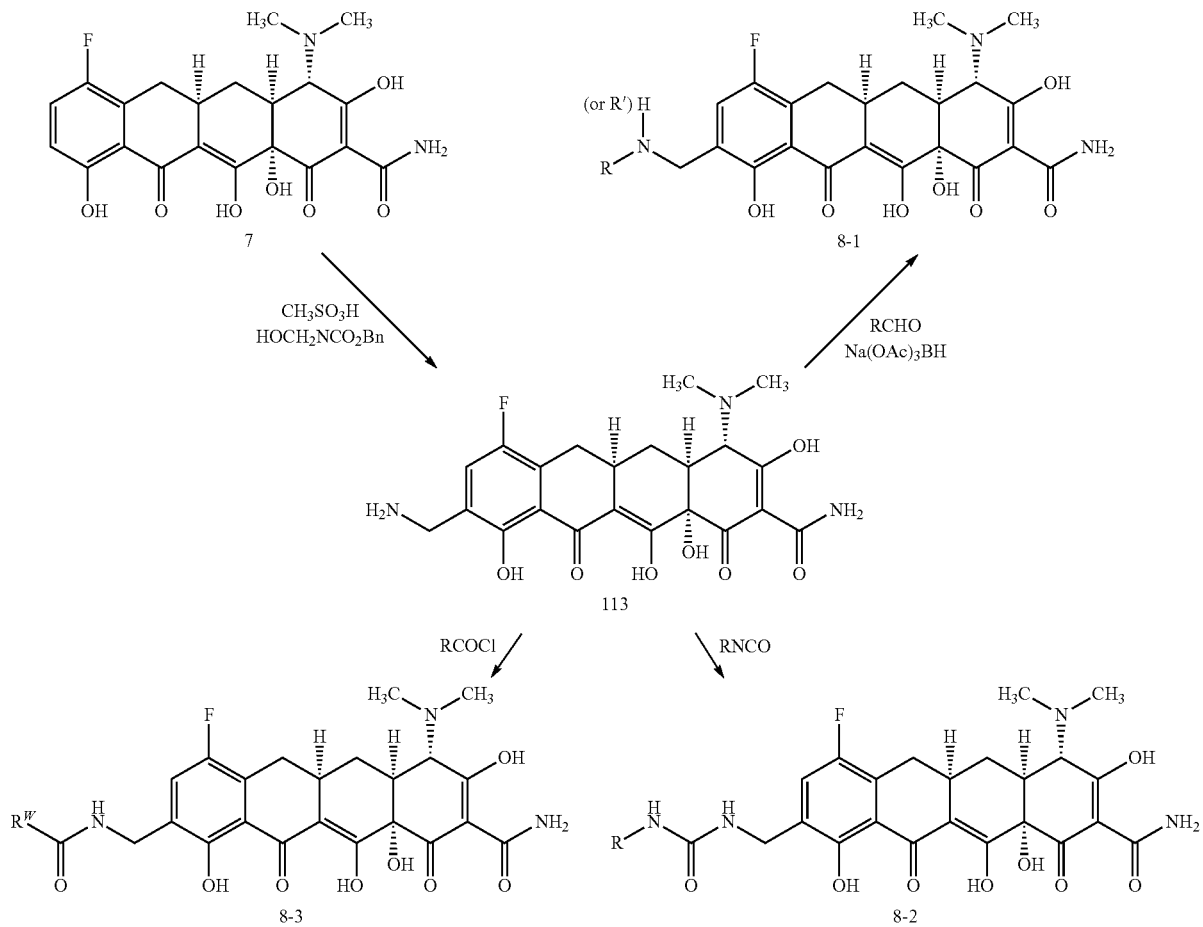

Scheme 8

In Scheme 8, R and R' is R$^B$ and R$^A$, respectively, as defined in Structural Formula (A) and R$^W$ represents —[C(R$^D$)(R$^E$)]$_{1-4}$—N(R$^A$)(R$^B$).

The following compounds were prepared according to Scheme 8.

Compound 113

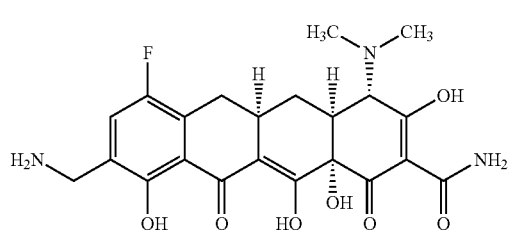

Benzyl N-(hydroxymethyl)carbamate (92 mg, 0.51 mmol, 2.0 equiv) was added to a TFA/CH$_3$SO$_3$H (1 mL/1 mL) solution of compound 7 (110 mg, 0.25 mmol) at 25° C. The reaction was stirred at 25° C. for 30 min. Preparative reverse phase HPLC purification on a Waters Autopurification system using a Phenomenex Polymerx 10μ RP-1 100A column [10 μm, 150×21.20 mm; flow rate, 20 mL/min; Solvent A: 0.05 N HCl; Solvent B: CH$_3$CN; injection volume: 4.0 mL (0.05 N HCl/water); gradient: 0→30% B over 20 min; mass-directed fraction collection]. Fractions with the desired MW were collected and freeze-dried to yield 23 mg of pure 113: $^1$H NMR (400 MHz, CD$_3$OD) δ 7.47 (d, J=9.2 Hz, 1H), 4.16 (s, 2H), 4.13 (s, 1H), 3.21-2.94 (m, 3H), 3.06 (s, 3H), 2.97 (s, 3), 2.37-2.22 (m, 2H), 1.70-1.58 (m, 1H); MS (ESI) m/z 462.26 (M+H).

Compound 114

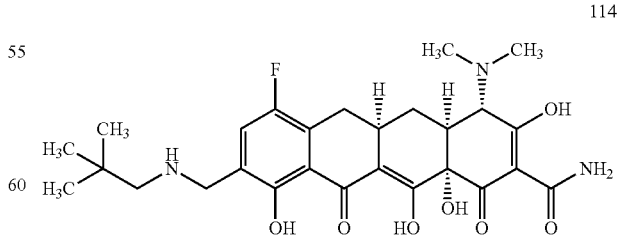

Et$_3$N (2 μL, 0.0136 mmol, 2.0 equiv) was added to a mixture of 113 (3 mg, 0.0065 mmol) and pivaldehyde (0.8 μL, 0.00715 mmol, 1.1 equiv) in DMF (0.1 mL) at 25° C. The reaction was stirred at 25° C. for 15 min. NaBH(OAc)$_3$ (3 mg, 0.013 mmol) and HOAc (2 μL) was added to the resulting mixture. The reaction was stirred at 25° C. for 1 h. Preparative reverse phase HPLC purification on a Waters Autopurification system using a Phenomenex Polymerx 10μ RP-1 100A column [10 150×21.20 mm; flow rate, 20 mL/min; Solvent A: 0.05 N HCl; Solvent B: $CH_3CN$; injection volume: 4.0 mL (0.05 N HCl/water); gradient: 0→100% B over 15 min; mass-directed fraction collection]. Fractions with the desired MW were collected and freeze-dried to yield 1 mg of 114: $^1$H NMR (400 MHz, $CD_3OD$) δ 7.52 (d, J=9.1 Hz, 1H), 4.30 (s, 2H), 4.09 (s, 1H), 3.23-2.93 (m, 5H), 3.04 (s, 3H), 2.95 (s, 3H), 2.40-2.19 (m, 2H), 1.71-1.60 (m, 1H), 1.05 (s, 9H); MS (ESI) m/z 532.27 (M+H).

Compounds 115-118 were prepared similarly to compound 114 using the corresponding aldehydes.

Compound 115

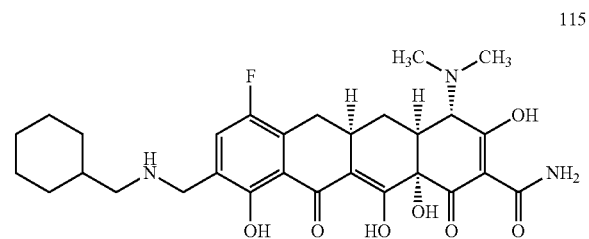

115

$^1$H NMR (400 MHz, $CD_3OD$) δ 7.51 (d, J=8.8 Hz, 1H), 4.25 (s, 2H), 4.10 (s, 1H), 3.25-2.90 (m, 5H), 3.05 (s, 3H), 2.96 (s, 3H), 2.40-2.21 (m, 2H), 1.90-1.60 (m, 7H), 1.42-0.95 (m, 5H); MS (ESI) m/z 558.31 (M+H).

Compound 116

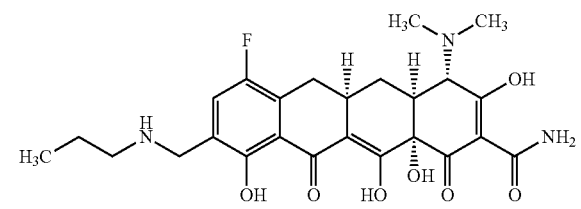

116

$^1$H NMR (400 MHz, $CD_3OD$) δ 7.50 (d, J=9.0 Hz, 1H), 4.24 (s, 2H), 4.09 (s, 1H), 3.25-2.90 (m, 5H), 3.07 (s, 3H), 2.94 (s, 3H), 2.40-2.21 (m, 2H), 1.82-1.58 (m, 3H), 1.01 (t, J=6.7 Hz, 3H); MS (ESI) m/z 504.22 (M+H).

Compound 117

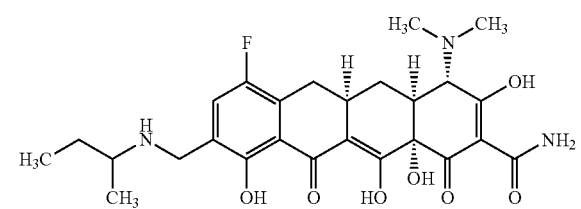

117

$^1$H NMR (400 MHz, $CD_3OD$) δ 7.51 (d, J=8.9 Hz, 1H), 4.23 (s, 2H), 4.09 (s, 1H), 3.25-2.92 (m, 4), 3.02 (s, 3H), 2.95 (s, 3H), 2.40-2.19 (m, 2H), 1.71-1.60 (m, 1H), 1.40 (d, J=7.0 Hz, 6H); MS (ESI) m/z 504.23 (M+H).

Compound 118

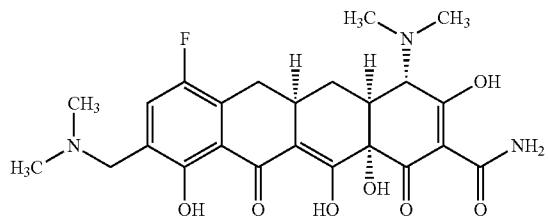

118

$^1$H NMR (400 MHz, $CD_3OD$) δ 7.54 (d, J=9.1 Hz, 1H), 4.37 (s, 2H), 4.10 (s, 1H), 3.20-2.85 (m, 3H), 3.05 (s, 3H), 2.97 (s, 3H), 2.91 (s, 3H), 2.90 (s, 3H), 2.42-2.20 (m, 2H), 1.72-1.60 (m, 1H); MS (ESI) m/z 490.19 (M+H).

Compound 119

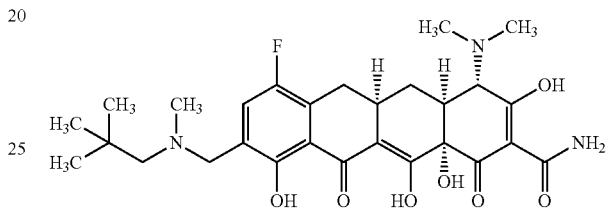

119

Prepared from compound 114 by reductive alkylation using formaldehyde under similar conditions: $^1$H NMR (400 MHz, $CD_3OD$) δ 7.57 (d, J=9.1 Hz, 1H), 4.61 (d, J=12.8 Hz, 1H), 4.27 (dd, J=12.8, 6.4 Hz, 1H), 4.10 (s, 1H), 3.25-2.90 (m, 5), 3.03 (s, 3H), 2.96 (s, 3H), 2.95 (s, 3H), 2.42-2.33 (m, 1H), 2.29-2.20 (m, 1H), 1.72-1.61 (m, 1H), 1.10 (d, J=6 Hz, 9H); MS (ESI) m/z 546.30 (M+H).

Compound 120

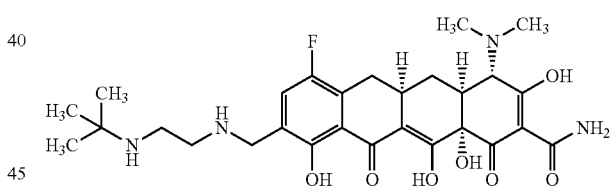

120

Prepared similarly to 114 by reductive alkylation of 113 with t-Bu-N(Cbz)-$CH_2CHO$ followed by hydrogenation: $^1$H NMR (400 MHz, $CD_3OD$) δ 7.59 (d, J=8.6 Hz, 1H), 4.38 (s, 2H), 4.09 (s, 1H), 3.60-2.95 (m, 7H), 3.03 (s, 3H), 2.96 (s, 3H), 2.41-2.30 (m, 1H), 2.28-2.20 (m, 1H), 1.72-1.60 (m, 1H), 1.44 (s, 9H); MS (ESI) m/z 561.31 (M+H).

Compound 121

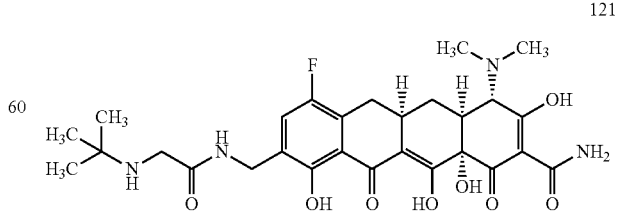

121

2-t-Butylaminoacetylchloride hydrochloride (5.8 mg, 0.031 mmol, 1.2 equiv) was added to a DMF solution (0.2 mL) of 113 (12 mg, 0.026 mmol) at 25° C. The reaction was stirred at 25° C. for 30 min. The reaction mixture was diluted with 0.05 N HCl (2 mL) and injected into a Waters Autopurification system equipped with a Phenomenex Polymerx 10µ RP-1 100A column [10 µm, 150×21.20 mm; flow rate, 20 mL/min; Solvent A: 0.05 N HCl; Solvent B: CH$_3$CN; gradient: 0→100% B over 15 min; mass-directed fraction collection]. Fractions with the desired MW were collected and freeze-dried to yield 3.0 mg of pure 121: $^1$H NMR (400 MHz, CD$_3$OD) δ 7.34 (d, J=9.6 Hz, 1H), 4.46 (s, 2H), 4.08 (s, 1H), 3.81 (s, 2H), 3.18-2.92 (m, 3H), 3.03 (s, 3H), 2.96 (s, 3H), 2.32-2.18 (m, 2H), 1.69-1.60 (m, 1H), 1.38 (s, 9H); MS (ESI) m/z 575.30 (M+H).

Compound 122

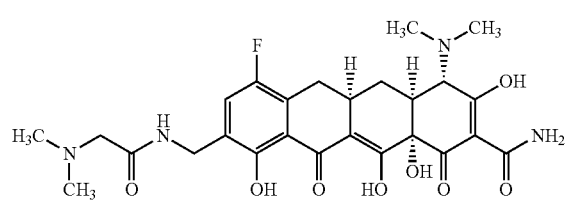

122

Prepared similarly to compound 121: $^1$H NMR (400 MHz, CD$_3$OD) δ 7.33 (d, J=9.9 Hz, 1H), 4.46 (s, 2H), 4.08 (s, 1H), 4.00 (s, 2H), 3.23-2.91 (m, 3), 3.04 (s, 3H), 2.97 (s, 3H), 2.95 (s, 6H), 2.32-2.18 (m, 2H), 1.70-1.58 (m, 1H); MS (ESI) m/z 547.23 (M+H).

Compound 123

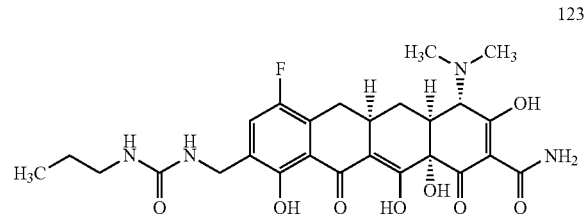

123

Prepared similarly to 121 using n-propyl isocyanate: $^1$H NMR (400 MHz, CD$_3$OD) δ 7.24 (d, J=9.8 Hz, 1H), 4.31 (s, 2H), 4.08 (s, 1H), 3.18-2.93 (m, 3H), 3.10 (t, J=6.7 Hz, 2H), 3.03 (s, 3H), 2.96 (s, 3H), 2.32-2.18 (m, 2H), 1.69-1.58 (m, 1H), 1.55-1.46 (m, 2H), 0.92 (t, J=6.7 Hz, 3H); MS (ESI) m/z 584.01 (M+H).

Example 9

Synthesis of Compounds of Structural Formula (A), Wherein Y is —(CH$_2$)$_3$—N(R$^A$)(R$^B$)

Scheme 9

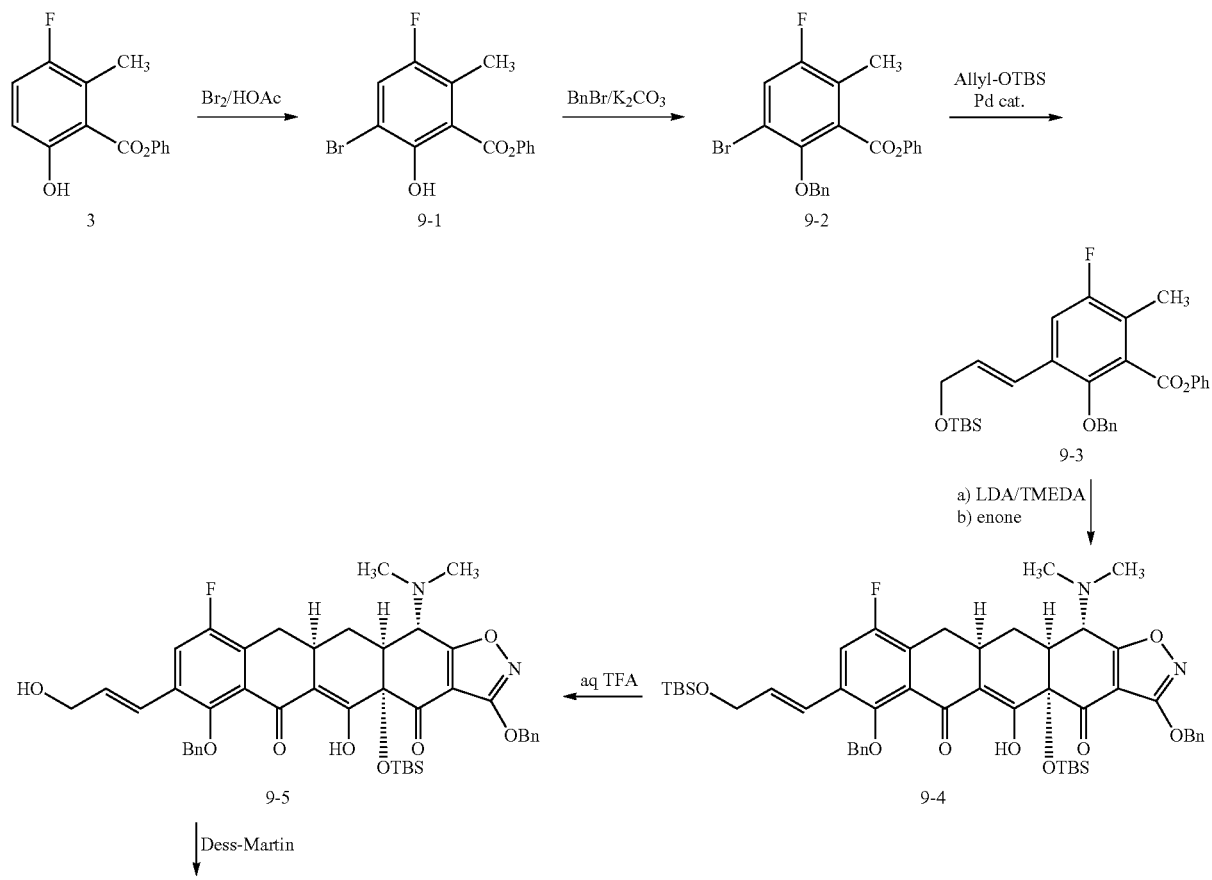

-continued

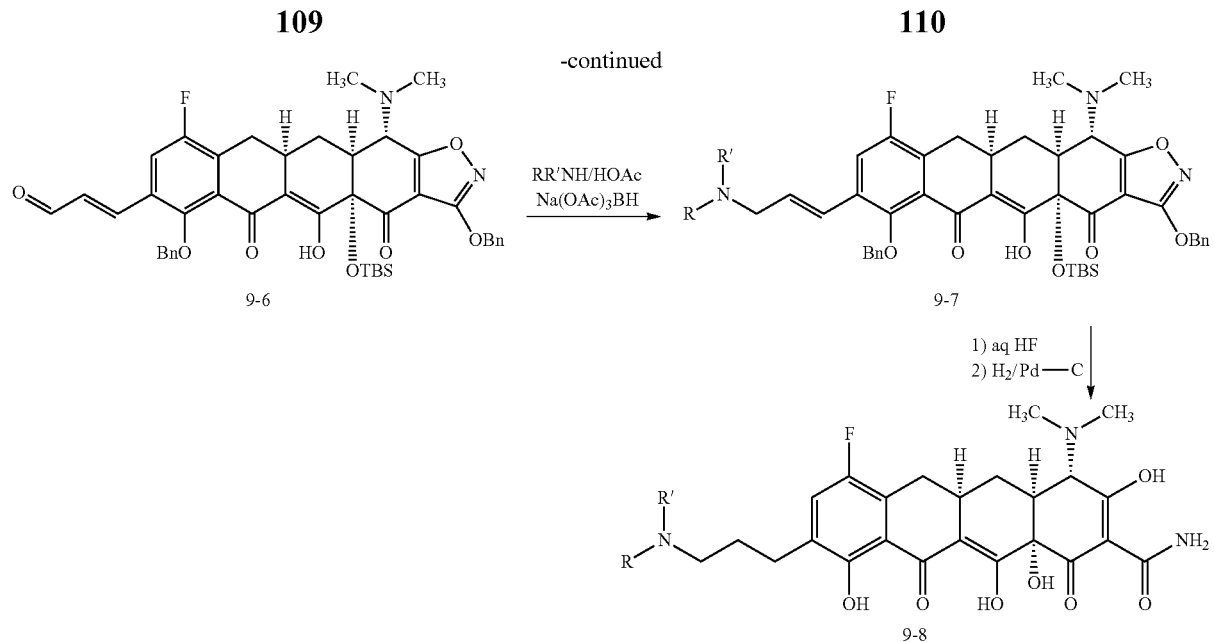

In Scheme 9, R and R' are $R^A$ and $R^B$ respectively, as defined in Structural Formula (A).

The following compounds were prepared according to Scheme 9.

Compound 9-1

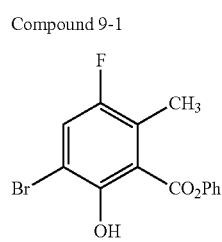

9-1

Br$_2$ (2.7 mL, 52.0 mmol, 1.2 equiv) was added to a solution of 3 (10.6 g, 43.3 mmol) in acetic acid (100 mL) at 25° C. The reaction was stirred at 25° C. for 12 h. The resulting mixture was added dropwise to ice-water (400 mL). The mixture was allowed to warm to 25° C. over 1 h. The resulting suspension was filtered through a pad of Celite. The solid was washed off with EtOAc. The combined organic layer was dried (Na$_2$SO$_4$) and concentrated to give 14 g of crude 9-1.

Compound 9-2

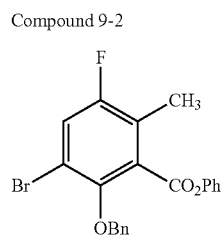

9-2

Potassium carbonate (8.9 g, 64.5 mmol, 1.5 equiv) and benzyl bromide (11.5 mL, 96.8 mmol, 2.25 equiv) were added to an acetone solution (100 mL) of crude 9-1 (14 g, 43 mmol) at 25° C. The reaction was stirred at 25° C. for 12 h and concentrated. The resulting mixture was partitioned between H$_2$O and EtOAc. The aqueous layer was extracted with EtOAc. The combined EtOAc extracts were dried (Na$_2$SO$_4$) and concentrated to yield crude 9-2. Flash chromatography on silica gel (100:1 to 30:1 hexanes/EtOAc) yielded 15.4 g of compound 9-2 (87% for 2 steps).

Compound 9-3

9-3

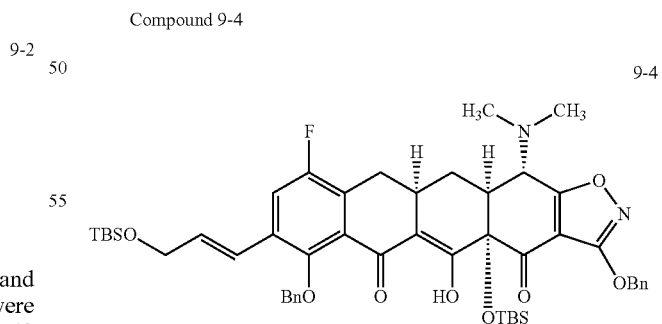

Pd(OAc)$_2$ (227 mg, 1.0 mmol, 0.2 equiv) and P(O-Tol)$_3$ (462 mg, 1.5 mmol, 0.3 euiqv) were added to a DMF solution (10 mL) of 9-2 (2.1 g, 5.06 mmol). The reaction was purged with N$_2$ for 5 min. Et$_3$N (3.5 mL, 25.3 mmol, 5 equiv) and allyloxy-t-butyldimethylsilane (2.2 mL, 10.1 mmol, 2 equiv) were added to the reaction. The reaction was heated to 88° C. and stirred at 88° C. for 5 h. The reaction was allowed to cool to 25° C. and quenched with H$_2$O. The resulting mixture was extracted with EtOAc. The combined EtOAc extracts were dried (Na$_2$SO$_4$) and concentrated to give crude 9-3. Flash chromatography on silica gel (100:0 to 100:1 hexanes/EtOAc) yielded 1.2 g of compound 9-3 (47%).

Compound 9-4

9-4 n-BuLi (1.3 mL, 2.07 mmol, 5.5 equiv) was added to a THF solution (5 mL) of diisopropylamine (0.3 mL, 2.07 mmol, 5.5 equiv) at 0° C. The reaction was stirred at 0° C. for 30 min and cooled to −78° C. TMEDA (0.8 mL, 5.64 mmol, 15 equiv) was added to the mixture. To the resulting solution was added a THF solution (5 mL) of 9-3 (475 mg, 0.94 mmol, 2.5 equiv). The reaction was stirred at −78° C. for 10 min. A THF solution (5 mL) of enone (181 mg, 0.376 mmol) was added to the reaction at −78° C. The reaction was stirred at −78° C. for 30 min and allowed to warm to 25° C. over 1 h, quenched with saturated NH₄Cl, and extracted with EtOAc. The combined EtOAc extracts were dried (Na₂SO₄) and concentrated to yield the crude product. Preparative reverse phase HPLC purification on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 100→100% B over 15 min; mass-directed fraction collection]. Fractions with the desired MW were collected and concentrated on a RotaVap at 25° C. to remove most of the acetonitrile. The resulting mostly aqueous solution was extracted with EtOAc. The combined EtOAc extracts were dried (Na₂SO₄) and concentrated to give 200 mg of 9-4 (59%).

Compound 9-5

9-5

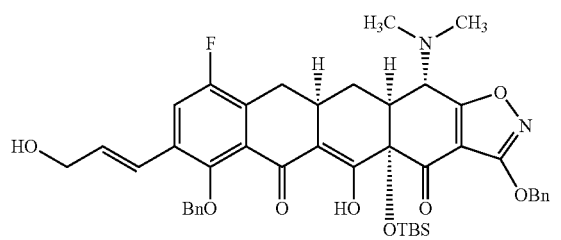

TFA (0.5 mL) was added to a THF/H₂O (2 mL/0.5 mL) solution of 9-4 at 25° C. The reaction was stirred at 25° C. for 1 h. The reaction was quenched with sat. NaHCO₃ solution. The reaction was extracted with EtOAc. The combined EtOAc extracts were dried (Na₂SO₄) and concentrated to give crude 9-5. Preparative reverse phase HPLC purification on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 80→100% B over 15 min; mass-directed fraction collection]. Fractions with the desired MW were collected and concentrated on a RotaVap at 25° C. to remove most of the acetonitrile. The resulting mostly aqueous solution was extracted with EtOAc. The combined EtOAc extracts were dried (Na₂SO₄) and concentrated to give 80 mg of 9-5 (46%).

Compound 9-6

9-6

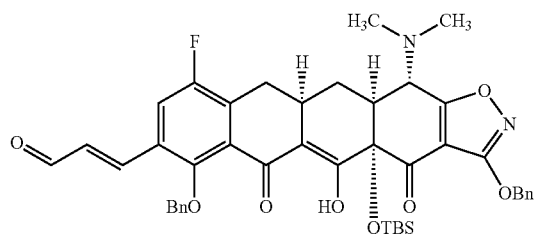

Dess-Martin periodinane (18 mg, 0.043 mmol, 1.2 equiv) was added to a CH₂Cl₂ solution (1 mL) of 9-5 (28 mg, 0.036 mmol) at 25° C. The reaction was stirred at 25° C. for 30 min and diluted with H₂O. The resulting mixture was extracted with CH₂Cl₂. The combined CH₂Cl₂ extracts were dried (Na₂SO₄) and concentrated to give crude 9-6.

Compound 9-7-1

9-7-1

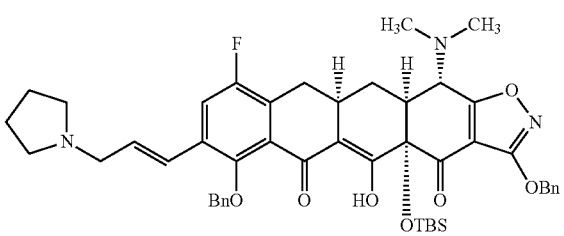

Pyrrolidine (15 μL, 0.18 mmol, 5 equiv) was added to a dichloroethane solution (1 mL) of crude 9-6 (0.036 mmol) at 25° C. The reaction was stirred at 25° C. for 10 min HOAc (15 μL) and NaBH(OAc)₃ (15 mg, 0.072 mmol, 2 equiv) were added to the reaction. The reaction mixture was stirred at 25° C. for 1 h and quenched with H₂O. The resulting mixture was extracted with CH₂Cl₂. The combined CH₂Cl₂ extracts were dried (Na₂SO₄) and concentrated to give crude 9-7-1. Preparative reverse phase HPLC purification on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 0→100% B over 15 min; mass-directed fraction collection]. Fractions with the desired MW were collected and concentrated on a RotaVap at 25° C. to remove most of the acetonitrile. The resulting mostly aqueous solution was extracted with EtOAc. The combined EtOAc extracts were dried (Na₂SO₄) and concentrated to give 6 mg of 9-7-1 (20% for 2 steps).

Compound 124

810

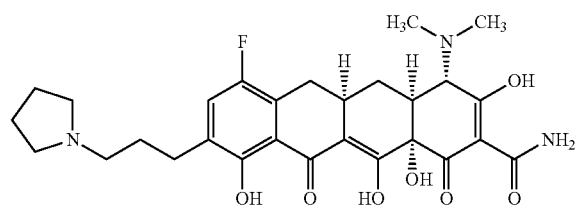

Aqueous HF (0.3 mL, 48%) was added to a CH₃CN solution (2 mL) of 9-7-1 (6 mg, 0.007 mmol) in a polypropylene tube at 25° C. The reaction was stirred at 25° C. for 18 h. The resulting mixture was poured into an aqueous solution of K₂HPO₄ (2 g, dissolved in 15 mL water). The mixture was extracted with EtOAc. The combined EtOAc extracts were dried (Na₂SO₄) and concentrated to yield crude desilyl product.

Palladium on carbon (2 mg, 10 wt %) was added to a HCl/MeOH solution (0.5N, 2 mL) of the crude desilyl product. The reaction was purged with hydrogen and stirred under H₂ (balloon) at 25° C. for 4 h. The reaction mixture was filtered through a small Celite plug. The filtrate was concentrated to yield the crude product. Preparative reverse phase HPLC purification on a Waters Autopurification system using a Phenomenex Polymerx 10μ RP-1 100A column [10 μm, 150×21.20 mm; flow rate, 20 mL/min; Solvent A: 0.05 N HCl/water; Solvent B: CH$_3$CN; injection volume: 4.0 mL (0.05 N HCl/water); gradient: 0→50% B over 7 min, 50→100% over 3 min, and 100% over 5 min; mass-directed fraction collection]. Fractions with the desired MW, eluting at 6.4-8.2 min, were collected and freeze-dried to yield 1.5 mg of compound 124: $^1$H NMR (400 MHz, CD$_3$OD) δ 7.28 (d, J=9.7 Hz, 1H), 4.08 (s, 1H), 3.71-3.63 (m, 2H), 3.32-2.95 (m, 7H), 3.04 (s, 3H), 2.96 (s, 3H), 2.81-2.73 (m, 2H), 2.32-1.98 (m, 8H), 1.70-1.59 (m, 1H); MS (ESI) m/z 544.18 (M+H).

Compounds 125-127 were prepared similarly to compound 124 using the corresponding amines in the reductive amination step.

Compound 125

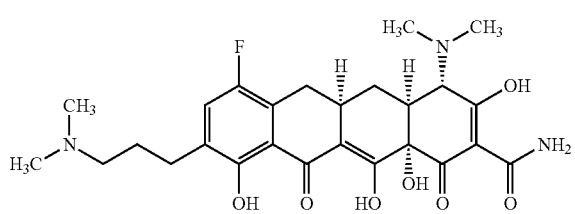

125

$^1$H NMR (400 MHz, CD$_3$OD) δ 7.28 (d, J=9.7 Hz, 1H), 4.08 (s, 1H), 3.25-2.94 (m, 5H), 3.04 (s, 3H), 2.96 (s, 3H), 2.89 (s, 6H), 2.80-2.70 (m, 2H), 2.32-2.18 (m, 2H), 2.10-2.00 (m, 2H), 1.70-1.58 (m, 1H); MS (ESI) m/z 518.26 (M+H).

Compound 126

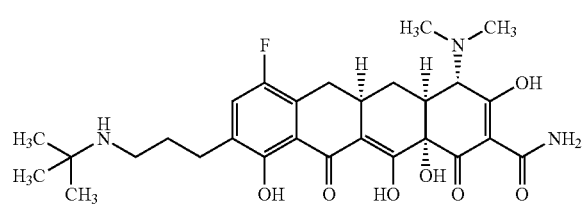

126

$^1$H NMR (400 MHz, CD$_3$OD) δ 7.27 (d, J=9.6 Hz, 1H), 4.08 (s, 1H), 3.20-2.93 (m, 5H), 3.04 (s, 3H), 2.96 (s, 3H), 2.82-2.72 (m, 2H), 2.33-2.19 (m, 2H), 2.04-1.94 (m, 2H), 1.70-1.58 (m, 2H), 1.37 (s, 9H); MS (ESI) m/z 546.20 (M+H).

Compound 127

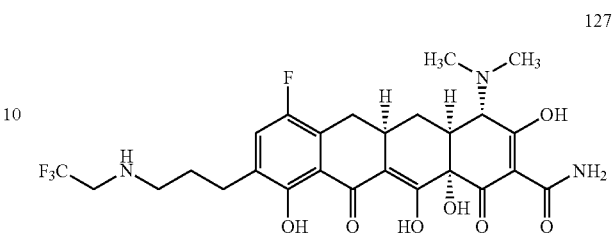

127

$^1$H NMR (400 MHz, CD$_3$OD) δ 7.28 (d, J=9.7 Hz, 1H), 4.09 (s, 1H), 4.04 (q, J=9.0 Hz, 2H), 3.25-2.95 (m, 5H), 3.04 (s, 3H), 2.97 (s, 3H), 2.84-2.75 (m, 2H), 2.32-2.20 (m, 2H), 2.13-2.03 (m, 2H), 1.70-1.58 (m, 1H); MS (ESI) m/z 572.22 (M+H).

Compound 128

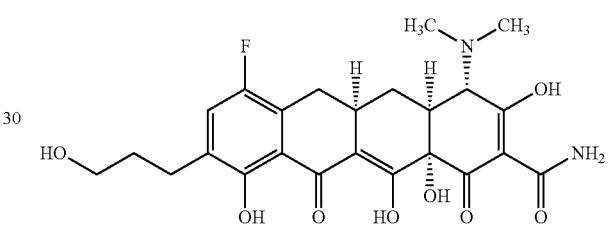

128

Compound 128 was prepared from compound 9-5 by HF treatment following by hydrogenation under similar conditions: $^1$H NMR (400 MHz, CD$_3$OD) δ 7.21 (d, J=9.87 Hz, 1H), 4.07 (s, 1H), 3.63-3.57 (m, 2H), 3.20-2.90 (m, 5H), 3.04 (s, 3H), 2.96 (s, 3H), 2.75-2.68 (m, 2H), 2.32-2.17 (m, 2H), 1.89-1.79 (m, 2H), 1.70-1.57 (m, 1H), 1.25 (d, J=7.2 Hz, 1H); MS (ESI) m/z 491.18 (M+H).

Example 10

Synthesis of Compound 129

Scheme 10

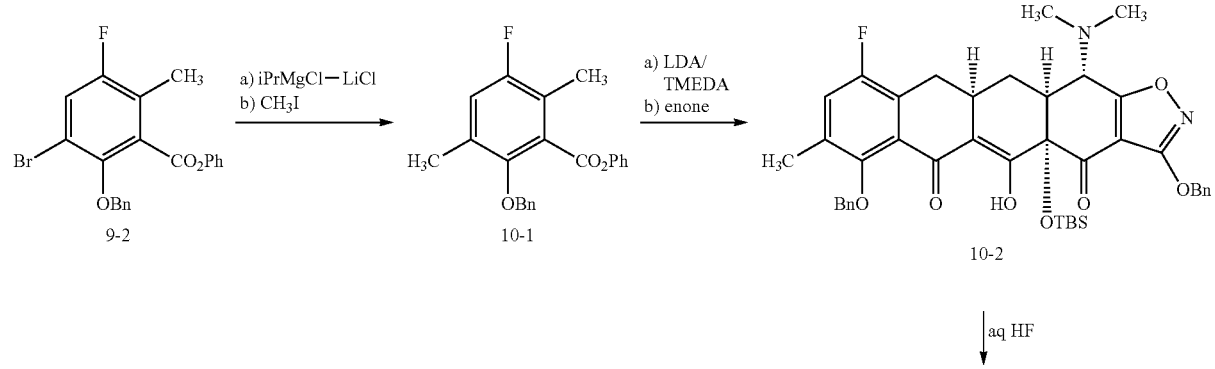

-continued

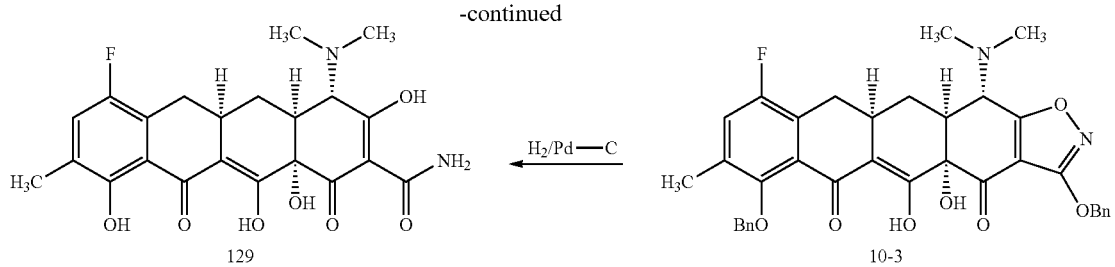

The following compounds were prepared according to Scheme 10.

Compound 10-1

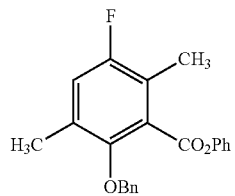

iPrMgCl.LiCl (0.68 mL, 1.2 M, 0.82 mmol, 2 equiv) was added to a THF solution (5 mL) of 9-2 (170 mg, 0.41 mmol) at 0° C. The reaction was stirred at 0° C. for 30 min. MeI (0.2 mL, 1.64 mmol, 4 equiv) was added to the reaction mixture. The reaction was stirred at 0° C. for 30 min and allowed to warm to 25° C. over 1 h. The reaction was quenched with NH$_4$Cl solution and extracted with EtOAc. The combined EtOAc extracts were dried (Na$_2$SO$_4$) and concentrated to give crude 10-1. Flash chromatography on silica gel (30:1 hexanes/EtOAc) yielded 31 mg of compound 10-1 (22%).

Compound 10-2

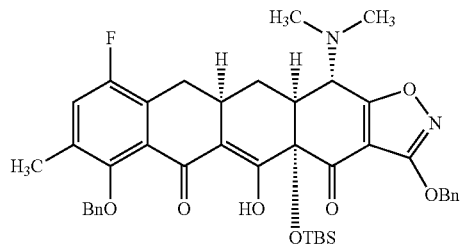

A THF solution (1 mL) of 10-1 (31 mg, 0.088 mmol, 1.7 equiv) was add to a THF solution (1 mL) of LDA (0.13 mL, 1.3 M, 0.176 mmol, 3.3 equiv) and TMEDA (39 μL, 0.26 mmol, 4.9 equiv). The reaction was stirred at −78° C. for 10 min. A THF solution (1 mL) of enone (26 mg, 0.053 mmol) was added to the reaction at −78° C. The reaction was stirred at −78° C. for 30 min and allowed to warm to 25° C. over 1 h, quenched with saturated NH$_4$Cl solution, and extracted with EtOAc. The combined EtOAc extracts were dried (Na$_2$SO$_4$) and concentrated to yield the crude 10-2. Preparative reverse phase HPLC purification on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 4.0 mL (CH$_3$CN); gradient: 80→100% B over 15 min; mass-directed fraction collection]. Fractions with the desired MW were collected and concentrated on a RotaVap at 25° C. to remove most of the acetonitrile. The resulting mostly aqueous solution was extracted with EtOAc. The combined EtOAc extracts were dried (Na$_2$SO$_4$) and concentrated to give 10 mg of 10-2 (26%).

Compound 10-3

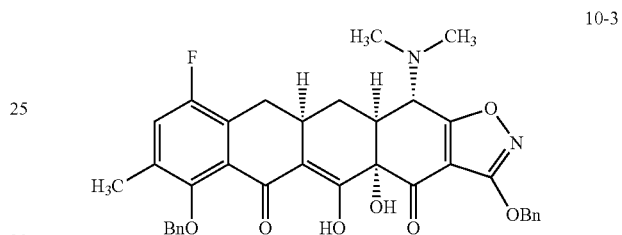

Aqueous HF (0.3 mL, 48%) was added to a CH$_3$CN solution (2 mL) of 10-2 (6 mg, 0.008 mmol) in a polypropylene tube at 25° C. The reaction was stirred at 25° C. for 18 h. The resulting mixture was poured into an aqueous solution of K$_2$HPO$_4$ (2 g, dissolved in 15 mL water). The mixture was extracted with EtOAc. The combined EtOAc extracts were dried (Na$_2$SO$_4$) and concentrated to yield crude 10-3.

Compound 129

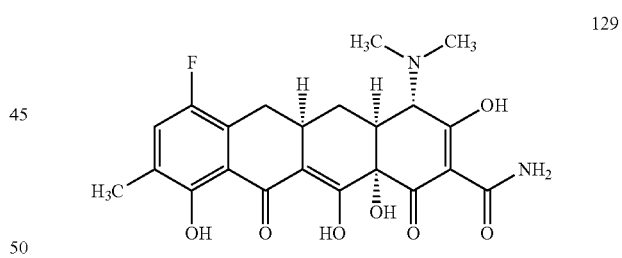

Palladium on carbon (2 mg, 10 wt %) was added to a HCl/MeOH solution (0.5N, 2 mL) of the crude 10-3. The reaction was purged with hydrogen and stirred under H$_2$ (balloon) at 25° C. for 4 h. The reaction mixture was filtered through a small Celite plug. The filtrate was concentrated to yield the crude product. Preparative reverse phase HPLC purification on a Waters Autopurification system using a Phenomenex Polymerx 10μ, RP-1 100A column [10 μm, 150× 21.20 mm; flow rate, 20 mL/min; Solvent A: 0.05 N HCl/water; Solvent B: CH$_3$CN; injection volume: 4.0 mL (0.05 N HCl/water); gradient: 0→70% B over 7 min, 70→100% over 3 min, and 100% over 5 min; mass-directed fraction collection]. Fractions with the desired MW were collected and freeze-dried to yield 1.5 mg of compound 129: $^1$H NMR (400 MHz, CD$_3$OD) δ 7.19 (d, J=9.7 Hz, 1H), 4.07 (s, 1H), 3.20-2.93 (m, 3H), 3.03 (s, 3H), 2.96 (s, 3H), 2.31-2.17 (m, 2H), 2.22 (s, 3H), 1.69-1.58 (m, 1H); MS (ESI) m/z 447.23 (M+H).

Example 11
Synthesis of Compounds 130-132
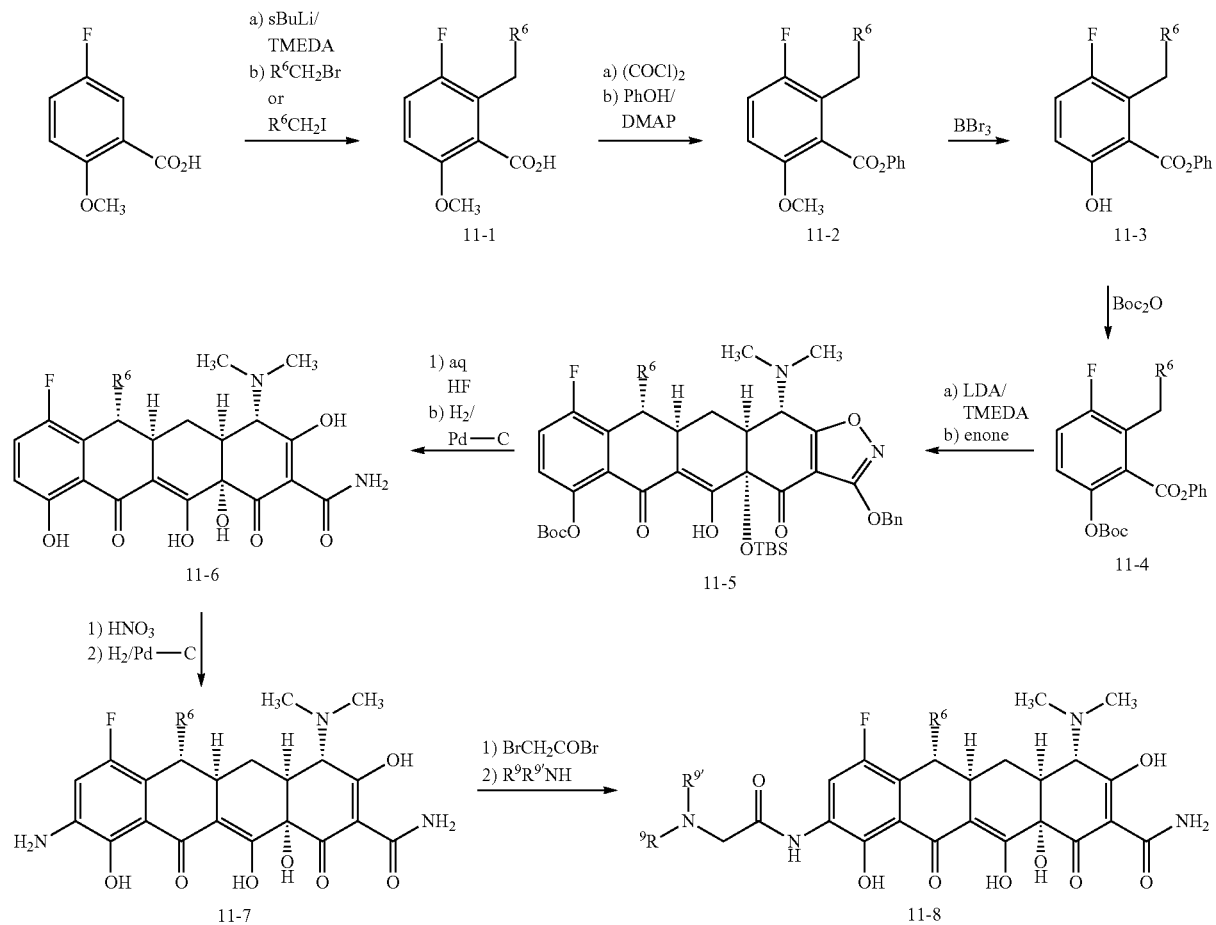
In Scheme 11, $R^6$, $R^9$, and $R^{9'}$ is X, $R^B$, and $R^A$, respectively, as defined in Structural Formula (A).
Compounds 130-132 were prepared according to Scheme 11.
Compound 130
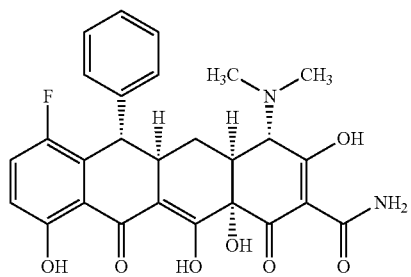
-continued
Compound 131
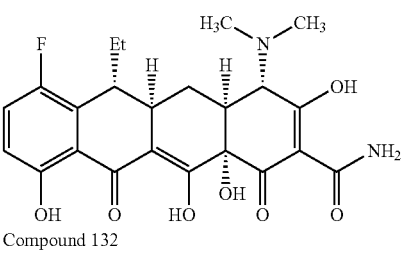
Compound 132
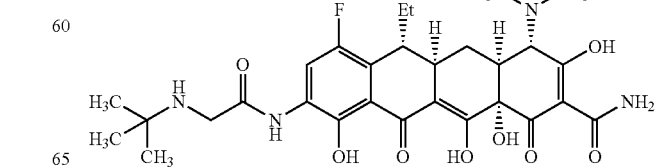

Example 12
Synthesis of Compounds 133-135
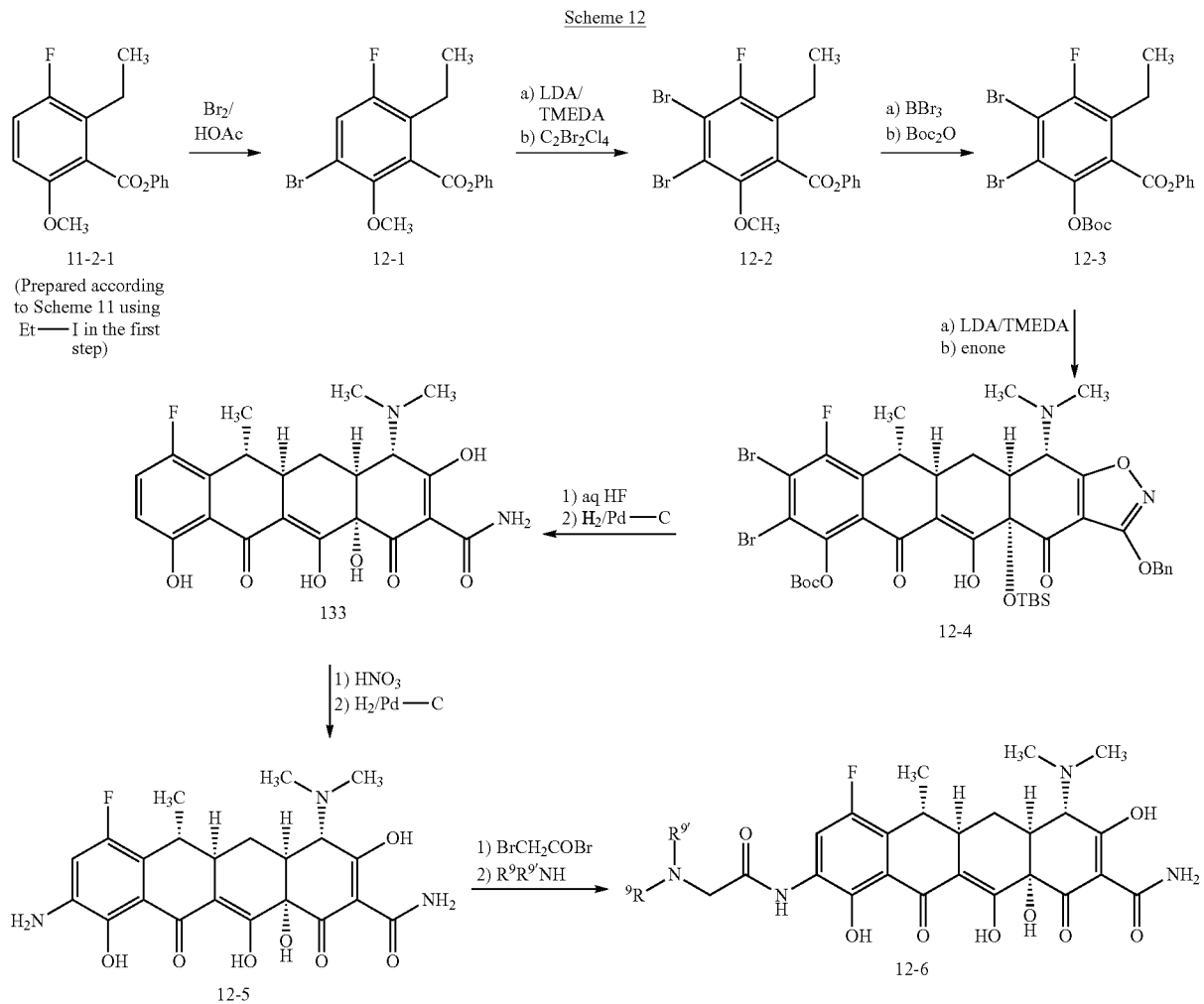
In Scheme 12, $R^9$ and $R^{9'}$ is $R^B$, and $R^A$, respectively, as defined in Structural Formula (A).
Compounds 133-135 were prepared according to Scheme 12.
Compound 133
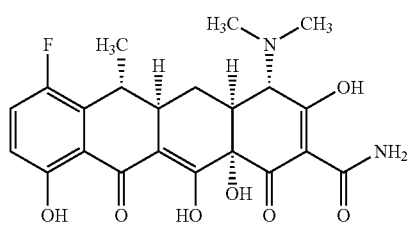
Compound 134
Compound 135
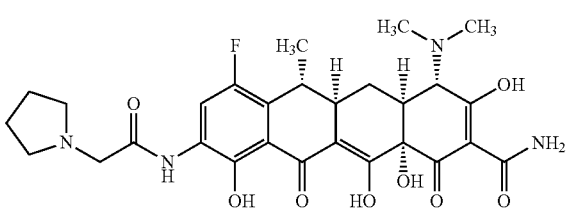

Example 13

The antibacterial activities for the compounds of the invention were studied according to the following protocols.

Minimum Inhibitory Concentration Assay

Frozen bacterial strains were thawed and subcultured onto Mueller Hinton Broth (MHB) or other appropriate media (Streptococcus requires blood and *Haemophilus* requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty μL of MHB was added to wells 2-12 of a 96-well plate. One hundred μL of appropriately diluted antibiotics was added to well 1. Fifty μL of antibiotics was removed from well 1 and added to well 2 and the contents of well 2 mixed by pipetting up and down five times. Fifty μL of the mixture in well 2 was removed and added to well 3 and mixed as above. Serial dilutions were continued in the same manner through well 12. Fifty μL was removed from well 12 so that all contained 50 μL. Fifty μL of the working inoculum was then added to all test wells. A growth control well was prepared by adding 50 μL of working inoculum and 50 μL of MHB to an empty well. The plates were then incubated at 37° C. overnight, removed from the incubator and each well was read on a plate reading mirror. The lowest concentration (MIC) of test compound that inhibited the growth of the bacteria was recorded.

Example:

|       | 1  | 2  | 3 | 4 | 5 | 6 | 7   | 8    | 9     | 10   | 11   | 12    |
|-------|----|----|---|---|---|---|-----|------|-------|------|------|-------|
| [Abt] | 32 | 16 | 8 | 4 | 2 | 1 | 0.5 | 0.25 | 0.125 | 0.06 | 0.03 | 0.015 |
| grow  | −  | −  | − | − | − | + | +   | +    | +     | +    | +    | +     |

[abt] = antibiotic concentration in the well
Grow = bacterial growth (cloudiness)
Interpretation: MIC = 2 μg/mL Protocol for Determining Inoculum Concentration (Viable Count)

Ninety μL of sterile 0.9% NaCl was pipetted into wells 2-6 of a 96-well microtiter plate. Fifty 50 μl of the inoculum was pipetted into well 1. Ten μL was removed from well 1 and added it to well 2 followed by mixing. Ten μL was removed from well two and mixed with the contents of well 3 and so on creating serial dilutions through well 6. Ten μL was removed from each well and spotted onto an appropriate agar plate. The plate was placed into a $CO_2$ incubator overnight. The colonies in spots that contain distinct colonies were counted. Viable count was calculated by multiplying the number of colonies by the dilution factor.

| Spot from Well  | 1      | 2      | 3      | 4      | 5      | 6      |
|-----------------|--------|--------|--------|--------|--------|--------|
| Dilution Factor | $10^2$ | $10^3$ | $10^4$ | $10^5$ | $10^6$ | $10^7$ |

Bacterial Strains

Fifteen bacterial strains, listed below, were examined in minimum inhibitory concentration (MIC) assays.

| ID    | Organism      | Source       | Resistance                                              | Comments                    | Gram Rx  |
|-------|---------------|--------------|---------------------------------------------------------|-----------------------------|----------|
| SA100 | S. aureus     | ATCC 13709   | MSSA                                                    | Smith strain (animal model) | positive |
| SA101 | S. aureus     | ATCC 29213   | MSSA                                                    | control                     | positive |
| SA158 | S. aureus     | M R, SK75    | tet resistant: tetK (efflux)                            |                             | positive |
| SA161 | S. aureus     | Micromyx, LLC| tet resistant: tet(M) ribosomal protection              |                             | positive |
| EF103 | E. faecalis   | ATCC 29212   | tet intermediate/ resistant - mechanism not specified   | control                     | positive |
| EF159 | E. faecalis   | M R, DS160   | tet resistant: tetM rib protect)                        | cip-R, ery-I                | positive |
| SP106 | S. pneumoniae | ATCC 49619   | wt                                                      | control                     | positive |

-continued

| ID | Organism | Source | Resistance | Comments | Gram Rx |
|---|---|---|---|---|---|
| SP160 | S. pneumoniae | M R, 54 | tet resistant: tet M (rib protect) | pen-R, ery-R | positive |
| EC107 | E. coli | ATCC 25922 | wt | control | negative |
| EC155 | E. coli | M R, 10 | tet resistant: tetA (efflux) | | negative |
| KP109 | K. pneumoniae | ATCC 13883 | wt | | negative |
| KP153 | K. pneumoniae | M R, 1 | tet resistant: tetA (efflux) | cip-R, gen-R | negative |
| EC108 | E. cloacae | ATCC 13047 | wt | | negative |
| AB110 | A. baumanii | ATCC 19606 | wt | | negative |
| PA111 | P. aeruginosa | ATCC 27853 | wt | control | negative |

MSSA = methicillin susceptible *S. aureus*
wt = wild type
ATCC = American Type Culture Collection
M R = Marilyn Roberts, University of Washington
tet = tetracycline
cip = ciprofloxacin
R = resistant
gen = gentamicin
ery = erythromycin
pen = penicillin Results Values of minimum inhibition concentration (MIC) for the compounds of the invention are provided in Tables 1a, 1b, 2a, 2b and 3.

TABLE 1a

| Compound ID | MICs (ug/mL) | | | | | | | |
|---|---|---|---|---|---|---|---|---|
| | SA101 | SA100 | SA161 | SA158 | EF103 | EF159 | SP106 | SP160 |
| 11 | 0.125 | 0.25 | 0.25 | 0.0625 | 0.0625 | 0.125 | ≦0.0156 | ≦0.0156 |
| 12 | ≦0.0156 | ≦0.0156 | 0.125 | 0.5 | ≦0.0156 | 0.0625 | ≦0.0156 | ≦0.0156 |
| 13 | ≦0.0156 | ≦0.0156 | 0.0625 | 0.25 | ≦0.0156 | 0.0625 | ≦0.0156 | ≦0.0156 |
| 14 | 0.5 | 0.25 | 0.5 | 0.25 | 0.125 | 0.25 | 0.03 | 0.125 |
| 15 | 0.5 | 0.5 | 0.5 | 0.25 | 0.5 | 0.5 | 0.016 | 0.016 |
| 16 | 0.125 | 0.25 | 0.25 | 0.5 | 0.0625 | 0.0625 | ≦0.0156 | ≦0.0156 |
| 17 | 0.25 | 0.5 | 1 | 2 | 0.25 | 1 | 0.0625 | 0.0625 |
| 18 | 0.0625 | ≦0.0156 | 0.0625 | 0.125 | ≦0.0156 | 0.0313 | ≦0.0156 | ≦0.0156 |
| 19 | 0.125 | 0.25 | 0.25 | 0.25 | ≦0.0156 | 0.125 | ≦0.0156 | ≦0.0156 |
| 20 | ≦0.0156 | 0.25 | 0.25 | 0.5 | ≦0.0156 | 0.0625 | ≦0.0156 | ≦0.0156 |
| 21 | 0.25 | 0.25 | 0.5 | 4 | 0.125 | 1 | ≦0.0156 | 0.0625 |
| 22 | 1 | 1 | 2 | 4 | 2 | 4 | 0.5 | 1 |
| 23 | ≦0.0156 | 0.5 | 0.125 | 0.25 | ≦0.0156 | 0.0313 | ≦0.0156 | ≦0.0156 |
| 24 | 0.25 | 0.25 | 0.125 | 0.125 | ≦0.0156 | ≦0.0156 | ≦0.0156 | ≦0.0156 |
| 25 | 0.125 | 0.125 | 0.125 | 0.0313 | ≦0.0156 | 0.0625 | ≦0.0156 | ≦0.0156 |
| 26 | 1 | 1 | 1 | 1 | 0.25 | 0.5 | ≦0.0156 | ≦0.0156 |
| 27 | 2 | 2 | 4 | 16 | 2 | 4 | 0.125 | 0.5 |
| 28 | 1 | 2 | 2 | 1 | 1 | 1 | 0.125 | 0.0625 |
| 29 | 4 | 4 | 4 | 2 | 2 | 2 | 1 | 1 |
| 30 | 2 | 1 | 4 | 2 | 2 | 2 | 2 | 4 |
| 31 | 1 | 2 | 2 | 1 | 0.5 | 1 | 0.25 | 0.25 |

TABLE 1b

| Compound ID | MICs (ug/mL) | | | | | | |
|---|---|---|---|---|---|---|---|
| | EC107 | EC155 | AB110 | PA111 | EC108 | KP109 | KP153 |
| 11 | 0.25 | 2 | 0.5 | 16 | 1 | 1 | 2 |
| 12 | 0.25 | 8 | 1 | 16 | 1 | 1 | 4 |
| 13 | 0.125 | 4 | 0.25 | 16 | 1 | 0.5 | 2 |
| 14 | 0.5 | 4 | 0.25 | 16 | 2 | 1 | 2 |
| 15 | 1 | 4 | 0.125 | 16 | 4 | 2 | 4 |
| 16 | 0.5 | 8 | 1 | 16 | 1 | 1 | 4 |
| 17 | 2 | 32 | 0.5 | 32 | 8 | 4 | 32 |
| 18 | 0.125 | 4 | 0.25 | 16 | 0.5 | 0.5 | 4 |
| 19 | 0.25 | 4 | 0.25 | 16 | 2 | 1 | 4 |
| 20 | 0.25 | 8 | 1 | 8 | 1 | 1 | 4 |
| 21 | 1 | 16 | 2 | 16 | 4 | 2 | 8 |
| 22 | 16 | >32 | 2 | >32 | >32 | 32 | >32 |

TABLE 1b-continued

| Compound ID | MICs (ug/mL) | | | | | | |
|---|---|---|---|---|---|---|---|
| | EC107 | EC155 | AB110 | PA111 | EC108 | KP109 | KP153 |
| 23 | 0.125 | 8 | 0.125 | 8 | 1 | 0.5 | 8 |
| 24 | 0.5 | 8 | 0.0313 | 16 | 2 | 1 | 8 |
| 25 | 0.5 | 8 | 0.125 | 32 | 2 | 2 | 8 |
| 26 | 0.5 | 4 | 0.25 | 16 | 2 | 2 | 4 |
| 27 | 4 | 32 | 16 | >32 | 16 | 8 | 32 |
| 28 | 2 | 16 | 0.5 | >32 | 8 | 4 | 16 |
| 29 | 8 | 8 | 8 | >32 | 8 | 8 | 8 |
| 30 | >32 | >32 | 8 | >32 | >32 | >32 | >32 |
| 31 | 2 | 8 | 0.5 | >32 | 8 | 4 | 8 |

TABLE 2a

| Compound ID | MICs (ug/mL) | | | | | | | |
|---|---|---|---|---|---|---|---|---|
| | SA101 | SA100 | SA161 | SA158 | EF103 | EF159 | SP106 | SP160 |
| 32 | 0.125 | 0.5 | 0.25 | 0.5 | 0.0625 | 0.125 | ≦0.0156 | ≦0.0156 |
| 33 | 0.25 | 0.5 | 1 | 2 | 0.25 | 1 | ≦0.0156 | 0.125 |
| 34 | ≦0.0156 | 0.0625 | 0.0625 | 0.125 | ≦0.0156 | ≦0.0156 | ≦0.0156 | ≦0.0156 |
| 35 | 0.25 | 0.25 | 0.5 | 0.5 | 0.125 | 0.25 | 0.016 | 0.016 |
| 36 | 0.25 | 0.5 | 0.5 | 1 | 0.25 | 0.25 | ≦0.0156 | ≦0.0156 |
| 37 | 8 | 8 | >32 | >32 | 16 | 16 | 2 | 4 |
| 38 | 8 | 8 | 16 | 32 | 8 | 16 | 2 | 8 |
| 39 | 2 | 2 | 2 | 16 | 2 | 2 | 0.25 | 0.5 |
| 40 | 1 | 1 | 1 | 16 | 1 | 1 | 0.0625 | 0.5 |
| 41 | 1 | 1 | 2 | 1 | 1 | 2 | 0.125 | 0.125 |
| 42 | 0.5 | 1 | 2 | 1 | 0.5 | 1 | 0.125 | 0.0625 |
| 43 | 0.5 | 0.5 | 1 | 0.5 | 0.25 | 0.5 | ≦0.0156 | ≦0.0156 |
| 44 | 4 | 4 | 8 | 8 | 8 | 8 | 0.5 | 1 |
| 45 | 0.5 | 0.5 | 1 | 0.5 | 0.25 | 0.5 | 0.125 | 0.06 |
| 46 | 0.25 | 0.25 | 0.5 | 0.25 | 0.25 | 0.5 | 0.125 | 0.125 |

TABLE 2b

| Compound ID | MICs (ug/mL) | | | | | | |
|---|---|---|---|---|---|---|---|
| | EC107 | EC155 | AB110 | PA111 | EC108 | KP109 | KP153 |
| 32 | 0.25 | 8 | 2 | 8 | 1 | 1 | 4 |
| 33 | 2 | >32 | 4 | >32 | 16 | 4 | >32 |
| 34 | 0.25 | 2 | 0.125 | 16 | 1 | 0.5 | 2 |
| 35 | 1 | 16 | 0.25 | >32 | 8 | 4 | 8 |
| 36 | 2 | 32 | 0.125 | >32 | 4 | 4 | 32 |
| 37 | >32 | >32 | >32 | >32 | >32 | >32 | >32 |
| 38 | >32 | >32 | >32 | >32 | >32 | >32 | >32 |
| 39 | 4 | >32 | 32 | >32 | 16 | 16 | >32 |
| 40 | 4 | >32 | 8 | 32 | 4 | 8 | 32 |
| 41 | 4 | 16 | 0.5 | >32 | 16 | 8 | 16 |
| 42 | 4 | 16 | 0.5 | >32 | 16 | 8 | 16 |
| 43 | 1 | 4 | 0.125 | 32 | 4 | 2 | 4 |
| 44 | 32 | >32 | 8 | >32 | >32 | >32 | >32 |
| 45 | 1 | 2 | 0.06 | >32 | 4 | 2 | 4 |
| 46 | 2 | 4 | 0.125 | >32 | 32 | 4 | 32 |

TABLE 3

MIC Values for Compounds of the Invention Compared to Sancycline, Minocycline and Tigecycline.

| Cmpd | SA101 29213 | SA100 13709 | SA161 MRSA, tetM | SA158 tetK | EF103 29212 | EF159 tetM | SP106 49619 | SP160 tetM |
|---|---|---|---|---|---|---|---|---|
| 11 | B | B | B | B | B | B | A | A |
| 12 | A | A | A | B | A | B | A | A |
| 13 | A | A | A | B | A | B | A | A |
| 14 | B | B | B | B | B | B | B | B |
| 15 | B | B | B | B | B | B | A | A |
| 16 | B | B | B | B | B | B | A | A |

TABLE 3-continued

MIC Values for Compounds of the Invention Compared to Sancycline, Minocycline and Tigecycline.

| | | | | | | | | |
|---|---|---|---|---|---|---|---|---|
| 17 | B | B | B | B | B | B | B | B |
| 18 | B | A | A | B | A | A | A | A |
| 19 | B | B | B | B | A | B | A | A |
| 20 | A | B | B | B | A | B | A | A |
| 21 | B | B | B | B | B | B | A | B |
| 22 | C | B | B | B | B | B | C | B |
| 23 | A | B | A | B | A | A | A | A |
| 24 | B | B | A | B | A | A | A | A |
| 25 | B | B | A | B | A | B | A | A |
| 26 | C | B | B | B | B | B | A | A |
| 27 | C | C | B | C | B | B | B | B |
| 28 | C | C | B | B | B | B | B | B |
| 29 | C | C | B | B | B | B | C | B |
| 30 | C | B | B | B | B | B | C | B |
| 31 | C | C | B | B | B | B | B | B |
| 32 | B | B | B | B | B | B | A | A |
| 33 | B | B | B | B | B | B | A | B |
| 34 | A | B | A | B | A | A | A | A |
| 35 | B | B | B | B | B | B | A | A |
| 36 | B | B | B | B | B | B | A | A |
| 37 | C | C | C | C | C | B | C | B |
| 38 | C | C | C | C | B | B | C | B |
| 39 | C | C | B | C | B | B | B | B |
| 40 | C | B | B | C | B | B | B | B |
| 41 | C | B | B | B | B | B | B | B |
| 42 | B | B | B | B | B | B | B | B |
| 43 | B | B | B | B | B | B | A | A |
| 44 | C | C | B | C | B | B | C | B |
| 45 | B | B | B | B | B | B | B | B |
| 46 | B | B | B | B | B | B | B | B |
| 47 | B | B | B | B | B | B | A | A |
| 48 | B | B | B | B | A | B | A | A |
| 49 | B | B | B | B | B | B | A | B |
| 50 | B | B | B | B | B | B | B | B |
| 51 | A | A | B | B | A | A | A | A |
| 52 | B | B | B | B | B | B | A | A |
| 53 | C | C | C | C | B | C | B | B |
| 54 | B | B | B | B | B | B | C | B |
| 55 | B | B | B | B | B | B | A | B |
| 56 | B | B | B | B | B | B | B | B |
| 57 | B | B | B | B | B | B | C | B |
| 58 | C | B | B | B | B | B | C | B |
| 59 | B | B | B | B | B | B | B | B |
| 60 | B | B | B | B | B | B | B | B |
| 61 | C | C | C | C | B | B | B | B |
| 62 | C | B | B | C | B | B | B | B |
| 63 | B | B | B | C | B | B | A | B |
| 64 | B | B | B | B | B | B | A | A |
| 65 | C | C | B | B | B | B | B | B |
| 66 | B | B | B | B | B | B | A | A |
| 67 | C | C | B | B | B | B | B | B |
| 68 | B | B | B | B | B | B | B | B |
| 69 | C | C | B | B | B | B | C | B |
| 70 | C | C | B | B | B | B | B | B |
| 71 | B | B | B | B | B | B | B | B |
| 72 | B | B | B | B | B | B | A | A |
| 73 | C | B | B | B | B | B | C | B |
| 74 | C | C | C | C | C | B | C | B |
| 75 | B | B | B | C | B | B | B | B |
| 76 | B | B | B | B | B | B | C | C |
| 77 | B | B | B | B | B | B | C | C |
| 78 | B | B | B | B | B | B | C | C |
| 79 | B | B | B | B | B | B | C | C |
| 80 | C | C | B | C | B | B | C | B |
| 81 | B | B | A | B | B | B | C | C |
| 82 | B | B | A | B | B | B | C | B |
| 83 | B | B | A | B | B | B | C | C |
| 84 | B | B | B | B | B | B | B | B |
| 85 | B | B | B | B | B | B | A | B |
| 86 | B | B | B | B | B | B | B | B |
| 87 | C | B | B | B | B | B | C | C |
| 88 | B | B | A | B | B | B | A | B |
| 89 | A | A | A | A | A | A | A | A |
| 90 | B | B | A | B | B | B | C | B |
| 91 | B | B | B | B | B | B | C | B |
| 92 | B | B | B | B | B | B | C | B |
| 93 | B | B | B | B | B | B | C | B |

TABLE 3-continued

MIC Values for Compounds of the Invention Compared to Sancycline, Minocycline and Tigecycline.

| | | | | | | | | |
|---|---|---|---|---|---|---|---|---|
| 94 | B | B | A | B | B | B | C | B |
| 95 | B | B | B | B | B | B | C | B |
| 96 | B | B | B | B | B | B | C | B |
| 97 | B | B | B | B | B | B | C | C |
| 98 | B | B | B | B | B | B | C | B |
| 99 | C | B | B | B | B | B | C | C |
| 100 | B | B | B | B | B | B | C | C |
| 101 | B | B | B | B | B | B | B | B |
| 102 | C | B | B | B | B | B | B | B |
| 103 | C | C | C | C | B | C | C | B |
| 104 | B | B | B | B | B | B | B | B |
| 105 | C | B | B | C | B | B | B | B |
| 106 | C | B | B | B | B | B | C | B |
| 107 | NT | NT | NT | NT | NT | NT | NT | NT |
| 108 | C | C | C | C | C | C | C | C |
| 109 | C | C | C | C | C | C | C | C |
| 110 | C | C | C | C | C | C | C | C |
| 111 | C | C | C | C | C | C | C | C |
| 112 | C | C | C | C | C | C | C | C |
| 113 | C | C | C | C | B | C | B | B |
| 114 | C | C | B | B | B | B | B | B |
| 115 | C | C | B | B | B | B | C | B |
| 116 | C | C | C | B | B | B | B | B |
| 117 | C | C | C | B | B | B | B | B |
| 118 | C | C | B | B | B | B | B | B |
| 119 | C | C | B | B | B | B | C | B |
| 120 | C | C | C | C | C | C | C | C |
| 121 | C | C | C | C | B | C | C | B |
| 122 | C | C | C | C | C | C | C | B |
| 123 | C | C | C | C | C | C | C | C |
| 124 | C | C | C | C | B | C | C | B |
| 125 | C | C | C | B | B | B | C | B |
| 126 | C | C | C | C | C | C | C | C |
| 127 | C | B | B | B | B | B | C | B |
| 128 | C | C | B | C | B | B | C | C |
| 129 | C | B | B | B | B | B | C | B |
| 131 | C | C | B | B | C | B | C | C |
| 132 | C | C | C | B | B | B | C | B |
| 133 | B | B | B | B | B | B | B | B |
| 130 | C | B | B | B | B | B | C | B |
| 134 | B | B | B | B | B | B | A | A |
| 135 | B | B | B | B | B | B | A | A |
| Minocycline | 0.06 | 0.06 | 8 | 0.03 | 1 | 16 | 0.016 | 2 |
| Sancycline | 0.5 | 1 | | 4 | 8 | 8 | 0.25 | 8 |
| Tigecycline | 0.06 | 0.06 | 0.125 | 0.06 | 0.03 | 0.06 | 0.016 | 0.016 |

| Cmpd | EC107 25922 | EC155 tetA | AB110 19606 | PA111 27853 | EC108 13047 | KP109 13883 | KP153 tetA |
|---|---|---|---|---|---|---|---|
| 11 | B | B | C | B | B | B | B |
| 12 | B | B | C | B | B | B | B |
| 13 | B | B | B | B | B | B | B |
| 14 | B | B | B | B | B | B | B |
| 15 | B | B | B | B | B | B | B |
| 16 | B | B | C | B | B | B | B |
| 17 | B | B | C | C | B | B | B |
| 18 | B | B | B | B | B | B | B |
| 19 | B | B | B | B | B | B | B |
| 20 | B | B | C | A | B | B | B |
| 21 | B | B | C | B | B | B | B |
| 22 | C | C | C | C | C | C | C |
| 23 | B | B | B | A | B | B | B |
| 24 | B | B | A | B | B | B | B |
| 25 | B | B | B | C | B | B | B |
| 26 | B | B | B | B | B | B | B |
| 27 | B | B | C | C | C | B | B |
| 28 | B | B | C | C | B | B | B |
| 29 | B | B | C | C | B | B | B |
| 30 | C | C | C | C | C | C | C |
| 31 | B | B | C | C | B | B | B |
| 32 | B | B | C | A | B | B | B |
| 33 | B | C | C | C | C | B | C |
| 34 | B | B | B | B | B | B | B |
| 35 | B | B | B | C | B | B | B |
| 36 | B | B | B | C | B | B | B |
| 37 | C | C | C | C | C | C | C |
| 38 | C | C | C | C | C | C | C |

TABLE 3-continued

MIC Values for Compounds of the Invention Compared to Sancycline, Minocycline and Tigecycline.

| | | | | | | | |
|---|---|---|---|---|---|---|---|
| 39 | B | C | C | C | C | C | C |
| 40 | B | C | C | C | B | B | B |
| 41 | B | B | C | C | C | B | B |
| 42 | B | B | C | C | C | B | B |
| 43 | B | B | B | C | B | B | B |
| 44 | C | C | C | C | C | C | C |
| 45 | B | B | A | C | B | B | B |
| 46 | B | B | B | C | C | B | B |
| 47 | B | B | C | A | B | B | B |
| 48 | A | B | A | A | A | A | A |
| 49 | B | B | B | C | B | B | A |
| 50 | B | B | B | C | B | B | B |
| 51 | B | B | B | B | B | B | B |
| 52 | B | B | B | C | B | B | A |
| 53 | C | C | C | C | C | C | C |
| 54 | C | C | C | C | C | C | C |
| 55 | B | C | C | C | B | B | C |
| 56 | B | C | C | C | C | B | C |
| 57 | C | C | C | C | C | C | C |
| 58 | C | C | C | C | C | C | C |
| 59 | B | C | C | C | C | C | C |
| 60 | B | C | C | C | B | B | B |
| 61 | C | C | C | C | C | C | C |
| 62 | C | C | C | C | C | C | C |
| 63 | B | C | C | C | B | B | C |
| 64 | B | B | C | B | B | B | B |
| 65 | B | B | C | C | B | B | B |
| 66 | B | B | B | C | B | B | B |
| 67 | B | B | C | C | B | B | B |
| 68 | B | B | C | B | B | B | B |
| 69 | B | C | C | C | B | C | B |
| 70 | B | C | C | C | B | B | C |
| 71 | B | C | C | C | C | B | C |
| 72 | B | C | C | C | C | C | C |
| 73 | C | C | C | C | C | C | C |
| 74 | C | C | C | C | C | C | C |
| 75 | B | C | C | C | B | B | C |
| 76 | C | C | C | C | C | C | C |
| 77 | C | C | C | C | C | C | C |
| 78 | C | C | C | C | C | C | C |
| 79 | C | C | C | C | C | C | C |
| 80 | C | C | C | C | C | C | C |
| 81 | C | C | C | C | C | C | C |
| 82 | C | C | C | C | C | C | C |
| 83 | C | C | C | C | C | C | C |
| 84 | C | C | C | C | C | C | C |
| 85 | B | C | C | C | B | B | C |
| 86 | C | C | C | C | C | C | C |
| 87 | C | C | C | C | C | C | C |
| 88 | B | B | C | A | B | B | B |
| 89 | A | B | A | A | A | A | A |
| 90 | C | C | C | C | C | C | C |
| 91 | C | C | C | C | C | C | C |
| 92 | C | C | C | C | C | C | C |
| 93 | C | C | C | C | C | C | C |
| 94 | C | C | C | C | C | C | C |
| 95 | C | C | C | C | C | C | C |
| 96 | C | C | C | C | C | C | C |
| 97 | C | C | C | C | C | C | C |
| 98 | C | C | C | C | C | C | C |
| 99 | C | C | C | C | C | C | C |
| 100 | C | C | C | C | C | C | C |
| 101 | B | B | C | C | B | B | C |
| 102 | B | B | C | C | B | B | B |
| 103 | B | C | C | C | B | C | C |
| 104 | B | C | C | C | B | B | C |
| 105 | B | C | C | C | C | C | C |
| 106 | C | C | C | C | C | C | C |
| 107 | NT | NT | NT | NT | NT | NT | NT |
| 108 | C | C | C | C | C | C | C |
| 109 | C | C | C | C | C | C | C |
| 110 | C | C | C | C | C | C | C |
| 111 | C | C | C | C | C | C | C |
| 112 | C | C | C | C | C | C | C |
| 113 | B | C | C | C | B | B | C |
| 114 | B | B | C | C | B | B | B |
| 115 | B | B | C | C | C | B | B |

TABLE 3-continued

MIC Values for Compounds of the Invention Compared to Sancycline, Minocycline and Tigecycline.

| | | | | | | | |
|---|---|---|---|---|---|---|---|
| 116 | B | C | C | C | B | B | B |
| 117 | B | C | C | C | B | B | C |
| 118 | B | C | C | C | B | B | B |
| 119 | C | B | C | C | C | C | B |
| 120 | C | C | C | C | C | C | C |
| 121 | C | C | C | C | C | C | C |
| 122 | C | C | C | C | C | C | C |
| 123 | C | C | C | C | C | C | C |
| 124 | C | C | C | C | C | C | C |
| 125 | C | C | C | C | C | C | C |
| 126 | C | C | C | C | C | C | C |
| 127 | C | C | C | C | C | C | C |
| 128 | C | C | C | C | C | C | C |
| 129 | C | C | C | C | C | C | B |
| 131 | C | B | C | C | C | C | B |
| 132 | C | B | C | C | C | C | B |
| 133 | B | B | C | C | C | B | B |
| 130 | C | C | C | C | C | C | C |
| 134 | B | B | C | C | B | B | B |
| 135 | B | B | C | C | B | B | B |
| Minocycline | 0.5 | 8 | 0.06 | 16 | 2 | 1 | 8 |
| Sancycline | 8 | 32 | 0.25 | >32 | 8 | 8 | 32 |
| Tigecycline | 0.03 | 0.5 | 0.25 | 8 | 0.25 | 0.125 | 1 |

A = lower than or equal to lowest MIC among three control compounds; B = greater than lowest MIC among three control compounds, but lower than highest MIC among three control compounds; C = greater than MIC of all three control compounds. The lowest concentration limit of the assay is 0.016. Thus, reported values in the assay of 0.016 represent an MIC of 0.016 or lower.

$ED_{50}$ IV Study

Compounds of the present invention were evaluated for efficacy in a mouse systemic infection model against a susceptible S. aureus isolate, ATCC 13709. Mice were infected via intraperitoneal injection with a bacterial load that would result in 0% survival within 48 hours after infection. Mice received the test compounds 60 minutes post infection via intravenous injection. Infection control groups did not receive treatment. Survival was assessed over a 48 hour period. Percent survival was calculated and $PD_{50}$ values determined using Probit analysis.

Tet-R Sepsis Study

The protocol for tetracycline-resistance sepsis study was similar to the protocol for $EV_{50}$ IV study described above except the infection model used S. aureus SA161, a tetracycline-resistant strain.

GN Sepsis

The protocol for GN sepsis study was similar to the protocol for $EV_{50}$ IV study described above except the infection model used E. coli ATCC 25922.

Metabolic Stability

A stock solution of the test compounds were prepared by dissolving the compound in DMSO to a final concentration of 1.0 mg/mL.

The analytes and internal standard were diluted and infused into the LC/MS system to determine optimal ionization, polarity and MS/MS fragmentation for selection of specific MRM (multiple reaction monitoring) transitions. Generic chromatographic conditions were developed with a less than 5 minute cycle time.

Pooled human microsome assays were conducted at 0.2 mg/mL protein with an NADPH generating cofactor system (1.3 mM NADP+, 3.3 mM glucose-6-phosphate, 0.4 U/mL glucose-6-phosphate dehydrogenase, and 3.3 mM magnesium chloride).

Test compounds were diluted from DMSO stocks to 1 µM reaction concentrations. Time points were removed at 0 and 60 minutes. After a protein crash with acetonitrile, samples are analyzed by LC/MS/MS. Peak areas are compared to the time 0 sample, and the percent analyte remaining is calculated. A reaction containing no cofactor was used to control for analyte loss due to non-specific binding, thermal degradation and solubility.

SA MIC90

Twenty randomly selected clinical isolates of S. aureus were used to determine the minimal inhibitory concentration (MIC) of test compounds for 90% of the isolates ($MIC_{90}$). MICs were performed by microtiter broth dilution in a 96-well format according to Clinical Laboratory Standards Institute (CLSI) guidelines, as described above.

Viable counts were determined by 10-fold serial dilution. Dilutions were prepared in sterile 0.9% NaCl. Ten microliters of the inoculum and of each of 5 dilutions were plated onto blood or Mueller Hinton agar plates, incubated overnight at 37° C. with 5% $CO_2$, and counted.

TetR MIC90

Ten isolates selected based on resistance to tetracycline were used to determine the $MIC_{90}$ as described above.

EC MIC90

Twenty randomly selected clinical isolates of E. coli were used to determine the $MIC_{90}$ as described above.

Protein Binding

Test compounds were prepared as 1.0 mg/mL stock solutions in DMSO. The analytes and internal standard were diluted and infused into the LC/MS system to determine optimal ionization, polarity and MS/MS fragmentation for selection of specific MRM (multiple reaction monitoring) transitions. Generic chromatographic conditions were developed with a less than 5 minute cycle time.

The DMSO stocks were diluted to 1 and 10 µg/mL in human plasma and incubated in RED devices for 4 hours at 37° C. The time point was removed at the end of the incubation period. After a protein crash with acetonitrile, the samples were analyzed by LC/MS/MS. Peak areas for the buffer (receiver) and sample (donor) chambers were compared and the protein bound fraction is calculated. Analysis was conducted in duplicate.

Thigh Burden

Female CD-1 mice were pre-treated with cyclophosphamide to render the mice neutropenic. Mice were infected with *S. aureus* ATCC 13709 via injection into the right thigh muscle of 0.1 ml per mouse. One and a half hours post infection mice were treated IV with test compounds in doses ranging from 0.3 to 30 mg/kg or 0.3 to 20 mg/kg. Four mice were treated with each drug concentration. Twenty-four hours post treatment, mice were euthanized by $CO_2$ inhalation. The right thighs of the mice were aseptically removed, weighed, homogenized, serially diluted, and plated on TSA medium. The plates were incubated overnight at 37° C. in 5% $CO_2$. Colony forming units per gram of thigh was calculated by enumerating the plated colonies then adjusting for serial dilutions and the weight of the thigh.

The results for the biological activity studies described above are listed in Table 4. Table 4.

| | ED50 IV | Meta Stab % | SA MIC90 | TetR MIC90 | EC MIC90 | Prot Bind % | TetR sepsis | GN sepsis | Thigh Burden |
|---|---|---|---|---|---|---|---|---|---|
| 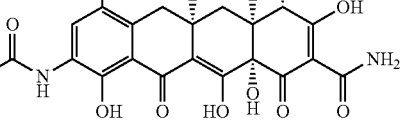 | 0.3 | 104% | 0.03 | 2 | 0.5 | 90 | 0.4 | 6.2 | 4.41 log10 decrease |
| 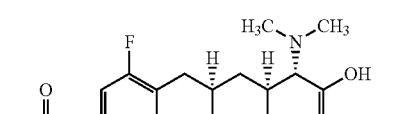 | 0.55 | 72% | 0.03 | 4 | 1 | 95.6 | 3.5 | 14.3 | 5.01 log10 decrease |
| 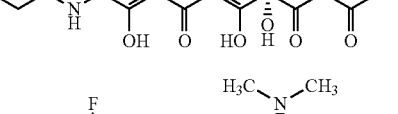 | 0.07 | 85% | 0.03 | 4 | 0.5 | 87.1 | | | |
| 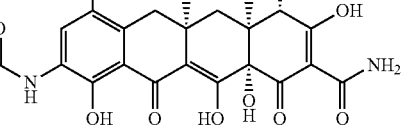 | 0.3 | 86% | 0.03 | 2 | 0.5 | 79.4 | 1 | 4.36 | 5.24 log10 decrease |
| 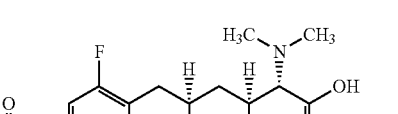 | 0.55 | 65% | 0.03 | 8 | 2 | 87.9 | | | |
| 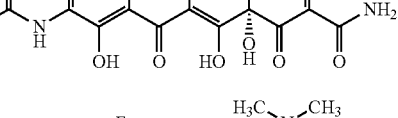 | 0.3 | 96% | 0.06 | 2 | 1 | 96.9 | | | |
| 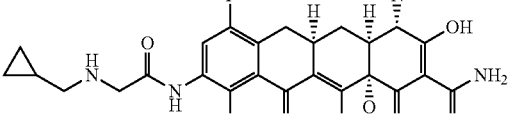 | 0.073 | 109% | 0.06 | 4 | 4 | 93.6 | 0.62 | 4.3 | 4.12 log10 decrease |

| | ED50 IV | Meta Stab % | SA MIC90 | TetR MIC90 | EC MIC90 | Prot Bind % | TetR sepsis | GN sepsis | Thigh Burden |
|---|---|---|---|---|---|---|---|---|---|
| 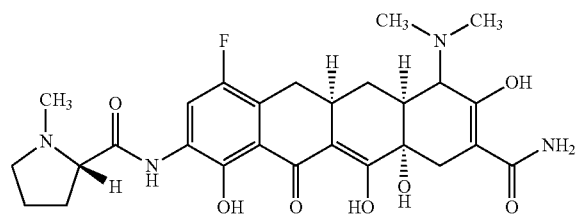 [SMILES: CN(C)C1C(O)=C(C(N)=O)C[C@@]2(O)C(O)=C3C(=O)c4c(O)c(NC(=O)[C@@H]5CCCN5C)cc(F)c4C[C@H]3C[C@@H]12] | 0.97 | 55% | 0.06 | 1 | 0.5 | 69.1 | 0.55 | 2.1 | 4.89 log10 decrease |

$ED_{50}$: mg/kg required to protect 50% of mice in septicemia model with *S. aureus* Smith strain.
Meta Stab %: % compound remaining after 60 min, 37° C. incubation with human liver microsomes.
SA MIC90: concentration (ug/mL) required to inhibit 90% of *S. aureus* clinical isolates (n = 20).
TetR MIC90: concentration (ug/mL) required to inhibit 90% of tetracycline-resistant *S. aureus* (n = 10).
EC MIC90: concentration (ug/mL) required to inhibit 90% of *E. coli* clinical isolates (n = 20).
Prot Bind: % Protein binding in human plasma with compound at 10 uM.
TetR sepsis: mg/kg required to protect 50% of mice in septicemia model with tetracycline-resistant *S. aureus* strain.
GN sepsis: mg/kg required to protect 50% of mice in septicemia model with *E. coli* strain.
Thigh Burden: maximum log10 reduction in bacteria compared to untreated control.
Maximum log10 reduction: maximum bacterial count (log10) reduction achieved at tested doses.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula:

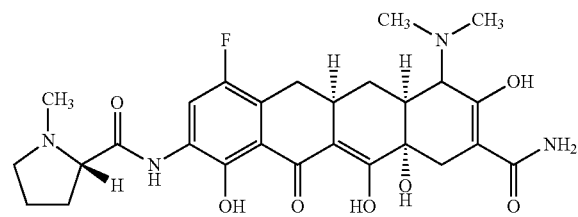

or a pharmaceutically acceptable salt thereof.

2. A pharmaceutical composition comprising a compound represented by the following structural formula:

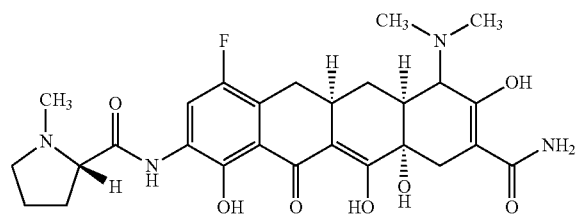 [SMILES: CN(C)C1C(O)=C(C(N)=O)C[C@@]2(O)C(O)=C3C(=O)c4c(O)c(NC(=O)[C@@H]5CCCN5C)cc(F)c4C[C@H]3C[C@@H]12]

or a pharmaceutically acceptable salt thereof and a pharmaceutically acceptable carrier or diluent.

* * * * *

UNITED STATES PATENT AND TRADEMARK OFFICE
CERTIFICATE OF CORRECTION

PATENT NO. : 8,501,716 B2  Page 1 of 1
APPLICATION NO. : 13/570837
DATED : August 6, 2013
INVENTOR(S) : Jingye Zhou et al.

It is certified that error appears in the above-identified patent and that said Letters Patent is hereby corrected as shown below:

In the Claims:

In Column 137, Claim 1, beginning at line 33 and ending at line 42, delete " 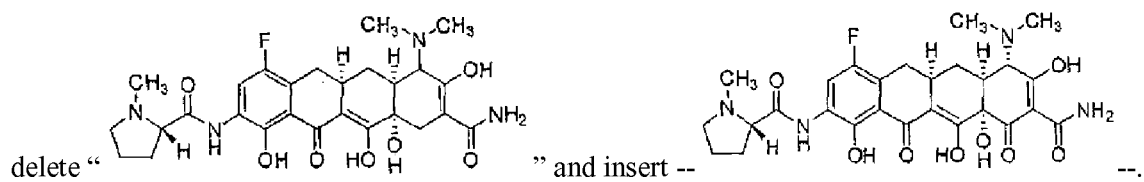 " and insert -- --.

In Column 138, Claim 2, beginning at line 25 and ending at line 38, delete " 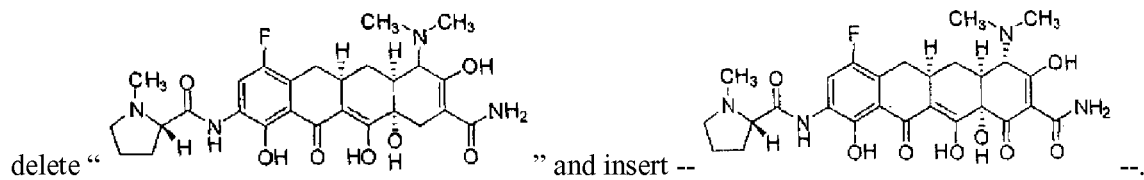 " and insert -- --.

Signed and Sealed this
Eleventh Day of March, 2014

Michelle K. Lee
*Deputy Director of the United States Patent and Trademark Office*